(12) United States Patent
Dalton et al.

(10) Patent No.: US 11,090,283 B2
(45) Date of Patent: *Aug. 17, 2021

(54) SOLID FORMS OF SELECTIVE ANDROGEN RECEPTOR MODULATORS

(71) Applicant: GTx, Inc., Memphis, TN (US)

(72) Inventors: James T. Dalton, Ann Arbor, MI (US); Thomas G. Bird, Eads, TN (US); Tai Ahn, Ellicott City, MD (US); David A. Dickason, Cordova, TN (US); Seoung-Soo Hong, Collierville, TN (US)

(73) Assignee: UNIVERSITY OF TENNESSEE RESEARCH FOUNDATION, Knoxville, TN (US)

( * ) Notice: Subject to any disclaimer, the term of this patent is extended or adjusted under 35 U.S.C. 154(b) by 387 days.

This patent is subject to a terminal disclaimer.

(21) Appl. No.: 15/361,049

(22) Filed: Nov. 24, 2016

(65) Prior Publication Data

US 2017/0266149 A1    Sep. 21, 2017

Related U.S. Application Data

(60) Continuation of application No. 14/875,181, filed on Oct. 5, 2015, now abandoned, which is a continuation of application No. 14/058,896, filed on Oct. 21, 2013, now Pat. No. 9,150,501, which is a division of application No. 13/153,427, filed on Jun. 5, 2011, now Pat. No. 8,563,606, which is a division of application No. 12/228,100, filed on Sep. 29, 2008, now Pat. No. 7,968,603, which is a continuation-in-part of application No. 12/209,137, filed on Sep. 11, 2008, now Pat. No. 7,977,386.

(60) Provisional application No. 60/960,012, filed on Sep. 11, 2007.

(51) Int. Cl.
  *A61K 31/277*  (2006.01)
  *C07C 255/60*  (2006.01)
  *C07C 253/30*  (2006.01)

(52) U.S. Cl.
  CPC .......... *A61K 31/277* (2013.01); *C07C 253/30* (2013.01); *C07C 255/60* (2013.01)

(58) Field of Classification Search
  CPC . A61K 31/277; A61P 5/00; A61P 5/26; C07C 253/30; C07C 255/60
  See application file for complete search history.

(56) References Cited

U.S. PATENT DOCUMENTS

| | | |
|---|---|---|
| 3,239,345 A | 3/1966 | Hodge et al. |
| 3,865,801 A | 2/1975 | Chiba et al. |
| 3,875,229 A | 4/1975 | Gold |
| 4,036,979 A | 7/1977 | Asato |
| 4,139,638 A | 2/1979 | Neri et al. |
| 4,191,775 A | 3/1980 | Glen |
| 4,239,776 A | 12/1980 | Glen et al. |
| 4,282,218 A | 8/1981 | Glen et al. |
| 4,386,080 A | 5/1983 | Crossley et al. |
| 4,411,890 A | 10/1983 | Momany et al. |
| 4,465,507 A | 8/1984 | Konno et al. |
| 4,636,505 A | 1/1987 | Tucker |
| 4,880,839 A | 11/1989 | Tucker |
| 4,977,288 A | 12/1990 | Kassis et al. |
| 5,162,504 A | 11/1992 | Horoszewicz |
| 5,179,080 A | 1/1993 | Rothkopf et al. |
| 5,441,868 A | 8/1995 | Lin et al. |
| 5,547,933 A | 8/1996 | Lin et al. |
| 5,609,849 A | 3/1997 | Kung |
| 5,612,359 A | 3/1997 | Murugesan et al. |
| 5,618,698 A | 4/1997 | Lin et al. |
| 5,621,080 A | 4/1997 | Lin et al. |
| 5,656,651 A | 8/1997 | Sovak et al. |
| 5,735,105 A | 4/1998 | Stroud et al. |
| 6,019,957 A | 2/2000 | Miller et al. |
| 6,043,265 A | 3/2000 | Murugesan et al. |
| 6,071,957 A | 6/2000 | Miller et al. |
| 6,160,011 A | 12/2000 | Miller et al. |
| 6,482,861 B2 | 11/2002 | Miller et al. |
| 6,492,554 B2 | 12/2002 | Dalton et al. |
| 6,548,529 B1 | 4/2003 | Robl et al. |
| 6,569,896 B2 | 5/2003 | Dalton et al. |
| 6,769,226 B2 | 8/2004 | Holland et al. |
| 6,777,427 B2 | 8/2004 | Miyakawa et al. |
| 6,838,484 B2 | 1/2005 | Steiner et al. |
| 6,899,888 B2 | 5/2005 | Steiner et al. |
| 6,960,474 B2 | 11/2005 | Salvati et al. |
| 6,995,284 B2 | 2/2006 | Dalton et al. |

(Continued)

FOREIGN PATENT DOCUMENTS

| | | |
|---|---|---|
| AU | 2002364949 | 6/2003 |
| AU | 2003216174 | 9/2003 |

(Continued)

OTHER PUBLICATIONS

Bhasin et al., Selective Androgen Receptor Modulators (SARMs) as Function Promoting Therapies. Curr. Opin. Clin. Nutr. Metab. Care, 12(3), pates 232-240 (Year: 2009).*

Abuchowski et al. "Immunosuppressive properties and circulating life of Achromobacter glutaminase-asparaginase covalently attached to polyethylene glycol in man" Cancer Treat Rep. 65(11-12):1077-81. Nov.-Dec. 1981.

Baird et al. "Hormonal Contraception—Drug Therapy", The New England Journal of Medicine , May 27, 1993, pp. 1543-1549.

Balthasar. "Bioequivalence and Bioequivalency Testing" Am. J. Pharm. Educ., 63, 194-198, (1999).

(Continued)

*Primary Examiner* — Barbara P Badio

(74) *Attorney, Agent, or Firm* — Mark S. Cohen; Pearl Cohen Zedek Latzer Baratz LLP

(57) ABSTRACT

The present invention relates to solid forms of (S)—N-(4-cyano-3-(trifluoromethyl)phenyl)-3-(4-cyanophenoxy)-2-hydroxy-2-methylpropanamide and process for producing the same.

4 Claims, 55 Drawing Sheets

(56) References Cited

U.S. PATENT DOCUMENTS

| | | | |
|---|---|---|---|
| 6,998,500 | B2 | 2/2006 | Dalton et al. |
| 7,022,870 | B2 | 4/2006 | Dalton et al. |
| 7,026,500 | B2 | 4/2006 | Dalton et al. |
| 7,041,844 | B2 | 5/2006 | Miller et al. |
| 7,129,377 | B2 | 10/2006 | Miller |
| 7,205,437 | B2 | 4/2007 | Dalton et al. |
| 7,213,511 | B2 | 5/2007 | Cruttenden et al. |
| 7,214,693 | B2 | 5/2007 | Dalton et al. |
| 7,344,700 | B2 | 3/2008 | Dalton et al. |
| 7,365,202 | B2 | 4/2008 | Tan et al. |
| 7,518,013 | B2 | 4/2009 | Dalton et al. |
| 7,547,728 | B2 | 6/2009 | Steiner et al. |
| 7,622,503 | B2 | 11/2009 | Dalton et al. |
| 7,645,898 | B2 | 1/2010 | Dalton et al. |
| 7,705,182 | B2 | 4/2010 | Dalton et al. |
| 7,759,520 | B2 | 7/2010 | Dalton et al. |
| 7,772,433 | B2 | 8/2010 | Dalton et al. |
| 7,825,229 | B2 | 11/2010 | Itzhak et al. |
| 8,080,682 | B2 | 12/2011 | Dalton et al. |
| 8,354,446 | B2 | 1/2013 | Zhi |
| 8,426,465 | B2 | 4/2013 | Dalton et al. |
| 8,563,606 | B2 | 10/2013 | Dalton et al. |
| 9,150,501 | B2 | 10/2015 | Dalton et al. |
| 2001/0012839 | A1 | 8/2001 | Miller et al. |
| 2002/0099036 | A1 | 7/2002 | Dalton et al. |
| 2002/0099096 | A1 | 7/2002 | Dalton et al. |
| 2002/0173445 | A1 | 11/2002 | Salvati et al. |
| 2003/0162761 | A1 | 8/2003 | Steiner et al. |
| 2003/0225040 | A1 | 12/2003 | Dalton et al. |
| 2003/0229099 | A1 | 12/2003 | Zhu et al. |
| 2003/0232792 | A1 | 12/2003 | Dalton et al. |
| 2003/0232882 | A1 | 12/2003 | Miller et al. |
| 2004/0014975 | A1 | 1/2004 | Dalton et al. |
| 2004/0029913 | A1 | 2/2004 | Dalton et al. |
| 2004/0053897 | A1 | 3/2004 | Steiner et al. |
| 2004/0087557 | A1 | 5/2004 | Steiner et al. |
| 2004/0087810 | A1 | 5/2004 | Dalton et al. |
| 2004/0147489 | A1 | 7/2004 | Dalton et al. |
| 2004/0197928 | A1 | 10/2004 | Dalton et al. |
| 2004/0214790 | A1 | 10/2004 | Borgens et al. |
| 2004/0224979 | A1 | 11/2004 | Dalton et al. |
| 2004/0260092 | A1 | 12/2004 | Miller et al. |
| 2004/0260108 | A1 | 12/2004 | Dalton et al. |
| 2004/0265916 | A1 | 12/2004 | Dalton et al. |
| 2005/0033074 | A1 | 2/2005 | Dalton et al. |
| 2005/0038110 | A1 | 2/2005 | Steiner et al. |
| 2005/0137172 | A1 | 6/2005 | Dalton et al. |
| 2005/0154043 | A1 | 7/2005 | Zhai et al. |
| 2006/0004042 | A1 | 1/2006 | Dalton et al. |
| 2006/0009488 | A1 | 1/2006 | Miller et al. |
| 2006/0019931 | A1 | 1/2006 | Dalton et al. |
| 2006/0035965 | A1 | 2/2006 | Dalton et al. |
| 2006/0088590 | A1 | 4/2006 | Sukuru et al. |
| 2006/0111441 | A1 | 5/2006 | Dalton et al. |
| 2006/0165744 | A1 | 7/2006 | Jamil et al. |
| 2006/0183931 | A1 | 8/2006 | Dalton et al. |
| 2006/0229362 | A1 | 10/2006 | Dalton et al. |
| 2006/0276539 | A1 | 12/2006 | Dalton et al. |
| 2006/0287349 | A1 | 12/2006 | Meissner et al. |
| 2007/0066568 | A1 | 3/2007 | Dalton et al. |
| 2007/0123563 | A1 | 5/2007 | Dalton et al. |
| 2007/0129548 | A1 | 6/2007 | Tan et al. |
| 2007/0161608 | A1 | 7/2007 | Dalton et al. |
| 2007/0173546 | A1 | 7/2007 | Dalton et al. |
| 2007/0281906 | A1 | 12/2007 | Dalton et al. |
| 2008/0076828 | A1 | 3/2008 | Dalton et al. |
| 2009/0088480 | A1 | 4/2009 | Dalton et al. |
| 2009/0264534 | A1 | 10/2009 | Dalton et al. |
| 2010/0022641 | A1 | 1/2010 | Dalton et al. |
| 2010/0137430 | A1 | 6/2010 | Dalton et al. |
| 2010/0144871 | A1 | 6/2010 | Steiner et al. |
| 2010/0249228 | A1 | 9/2010 | Dalton et al. |
| 2010/0280107 | A1 | 11/2010 | Dalton et al. |
| 2013/0034562 | A1 | 2/2013 | Dalton et al. |
| 2014/0018433 | A1 | 1/2014 | Dalton et al. |
| 2014/0080905 | A1 | 3/2014 | Dalton et al. |
| 2014/0350102 | A1 | 11/2014 | Dalton et al. |
| 2016/0128968 | A1 | 5/2016 | Dalton et al. |

FOREIGN PATENT DOCUMENTS

| | | |
|---|---|---|
| CA | 1305665 | 7/1992 |
| CA | 2149240 | 5/1994 |
| CA | 2247946 | 10/1997 |
| CA | 2281570 | 9/1998 |
| CA | 2313089 | 6/1999 |
| CA | 2344316 | 3/2000 |
| CA | 2420279 | 2/2002 |
| CA | 2458452 A1 | 2/2003 |
| CA | 2477737 | 9/2003 |
| CA | 2502209 | 4/2004 |
| CA | 2502355 | 4/2004 |
| CA | 2538095 | 4/2004 |
| CA | 2529464 | 1/2005 |
| CA | 2536518 | 2/2005 |
| CN | 1825959 A | 8/2006 |
| EA | 200602278 | 4/2007 |
| EP | 0040932 | 2/1981 |
| EP | 0100172 | 2/1984 |
| EP | 0002892 | 2/1985 |
| EP | 0253503 | 12/1991 |
| EP | 668351 | 8/1995 |
| EP | 1221439 | 7/2002 |
| EP | 1401801 | 11/2006 |
| EP | 1801140 | 6/2007 |
| GB | 1360001 | 3/1970 |
| JP | 52-128329 | 10/1977 |
| JP | 54-63047 | 12/1980 |
| JP | 59-033250 | 2/1984 |
| JP | 2006-199704 | 3/2006 |
| WO | WO 1989/007110 | 8/1989 |
| WO | WO 1989/007111 | 8/1989 |
| WO | WO 1991/005867 | 5/1991 |
| WO | WO 1993/004081 | 3/1993 |
| WO | WO 1995/019770 | 7/1995 |
| WO | WO 1998/005962 | 2/1998 |
| WO | WO 1998/053826 A1 | 12/1998 |
| WO | WO 1998/055153 | 12/1998 |
| WO | WO 2000/001389 | 1/2000 |
| WO | WO 2001/27086 | 4/2001 |
| WO | WO 2001/027622 | 4/2001 |
| WO | WO 2001/028990 | 4/2001 |
| WO | WO 2001/034563 | 5/2001 |
| WO | WO 2001/068603 | 9/2001 |
| WO | WO 2002/000617 | 1/2002 |
| WO | WO 2002/016310 | 2/2002 |
| WO | WO 2002/22585 | 3/2002 |
| WO | WO 2003/011302 | 2/2003 |
| WO | WO 2003/049675 | 6/2003 |
| WO | WO 2003/065992 | 8/2003 |
| WO | WO 03/074449 | 9/2003 |
| WO | WO 2003/074449 | 9/2003 |
| WO | WO 2003/074471 | 9/2003 |
| WO | WO 2003/077919 | 9/2003 |
| WO | WO 2004/034978 | 4/2004 |
| WO | WO 2004/035736 | 4/2004 |
| WO | WO 2004/035738 | 4/2004 |
| WO | WO 2004/062612 | 7/2004 |
| WO | WO 2004/064747 A2 | 8/2004 |
| WO | WO 2005/000794 | 1/2005 |
| WO | WO 2005/037201 | 4/2005 |
| WO | WO 2005/037205 | 4/2005 |
| WO | WO 2005/037206 | 4/2005 |
| WO | WO 2005/060647 | 7/2005 |
| WO | WO 2005/120483 | 8/2006 |
| WO | WO 2007/027582 A2 | 3/2007 |
| WO | WO 2008/024456 | 7/2008 |
| WO | WO 2008/127717 | 10/2008 |
| WO | WO 2009/036206 | 3/2009 |
| WO | WO 2009/137602 A1 | 11/2009 |

(56) References Cited

FOREIGN PATENT DOCUMENTS

WO WO 2009/155481 12/2009
WO WO 2012/139093 A2 10/2012

OTHER PUBLICATIONS

Belani, C.P. et al, "Development of docetaxel in advanced non-small-cell lung cancer." Lung Cancer, 46, pp. S3-S11, 2004.
Belikov "Pharmaceutical chemistry", high school, 1993, vol. 1, pp. 43-47.
Berger et al., "Concepts and limitations in the application of radiolabeled antiandrogens, estrogens, or androgens as isotropic scanning agents for the prostate", Invest. Urol, (1975), 1391, 10-16.
Bhasin et al. "Drug insight: Testosterone and selective androgen receptor modulators as anabolic therapies for chronic illness and aging" Nature, Clinical Practice in Endocrinology and Metabolism, 2(3): 146-159,2006.
Bisson et al. "Discovery of antiandrogen activity of nonsteroidal scaffolds of marketed drugs" Proceedings of the National Academy of Sciences, U S A. 104(29): 1192741932, 2007.
Bohl et al. "A Ligand-Based Approach to Identify Quantitative Structure-Activity Relationships for the Androgen Receptor" Journal of Medicinal Chemistry, 47(15):3765-3776, 2004.
Bohl et al. "Structural Basis for Antagonism and Resistance of Bicalutamide in Prostate Cancer" Proc Natl Acad Sci USA. 102(17): 6201-6206, 2005.
Bohl et al. "Structural Basis for Accomodation of Nonsteroidal Ligaiids in the Androgen Receptor". Journal of Biological Chemistry, 280(45):37747-37754, 2005.
Bohl et al. "Crystal structure of the TS77A human androgen receptor Ugand-binding domain completed to cyproterone acetate provides insight for ligand-induced conformational changes and structure-based drug design". Journal of Biological Chemistry, 282(18):13648-13655,2007.
Boyanov MA et al. "Testosterone supplementation in men with type 2 diabetes,visceral obesity and partial androgen deficiency" Aging Male., vol. 6 No. 1, pp. 1-7, Mar. 2003.
Brittain et al., editors "Polymorphism in pharmaceutical solids", Chapter 1 pp. 1-10 and Guillory Chapter 5 pp. 183-226, 1999.
Brown et al. Nonsteroidal Selective Androgen Receptors Modulators (SARMs) Designer Androgens with Flexible Structures Provide Clinical Promise Endocrinology 145: 5417-5419, (2004).
Bruera et al. ABC of palliative care. Anorexia, cachexia, and nutrition. BMJ, 315: 1219-1222, (1997).
Buchwald et al. "Long-term, continuous intravenous heparin administration by an implantable infusion pump in ambulatory patients with recurrent venous thrombosis." Surgery 88:507 (1980).
Byrn et al.; "Pharmaceutical Solids: A Strategic Approach to Regulatory Considerations"; Pharmaceutical research, vol. 12, No. 7. p. 945-954 (1995).
Cabrespine et al. "Randomized phase II study comparing paclitaxel and carboplatin versus mitoxantrone in patients with hormone-refractory prostate cancer" Urology. Feb. 28, 2006;67(2):354-9.
Caira et al. "Crystalline Polymorphism of Organic Compounds", Topic in current chemistry vol. 1998, 198:163-208.
Campfield et al., 1995, "Recombinant mouse OB protein: evidence for a peripheral signal linking adiposity and central neural networks" Science 269:546-549.
Caprio et al.; "Fat distribution and cardiovascular risk factors in obese adolescent girls: importance of the intraabodomina fat dept", Am J Clin Nutr 1996;64:12-7.
Chen et al. "A Selective Androgen Receptor Modulator (SARM) for Hormonal Male Contraception". Journal of Pharmacology and Experimental Therapeutics, 312(2): 546-553,2005.
Chen et al. "Discovery and Therapeutic Promise of Selective Androgen Receptor Modulators" Molecular Interventions, 5(3):173-188I 2005.

Chen et al. "In vitro and in vivo structure-activity relationships of novel androgen receptor ligands with multiple substituents in the B-ring". Endocrinology, 146(12):5444-54, 2005.
Considine et al., 1995, "Evidence against either a premature stop codon or the absence of obese gene mRNA in human obesity." J. Clin. Invest. 95:2986-2988.
Corey (1987) "Asymmetric Bromolactonization Reaction: Synthesis of Optically Active 2-hydroxy-2-Methylalkanoic Acids from 2-Methylalkanoic Acids" Tetrahedron Letters vol. 28, No. 25 2801-2804.
Dalton et al., "Therapeutic Promise of Selective Androgen Receptor Modulators (SARS): Preclinical and Clinical Proof-of-Concept Studies"—The Endocrine Society-Programs and Abstracts—89th Annual meeting—Paper S41-2.
Dalton et al. Discovery of Nonsteroidal Androgens. Biochem. Biophys. Res. Commun.,244(1):1-4, 1998.
Dalton et al "Pharmacokinetics of Aminolevulinic Acid after Oral and Intravenous Dosing in Dogs." Drug Metabolism and Disposition, 27 (4):432-435, 1999.
De Amicis et al. "Androgen receptor overexpression induces tamoxifen resistance in human breast cancer cells", Breast Cancer Res Treat. May 2010;121(1):1-11.
Dewys et al. "Prognostic effect of weight loss prior to chemotherapy in cancer patients" Eastern Cooperative Oncology Group. Am J Med.; 69(4): 491-7. (1980).
Diebold et al. "Innate antiviral responses by means of TLR7-mediated recognition of single-stranded RNA". Science. Mar. 5, 2004;303(5663):1529-31.
Djerassi et al. "A new look at male contraception", Nature, vol. 370, pp. 11-12, 1994.
Edwards et al. "Nonsteroidal androgen receptor agonists based on 4-(trifluoromethyl)-2H-pyrano[3,2-g]quinolin-2-one. Bioorg" Med. Chem. Lett., 9: 1003, 1999.
Edwards et al. "New nonsteroidal androgen receptor modulators based on 4-(trifluoromethyl)-2-(1H)-Pyrololidino[3,2-g]quinolone". Bioorg. Med. Chem. Lett., 8: 745, 1998.
Eliason et al., "High Throughput Fluorescence Polarization-Based Screening Assays for the Identification of Novel Nuclear Receptor Ligands," Abstracts of Papers, 223rd ACS National Meeting, Orlando, FL, United States, (2002), Apr. 7, 2002.
European Search Report for European Application No. 14190028.2 dated Apr. 14, 2015.
Faulkner et al (1991) "Noninvasive measurements of bone mass, structure, and strength: current methods and experimental techniques." Am J Rosentgenology 157:1229-1237.
Fisher et al. "Preclinical Pharmacology and Pharmacokinetics of a Novel A-ring Substituted Selective Androgen Receptor Modulator (SARM) in Rats" The AAPS Journal, vol. 6, No. 4, Abstract #T2256, Nov. 2004.
Foulks et al. "Blepharitis: A Review for Clinicians", Refractive Eyecare vol. 13, No. 3, Mar. 2009.
Francisco et al., "Long-acting contraceptive agents: testosterone esters of unsaturated acids", Steroids, Jan. 1990, vol. 55, Butterworths.
Fukui et al. "Role of endogenous androgen against insulin resistance and atherosclerosis in men with type 2 diabetes" Curr Diabetes Rev., vol. 3 No. 1, pp. 25-31, Feb. 2007.
Gao et al. "Species Difference in the Metabolism of Selective Androgen Receptor Modulators (SARMs)" PharmSci 5 (4): T3336, 2003.
Gao et al. "Regulation of Cytochrome P450s by Selective Androgen Receptor Modulators (SARMs) in Primary Culture of Human Hepatocytes". PharmSci 5 (4): T3 3 3 8, 2003.
Gao et al. "Effects of a Novel Selective Androgen Receptor Modulator (SARM) on Skeletal Muscle Mass and Strength in Castrated Male Rats" The Endocrine Society, New Orleans, Abstract # P2-120, Jun. 2005.
Gao et al. "Pharmacologic Effects of a Novel Selective Androgen Receptor Modulator (SARM), Flutamide and Finasteride in Intact Male Rats" The Endocrine Society, Philadelphia, Jun. 2003, Abstract #P3-221.
Gao et al. "In Vitro Metabolism and In Vivo Tissue Selectivity of Andarine" PharmSci 4(4): 2002.

(56) References Cited

OTHER PUBLICATIONS

Gao, et al. "Comparison of the Pharmacological Effects of a Novel Selective Androgen Receptor Modulator (SARM), the 5{alpha}-Reductase Inhibitor Finasteride, and the Antiandrogeo Hydroxyflutamide in Intact Rats: New Approach for Benign Prostate Hyperplasia (BPH)" Endocrinology, 145(12): 5420-5428, 2004.

Gao et al. "Selective Androgen Receptor Modulator (SARM) Treatment Improves Muscle Strength and Body Composition, and Prevents Bone Loss in Orchidectomized Rats" Endocrinology, 146(11):4887-4897, 2005.

Gao et al. "Chemistry and structural biology of androgen receptor" Chemical Reviews, 1G5(9):3352-70,2005.

Gao et al. "Inter-Species Differences in Pharmacokinetics and Metabolism of S-3-(4-acelylamino-phenoxy)-2-hydroxy-2-methyl-N-(4-nitro- 3-trifluoromethyi-phenyl>propionamide: The Role of N-Acetyltransferase" Drug Metabolism and Disposition, 34(2):254-260, 2006.

Gao et al. "Characterization of the In vitro Metabolism of Selective Androgen Receptor Modulator (SARM) Using Human, Rat and Dog Liver Enzyme Preparations". Drug Metabolism and Disposition, 34(2):243-253, 2006.

Gao et al. "Pharmacokinetics and Pharmacodynamics of Nonsteroidal Androgen Receptor Ligands" Pharmaceutical Research, 23(8):1641-165B, 2006.

Gao et al. "Expanding the therapeutic use of androgens via selective androgen receptor modulators (SARMs)". Drug Discovery Today, 12(5-6):241-248, 2007.

Gao et al. "Ockham's razor and selective androgen receptor modulators (SARMs): are we overlooking the role of 5a-reductase?" Molecular Interventions, 7(1):1Q-13, 2007.

Garay et al. "Androgen receptor as a targeted therapy for breast cancer", Am J Cancer Res. 2012;2(4):434-45.

Goodson, in Medical Applications of controlled Release, supra, vol. 2, pp. 115-138 (1984).

Grundy, Metabolic and health complications of obesity, 1990, Disease-a-Month 36:Dec.; 36(12):641-731.

Halaas et al., 1995, "Weight-reducing effects of the plasma protein encoded by the obese gene." Science 269:543-546.

Hamann et al. "Discovery of a potent, orally active nonsteroidal androgen receptor agonist: 4-ethyl-1,2,3,4-tetrahydro-6-(trifluoromethyl)-8-pyridono[5,6-g]-quinoline (LG121071)" J. Med. Chem., 42: 210, 1999.

Hamilton et al., 1995, « Increased obese mRNA expression in omental fat cells from massively obese humans. Nature Med. 1:953.

Hanada et al (2003) "Bone anabolic effects of S-40503, a novel nonsteroidal selective androgen receptor modulator (SARM), in rat models of osteoporosis." Biol. Pharm. Bull. 26:1563-1569.

Handelsman "Bridging the gender gap in contraception: another hurdle cleared" The Medical Journal of Australia, vol. 154, Feb. 18, 1996, pp. 230-233.

He et al. "Novel Nonsteroidal Ligands with High Affinity and Potent Functional Activity for the Human Androgen Receptor" European Journal of Medicinal Chemistry, 37: 619-634, 2002.

Heil et al. "species-specific recognition of single-stranded RNA via toll-like receptor 7 and 8" Science. Mar. 5, 2004;303(5663):1526-9.

Higuchi et al. "4-Alkyl- and 3,4-diaklyl-1,2,3,4-tetrahydro-8-pyridono[5,6-g]quinolines: potent, nonsteroidal androgen receptor agonists". Bioorg. Med. Chem. Lett., 9:1335,1999.

Hoberman et al. "The History of Synthetic Testosterone", Scientific American, Feb. 1995, pp. 76-81.

Hwang et al. "Synthesis and testing of both reversible and irreversible selective androgen receptor modulators (SARMs) for prostate cancer" Abstracts of Papers of the American Chemical Society, 231: 274-MEDI, Mar. 26 2006.

Hwang et al. "Synthesis and biological testing of (2S)-multU halogenated B-ring 2-hydroxy-2-methylpropionamide selective androgen receptor modulators (SARMs): Probing the B-ring pocket" Abstracts of Papers of the American Chemical Society, 229: U140-U140 176—MEDI Part 2, Mar. 13, 2005.

Hwang et al. "Synthesis of isothiocyanate derivatives of irreversible selective androgen receptor modulators (SARMs) and biological testing in prostate cancer cell lines" Abstracts of Papers of the American Chemical Society, 229: U140-U140 177—Medi Part 2, Mar. 13, 2005.

Hwang et al. "Aryl isothiocyanato selective androgen receptor modulators (SARMs) for prostate cancer". Bioorganic and Medicinal Chemistry, 14(19):6525-6538, 2006.

International Search Report for Application No. PCT/US08/76066 dated Dec. 18, 2008.

Joffre et al. "Differences in meibomian fatty acid composition in patients with meibomian gland dysfunction and aqueous-deficient dry eye", Br J Ophthalmol. Jan. 2008;92(1):116-9.

Kalu, DN, (1991) "The ovariectomized rat model of postmenopausal bone loss. Bone Miner." 15" 175-91.

Katre et al. "Chemical modification of recombinant interleukin 2 by polyethylene glycol increases its potency in the murine Meth A sarcoma model" Proc Natl Acad Sci U S A. 84(6):1487-91. Mar. 1987.

Kearbey et al. "Selective androgen receptor modulators inhibit bone resorption in rats" PharmSci 5 (4): R6167, 2003.

Kearbey et al. "Selective Androgen Receptor Modulator (SARM) Treatment Prevents Bone Loss and Reduces Body Fat in Ovariectomized Rats" Pharmaceutical Research, 24(2):328-335, 2006.

Kearbey et al. (2004) "Pharmacokinetics of S-3-(4-acetylamino-phenoxy)-2-hydroxy 2-methyl-N-(4-nitro- 3-trifluoromethyl-phenyl)-propionamide in rats, a non-steroidal selective androgen receptor modulator" Xenobiotica 34(3), 273-80.

Kelly et al. "Dose escalation study of intravenous estramustine phosphate in combination with Paclitaxel and Carboplatin in patients with advanced prostate cancer" Clinical cancer research. Jun. 1, 2003;9(6):2098-107.

Kim et al. "Structure-Activity Relationships for Modification of the Linkage Group and B-Ring of Selective Androgen Receptor Modulators" The AAPS Journal, vol. 7(S2):T2117,2005.

Kim et al. "In vitro and In vivo Pharmacologic Activity of 4-Halo Substituted SARMs" The Endocrine Society, Philadelphia, Jun. 2003, Abstract #P3-198.

Kim et al. "The 4-Para-Substituent of S-3-(Phenoxy)-2-hydroxy-2-methyl-N-(4-nitro-3-trifluoromethyl]-phenyl)-propionamides is a Major Structural Determinant of In Vivo Disposition and Activity of Selective Androgen Receptor Modulators" Journal of Pharmacology and Experimental Therapeutics, 315(I):230-239, 2005.

Kirkovsky et al., "[1251]-Radionated Bicalutamide Analogs as Potential Imaging Agents for Prostate Cancer", Poster Presentation MEDI 155, 214th ACS National Meeting, Las Vegas, NV, Sep. 7-11, 1997, Department of Pharmaceutical Sciences, University of Tennessee, Memphis, TN 38163.

Kirkovsky et al. "Approaches to Irreversible non-steroidal chiral antiandrogens" Department of Pharmaceutical Sciences, University of Tennessee, 47th Southeast/51st Southwest Joint Regional Meeting of the American Chemical Society, Memphis, TN, Nov. 29-Dec. 1, 1995.

Kirkovsky et al. "Chiral Nonsteroidal Affinity Ligands for the Androgen Receptor. 1. Bicalutamide Analogs bearing Electrophilic Groups at the Aromatic Ring B" Journal of Medicinal Chemistry, 43: 581-590, 2000.

Kori et al. "Early Phase II Study of Combination Chemotherapy of Docetaxel and Carboplatin in Patients With Postoperative Recurrent Adenocarcinoma of the Lung", Apr. 20, 2002, Japanese Journal of Jung Cancer, vol. 42, No. 2, pp. 85-91.

Koski GK et al. "Cutting edge: innate immune system discriminates between RNA containing bacterial versus eukaryotic structural features that prime for high-level IL-12 secretion by dendritic cells" J Immunol. Apr. 1, 2004;172(7):3989-93.

Laaksonen et al., "Sex hormones, inflammation and the metabolic syndrome: a population-based study", European Journal of Endocrinology, Dec. 2003, vol. 149, No. 6, pp. 601-608.

Langer (1990) "New methods of drug delivery" Science 249:1527-1533.

Lönnqvist et al. "Overexpression of the obese (ob) gene in adipose tissue of human obese subjects" Nature medicine, Sep. 1995;1(9):950-3.

(56) References Cited

OTHER PUBLICATIONS

Lopez-Berestein in Liposomes in the Therapy of Infectious Disease and Cancer, Lopez- Berestein and Fidler (eds.), Liss, New York, pp. 317-327. (1984).
MacDonald et al. "Understanding and managing cancer cachexia", J. American College of Surgeons, vol. 197, pp. 143-161, 2003.
Marhefka et al. "Homology Modeling Using Multiple Molecular Dynamics Simulations and Docking Studies of the Human Androgen Receptor Ligand Binding Domain Bound to Testosterone and Nonsteroidal Ligands" Journal of Medicinal Chemistry, 44: 1729-1740, 2001.
Marhefka et al. (2004) "Design, synthesis, and biological characterization of metabolically stable selective androgen receptor modulators" J Med Chem 47(4), 993-8.
Matsumoto, 1994, "Hormonal therapy of male hypogonadism" Endocrinol. Met. Clin. N. Am. 23:857-75.
McKillop et al., "Enantioselective metabolism and pharmacokinetics of Casodex in the male rat", Xenobiotica, 1995, vol. 25, No. 6, 623-634.
Mishra et al. "Expression of androgen receptor in breast cancer & its correlation with other steroid receptors & growth factors", Indian J Med Res. Jun. 2012;135(6):843-52.
Monaco et al. "Cloning of the Duchenne/Becker muscular dystrophy locus", Adv Hum Genet. 1988;17:61-98.
Mukherjee et al. Enantioselective Binding of Casodex to the Androgen Receptor. Xenobiotica 26(2): 117-122, 1996.
Mukherjee et al. "Affinity Labeling of the Androgen Receptor with Nonsteroidal Chemoaffinity Ligands" Biochemical Pharmacology, 58: 1259-1267, 1999.
Mukherjee et al. "Development of Nonsteroidal Androgen Receptor Ligands for Imaging Prostate Tumors". PharmSci, 1(1):S-681, 1998.
Nair et al. "Synthesis of Novel lodo Derived Bicalutamide Analogs" Tetrahedron Letters, 45: 9475-9477, 2004.
Nair et al. "Synthesis of irreversibly binding bicalutamide analogs for imaging studies" Tetrahedron Letters. 46:4821-4823, 2005.
Nair et al. "Synthesis of oxazolidinedione derived bicalutamide analogs" Tetrahedron Letters, 47 (23): 3953-3955, 2006.
Narayanan et al "Steroidal Androgens and Nonsteroidal, Tissue Selective Androgen Receptor Modulators (SARM) Regulate Androgen Receptor Function Through Distinct Genomic and Non-Genomic Signaling Pathways." The Endocrine Society—Programs and Abstracts—89th Annual Meeting—Paper P1-595.
Narayanan et al. "Molecular Mechanism for the Tissue Selectivity of a Novel Non-Steroidal Selective Androgen Receptor Modulator: Genome-Wide Mapping of Androgen Receptor Binding Sites" The Endocrine Society, Boston, Abstract # OR49-1, Jun. 2006.
Narayanan et al. "Steroidal Androgens and Nonsteroidal, Tissue Selective Androgen Receptor Modulators (SARM) Regulate Androgen Receptor Function Through Distinct Genomic and Non-Genomic Signaling Pathways" The Endocrine Society, Toronto, Abstract #PI-595, Jun. 2007.
Negro-Vilar, A. (1999) "Selective androgen receptor modulators (SARMs): a novel approach to androgen therapy for the new illennium." J. Clin. Endocrin Metabol. 84: 3459-3462.
Nelson, S. D. (2001). Structure Toxicity Relationships-How Useful Are They in Predicting Toxicities of New Drugs? In Biological reactive intermediates VI (pp. 33-43). Springer US.
Njelekela et al.; "Obesity and lipid Profiles in Middle Aged Men and Women in Tanzania", East African Medical Journal, Vo. 79 No. 2, Feb. 2002.
Office Action for Japanese Application No. 2014-005551 dated Jan. 27, 2015.
Office Action for Russian Patent Application No. 2011137324 dated Jan. 30, 2014.
Patil et al. Cesium fluoride and tetra-n-butylammonium fluoride mediated 1,4-N-O shift of disubstituted phenyl ring of a bicalutamide derivative. Tetrahedron Letters, 47:3941-3944, 2006.
Pelleymounter et al. 1995, "Effects of the obese gene product on body weight regulation in ob/ob mice" Science 269:540-543.
Perera et al. "Pharmacokinetics and Allometric Scaling of Andarine" PharmSci 4(4): 2002.
Rosen et al. "Intracellular receptors and signal transducers and activators of transcription superfamilies: novel targets for small-molecule drug discovery" J. Med. Chem., 38: 4855, 1995.
Rosen et al. "Novel, non-steroidal, selective androgen receptor modulators (SARMs) with anabolic activity in bone and muscle and improved safety profile", J Musculoskel Neuron Interact 2002, 2(3):222-224.
Saudek et al."A preliminary trial of the programmable implantable medication system for insulin delivery." N. Engl. J. Med. 321:574 (1989).
Sefton, 1987, "Implantable pumps." CRC Crit. Ref. Biomed. Eng. 14:201.
Segal et al. "Therapeutic potential of the SARMs: revisiting the androgen receptor for drug discovery" Expert Opinion in Investigational Drugs. 15(4):377-87, 2006.
Sharifi et al. "A bifunctional colchicinoid that binds to the androgen receptor" Molecular Cancer Therapeutics, 6(8):2328-2336, 2007.
Silverman "The Organic Chemistry of Drug Design and Drug Action", Academic Press, 1992, pp. 15-22.
Singh et al., 2003, "Androgens stimulate myogenic differentiation and inhibit adipogenesis in C3H 10T1/2 pluripotent cells through an androgen receptor-mediated pathway." Endocrinology, 144(11):5081-8.
Steinberger et al. "Effect of chronic Administration of Testosterone Enanthate on Sperm Production and Plasma Testosterone, Follicle Stimulating Hormone, and Luteinizing Hormone Levels: a Preliminary Evaluation of possible Male Contraceptive" Fertility and Sterility 28:1320-28 (1977).
Sullivan et al. "Androgen deficiency, meibomian gland dysfunction, and evaporative dry eye" Annals of the New York Academy of Sciences, Jun. 1, 2002;966(1)211-22.
Sundaram et al. "7 Alpha-Methyl-Nortestosterone (MENT): The Optimal Androgen for Male Contraception", Ann. Med., 25:199-205 (1993).
Supplementary European Search Report of Application No. EP 08799476.0 dated Mar. 20, 2012.
Treat et al., in Liposomes in the Therapy of infections disease and cancer, Lopez-Berestein and Fidler (eds.), Liss New York, pp. 353-365 (1989).
Tucker et al. "Resolution of the non steroidal antiandrogen 4'-cyano-3-[(4-fluorophenyl) sulfonyl]-2-hydroxy-2-methyl-3'-(trifluoromethyl) propionanilide and the determination of the absolute configuration of the active enantiomer" Journal of medicinal chemistry. Apr. 1988;31(4):885-7.
Tucker et al "Nonsteroidal antiandrogens. Synthesis and structure-activity relationships of 3-substituted derivatives of 2-hydroxypropionanilides." J. Med Chem (1988), 31, 954-959.
Vippagunta et al. "Crystalline solids", Adv Drug Deliv Rev. May 16, 2001;48(1):3-26.
Wahner, et al (1985) "Bone Mineral Density of the Radius" J. Nucl Medicine 26 13-39.
Wahner, et al (1984) "Assesment of Bone Mineral Part 1" J Nucl. Medicine, 1134-1141.
Wang et al. "Androgen Receptor Mediated Transcriptional Activation of SARMs is Enhanced by Nuclear Receptor Coactivators" The Endocrine Society, Philadelphia, Jun. 2003, Abstract #P2-95.
Watkins, "Cardiovascular disease, hypertension, and lipids", BMJ. Apr. 19, 2003;326(7394):874-6.
World Health Organisation Task Force on Methods for the Regulation of Male Fertility, "Contraceptive efficacy of testosterone-induced azoospermia in normal men", The Lancet, vol. 336, Oct. 20, 1990, pp. 955-959 and 1517-1518.
World Health Organization Task Force on Methods and Regulation of Male Fertility "Contraceptive Efficacy of Testosterone-Induced Azoospermia and Oligospermia in Normal Men", Fertility & Sterility 65:821-29 (1996).
Wu "Male Contraception: Current Status and Future Prospects" Clinical Endocrinology, (1988), 29, pp. 443-465.
Wu et al. "Urinary Metabolites of S-I, ANovel Selective Androgen Receptor Modulator (SARM), In Rats" The AAPS Journal, vol. 6, No. 4, Abstract #W53OO, Nov. 2004.

(56) References Cited

OTHER PUBLICATIONS

Wu et al. "The Favorable Effects of Weak Acids on Negative-Ion Electrospray Mass Spectrometry" Analytical Chemistry, 76(3):839-847, 2004.

Wu "Effects of Testosterone Enanthate in Normal Men: Experience from a Multicenter contraceptive efficacy study", Fertility and Sterility 65:626-36 (1996).

Wu et al. "Pharmacokinetics and metabolism of a selective androgen receptor modulator (SARM) in rats-implication of molecular properties and intensive metabolic profile to investigate ideal pharmacokinetic characteristics of a propanamide in preclinical study" Drug Metabolism and Disposition, 34(3):483-494, 2006.

Xu et al. "Pharmacodynamics of Electrophilic Androgen Receptor Ligands in Prostate Cancer Cell Lines" PharmSci 4(4): 2002.

Xu et al. "In Vitro and In Vivo Anticancer Activity of S-NTBA for Prostate Cancer" PharmSci 5 (4): T2378, 2003.

Yang et al. "Preclinical pharmacology of a nonsteroidal ligand for androgen receptor mediated imaging of prostate cancer" Journal of Pharmacology and Experimental Therapeutics, 317(I):402-408, 2006.

Yepuru et al "An Angrogen Receptor-b Specific Selective Estrogen Receptor Modulator (SERM) Inhibits the Growth of the Prostate Cancer Cells and Stromal-Epithilial Tumor Xenograft" The Endocrine Society—Programs and Abstracts—89th Annual Meeting—Paper OR6-3.

Yin et al. "Key Structural Features of Nonsteroidal Ligands for Binding and Activation of the Androgen Receptor" Molecular Pharmacology, 63:211-223, 2003.

Yin et al. "Pharmacology, Pharmacokinetics and Metabolism of Acetothiolutamide, A Novel Nonsteroidal Agonist for the Androgen Receptor" Journal of Pharmacology and Experimental Therapeutics, 304(3):1323-1333, 2003.

Yin et al. "Pharmacodynamics of Selective Androgen Receptor Modulators" Journal of Pharmacology and Experimental Therapeutics, 304(3): 1334-1340, 2003.

Yin et al. "In Vitro Pharmacology and In Vivo Pharmacokinetics of (R)-Para-Acetamido-Bicalutamide" PharmSci, 1(4):S-3185, 1999.

Zhi et al. "Switching androgen receptor antagonists to agonists by modifying C-ring substituents on piperidino[3,2-g]quinolone" Bioorg. Med. Chem. Lett., 9: 1009, 1999.

Zhou et al. "pecificity of ligand-dependent androgen receptor stabilization: receptor dornain interactions influence ligand dissociation and receptor stability" Molecular Endocrinology. Feb. 1995;9(2):208-18.

Zilbermint et al. "Nonsteroidal selective androgen receptor modulator Ostarine in cancer cachexia" Future Oncol. (2009) 5(8) pp. 1211-1220.

Examination Report dated May 20, 2019 issued in corresponding. Indian Application No. 201718032469.

* cited by examiner

SOLID FORMS OF SELECTIVE ANDROGEN RECEPTOR MODULATORS

CROSS REFERENCE TO RELATED APPLICATIONS

This application is a Continuation application of U.S. application Ser. No. 14/875,181, filed on Oct. 5, 2015, which is a Continuation application of U.S. application Ser. No. 14/058,896, filed on Oct. 21, 2013 which is a Divisional application of U.S. application Ser. No. 13/153,427, filed on Jun. 5, 2011 which is a Divisional application of U.S. application Ser. No. 12/228,100, filed on Sep. 29, 2008 which is a Continuation-In-Part of U.S. application Ser. No. 12/209,137, filed on Sep. 11, 2008, which claims the benefit of U.S. Provisional Application Ser. No. 60/960,012, filed on Sep. 11, 2007, which are incorporated in their entirety herein by reference.

FIELD OF INVENTION

The present invention relates to solid forms of (R) or (S)—N-(4-cyano-3-(trifluoromethyl)phenyl)-3-(4-cyanophenoxy)-2-hydroxy-2-methylpropanamide and processes of preparation thereof.

BACKGROUND OF THE INVENTION

The androgen receptor ("AR") is a ligand-activated transcriptional regulatory protein that mediates induction of male sexual development and function through its activity with endogenous androgens. Androgens are generally known as the male sex hormones. The androgenic hormones are steroids which are produced in the body by the testes and the cortex of the adrenal gland or can be synthesized in the laboratory. Androgenic steroids play an important role in many physiologic processes, including the development and maintenance of male sexual characteristics such as muscle and bone mass, prostate growth, spermatogenesis, and the male hair pattern (Matsumoto, Endocrinol. Met. Clin. N. Am. 23:857-75 (1994)). The endogenous steroidal androgens include testosterone and dihydrotestosterone ("DHT"). Testosterone is the principal steroid secreted by the testes and is the primary circulating androgen found in the plasma of males. Testosterone is converted to DHT by the enzyme 5 alpha-reductase in many peripheral tissues. DHT is thus thought to serve as the intracellular mediator for most androgen actions (Zhou, et al., Molec. Endocrinol. 9:208-18 (1995)). Other steroidal androgens include esters of testosterone, such as the cypionate, propionate, phenylpropionate, cyclopentylpropionate, isocarporate, enanthate, and decanoate esters, and other synthetic androgens such as 7-Methyl-Nortestosterone ("MENT") and its acetate ester (Sundaram et al., "7 Alpha-Methyl-Nortestosterone (MENT): The Optimal Androgen For Male Contraception," Ann. Med., 25:199-205 (1993) ("Sundaram"). Because the AR is involved in male sexual development and function, the AR is a likely target for effecting male contraception or other forms of hormone replacement therapy.

New innovative approaches are urgently needed at both the basic science and clinical levels to develop compounds which are useful for a) male contraception; b) treatment of a variety of hormone-related conditions, for example conditions associated with Androgen Decline in Aging Male (ADAM), such as fatigue, depression, decreased libido, sexual dysfunction, erectile dysfunction, hypogonadism, osteoporosis, hair loss, anemia, obesity, sarcopenia, osteopenia, osteoporosis, benign prostate hyperplasia, alterations in mood and cognition and prostate cancer; c) treatment of conditions associated with ADIF, such as sexual dysfunction, decreased sexual libido, hypogonadism, sarcopenia, osteopenia, osteoporosis, alterations in cognition and mood, depression, anemia, hair loss, obesity, endometriosis, breast cancer, uterine cancer and ovarian cancer; d) treatment and/or prevention of acute and/or chronic muscular wasting conditions; e) preventing and/or treating dry eye conditions; f) oral androgen replacement therapy; and/or g) decreasing the incidence of, halting or causing a regression of prostate cancer.

Polymorphs, solvates and salts of various drugs have been described in the literature as imparting novel properties to the drugs. Organic small drug molecules have a tendency to self-assemble into various polymorphic forms depending on the environment that drives the self assembly. Heat and solvent mediated effects can also lead to changes that transform one polymorphic form into another.

Identifying which polymorphic form is the most stable under each condition of interest and the processes that lead to changes in the polymorphic form is crucial to the design of the drug manufacturing process in order to ensure that the final product is in its preferred polymorphic form. Different polymorphic forms of an active pharmaceutical ingredient (API) can lead to changes in the drug's solubility, dissolution rate, pharmacokinetics and ultimately its bioavailability and efficacy in patients.

SUMMARY OF THE INVENTION

In one embodiment, the present invention relates to solid forms of (R) or (S)—N-(4-cyano-3-(trifluoromethyl)phenyl)-3-(4-cyanophenoxy)-2-hydroxy-2-methylpropanamide and processes of preparation thereof. In some embodiments such compounds are useful for their androgenic and anabolic activity. (R) or (S)—N-(4-cyano-3-(trifluoromethyl)phenyl)-3-(4-cyanophenoxy)-2-hydroxy-2-methylpropanamide are selective androgen receptor modulators (SARMs) useful for a) male contraception; b) treatment of a variety of hormone-related conditions, for example conditions associated with Androgen Decline in Aging Male (ADAM); c) treatment of conditions associated with Androgen Decline in Female (ADIF); d) treatment and/or prevention of chronic muscular wasting; and/or; e) decreasing the incidence of, halting or causing a regression of prostate cancer; f) oral androgen replacement and/or other clinical therapeutic and/or diagnostic areas.

In one embodiment the present invention provides, a crystalline form of (R) or (S)—N-(4-cyano-3-(trifluoromethyl)phenyl)-3-(4-cyanophenoxy)-2-hydroxy-2-methylpropanamide compound.

In one embodiment the present invention provides, an anhydrous crystalline form of (R) or (S)—N-(4-cyano-3-(trifluoromethyl)phenyl)-3-(4-cyanophenoxy)-2-hydroxy-2-methylpropanamide compound.

In another embodiment this invention provides, a composition comprising a therapeutic amount of crystalline form of an anhydrous crystalline form of (R) or (S)—N-(4-cyano-3-(trifluoromethyl)phenyl)-3-(4-cyanophenoxy)-2-hydroxy-2-methylpropanamide and a suitable carrier or diluent.

In one embodiment this invention provides, a process for the preparation of a crystalline form of (R) or (S)—N-(4-cyano-3-(trifluoromethyl)phenyl)-3-(4-cyanophenoxy)-2-hydroxy-2-methylpropanamide said process comprising dissolving (R) or (S)—N-(4-cyano-3-(trifluoromethyl)phenyl)-3-(4-cyanophenoxy)-2-hydroxy-2-methylpropanamide in at least one organic solvent at a temperature of between about −20° C. to +5° C. under conditions permissive to crystallization, thereby obtaining said crystalline form.

In one embodiment, this invention provides, a paracrystalline (R) or (S)—N-(4-cyano-3-(trifluoromethyl)phenyl)-3-(4-cyanophenoxy)-2-hydroxy-2-methylpropanamide compound.

In another embodiment, this invention provides, a composition comprising paracrystalline form of (R) or (S)—N-(4-cyano-3-(trifluoromethyl)phenyl)-3-(4-cyanophenoxy)-2-hydroxy-2-methylpropanamide and a suitable carrier or diluent.

In one embodiment, this invention provides, a process for the preparation of paracrystalline (R) or (S)—N-(4-cyano-3-(trifluoromethyl)phenyl)-3-(4-cyanophenoxy)-2-hydroxy-2-methylpropanamide comprising stirring a suspension of a crystalline form of (R) or (S)—N-(4-cyano-3-(trifluoromethyl)phenyl)-3-(4-cyanophenoxy)-2-hydroxy-2-methylpropanamide in water at ambient temperature of about 20-30° C. for at least 0.5 hours, to obtain a paracrystalline compound.

In one embodiment this invention provides, a composition comprising a mixture of crystalline and paracrystalline solid forms of (R) or (S)—N-(4-cyano-3-(trifluoromethyl)phenyl)-3-(4-cyanophenoxy)-2-hydroxy-2-methylpropanamide compound and a suitable carrier or diluent.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 4A—solid form A-batch P1 of compound S-1; FIG. 4B—solid form A-batch P2 of compound S-1; FIG. 4C—solid form A-batch P3 of compound S-1; FIG. 4D—solid form B'-batch P4 of compound S-1.

FIG. 9A is a DVS of form A. FIG. 9B is a DVS of form A. FIG. 9C is a DVS of form B'.

FIG. 10A—demonstrates XRPD spectra after compound S-1, Form A, suspended in n-heptane, 108 mg/2.0 mL. FIG. 10B—demonstrates XRPD spectra after compound S-1, Form B', suspended in ethyl acetate+n-heptane 1:2 (v/v), 81 mg/1.7 mL. FIG. 10C—demonstrates XRPD spectra after compound S-1, Form B' suspended in ethyl acetate+n-pentane 1:2 (v/v), 101 mg/1.0 mL. FIG. 10D—demonstrates XRPD spectra after compound S-1 Form A, suspended in ethyl acetate+n-pentane 1:2 (v/v), 128 mg/2.0 mL. FIG. 10E-demonstrates XRPD spectra after compound S-1 Form A, suspended in ethyl acetate+n-pentane 1:2 (v/v), 112 mg/2.0 mL. FIG. 10F—demonstrates XRPD spectra after compound S-1 Form A, suspended in methyl acetate+n-pentane 1:2 (v/v), 126 mg/2.0 mL.

FIG. 11A—demonstrates XRPD spectra of compound S-1 in toluene and n-hexane at 23° C. for 2 days. FIG. 11B—shows a superimposed spectra of XRPD of batch P1 (Form A) and the XRPD obtained in FIG. 11A. FIG. 11C—demonstrates XRPD spectra obtained for compound S-1 in acetic acid and water at 23° C. for 7 days. FIG. 11D—shows a superimposed spectra of XRPD of batch P1 (Form A) and the XRPD obtained in FIG. 11B.

FIG. 12A—demonstrates XRPD pattern obtained of compound S-1 (batch P1) in ethyl-acetate solution. FIG. 12B—demonstrates a superimposed spectra of XRPD of batch P1 (Form A) and the XRPD obtained in FIG. 12A. FIG. 12C—demonstrates XRPD pattern obtained of compound S-1 (batch P1) from THF, to provide form C. FIG. 12D—demonstrate XRPD patterns of a mixture of form A (red, top) and form C (blue, bottom), as presented in FIG. 12C.

FIG. 13A—demonstrates XRPD spectra obtained of compound S-1 (batch P1) in ethylacetate+n-heptane 1:1 (v/v). FIG. 13B—shows a superimposed spectra of XRPD of batch P1 (Form A) and the XRPD obtained in FIG. 13A. FIG. 13C—demonstrates XRPD spectra obtained of compound S-1 (batch P1) in acetonitrile+toluene 1:3 v/v. FIG. 13D—shows a superimposed spectra of XRPD of batch P1 (Form A) and the XRPD obtained in FIG. 13 B.

FIG. 14A—demonstrates XRPD spectra obtained of compound S-1 (batch P-1) in 1-4-dioxane and cooled to −50° C. FIG. 14B—shows a superimposed spectra of XRPD of batch P1 (Form A) and the XRPD obtained in FIG. 14A.

FIG. 16A—demonstrates XRPD spectra obtained from a mixture of batches of compound S-1 (P1, P18, P24, P30, P37 and P38, all batches have a XRPD characteristics of Form A) in ethylacetate+n-heptane 1:2 (v/v) 130 mg/2.0 mL. FIG. 16B shows a superimposed spectra of XRPD of batch P1 (Form A) and the XRPD obtained in FIG. 16A. FIG. 16C—demonstrates XRPD spectra obtained from a mixture of batches of compound S-1 (P1 and P52 where batch P1 is Form A and P52 is Form A+C) in ethylacetate+n-heptane 1:2 (v/v); (81+64) mg/2.0 mL. FIG. 16D shows a superimposed spectra of XRPD of batch P1 (Form A) and the XRPD obtained in FIG. 16B.

FIG. 17A—demonstrates the DSC results obtained for compound S-1 batch P1 with no solvent after 11 weeks. FIG. 17B—demonstrates XRPD of compound S-1 batch P1 (form A) in water after 19 h at 37° C., resulting in formation of form B'. FIG. 17C—demonstrates XRPD of compound S-1 batch P1 (form A) in acetic acid+water 1:2 (v/v) after 20 h at 23° C. FIG. 17D—shows a DSC thermogram of heating a sample of form A (black), cooling of the sample after melting (grey) and reheating of the sample (white). Heating rates were 10° C./min while the cooling rate was 1° C./min. Heating form A beyond the melting temperature produces B'' which doesn't revert to A even when the sample is cooled back down to ambient temperature. FIG. 17E—1° C./min DSC runs of form A (grey), B'' (black), mixture of A and D (white) and mixture of B'' and D (dark grey). A and B'' can undergo crystallization to D but only in the presence of D to act as seeds for crystallization. FIG. 17F—DSC graphs for form A stored at ambient temperature/100% RH for 7 days (light grey), 50° C./0% RH for 7 days (dark grey), and 50° C./75% RH for 6 hours (white) along with the DSC graph of the original sample (black). FIG. 17G—(a) DSC graphs of polymorph A seeded with form D and stored at 50° C./75% RH. (b) DSC graphs of form A seeded with form D and stored at 50° C. in water.

DETAILED DESCRIPTION OF THE INVENTION

Figure 1:
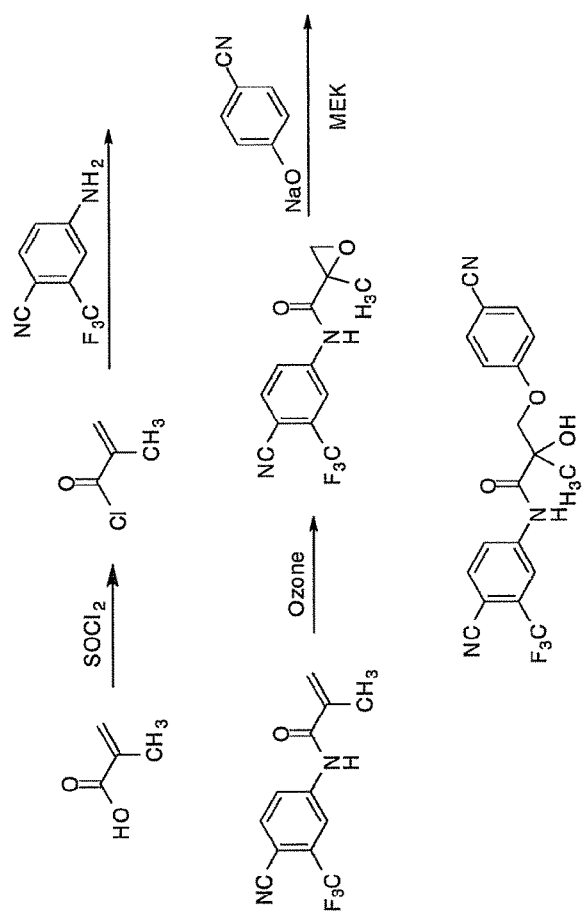
FIG. 1 schematically depicts the synthesis of racemic mixtures of compound 1.
Figure 2:
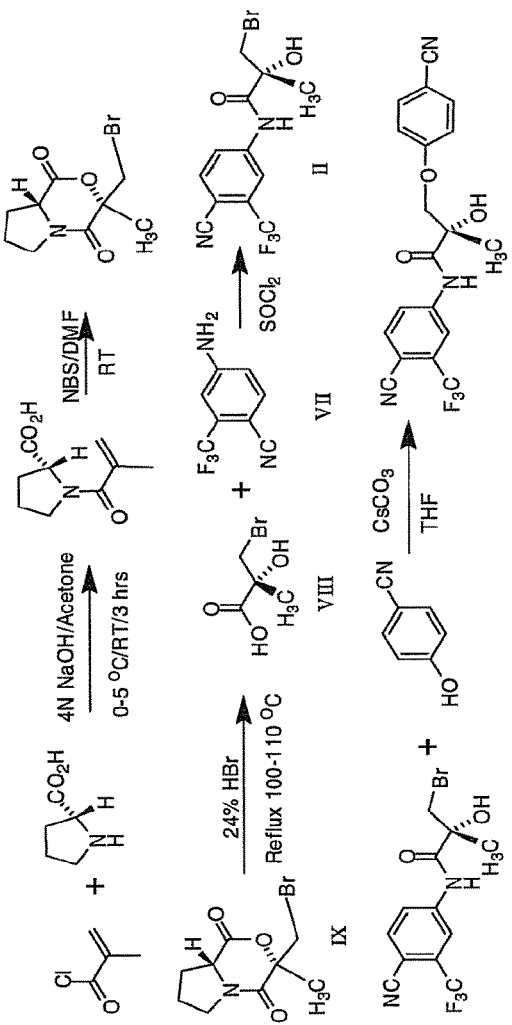
FIG. 2 schematically depicts the synthesis of the (S)-enantiomer of compound S-1.
Figure 3:
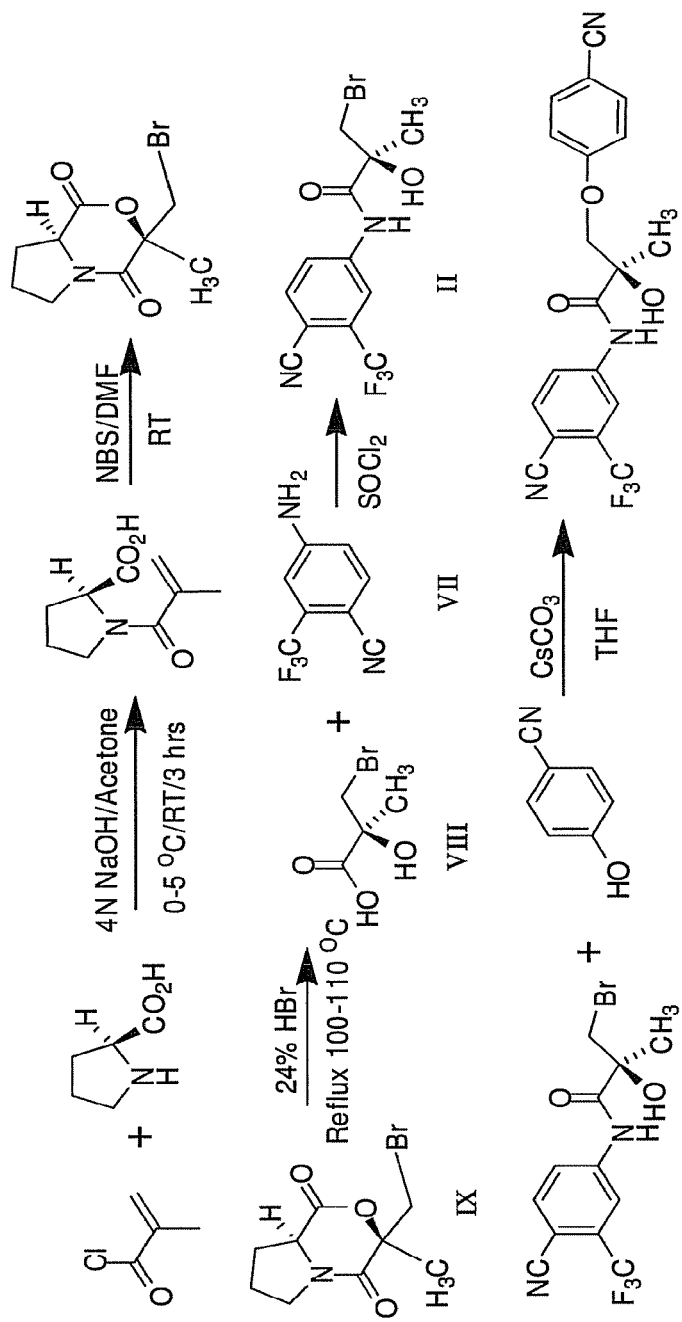
FIG. 3 schematically depicts the synthesis of the (R)-enantiomer of compound R-1.

In some embodiments, the present invention provides solid forms of (R) or (S)—N-(4-cyano-3-(trifluoromethyl) phenyl)-3-(4-cyanophenoxy)-2-hydroxy-2-methylpropanamide and processes of preparation of the same. This invention also provides pharmaceutical compositions comprising the solid forms of (R) or (S)—N-(4-cyano-3-(trifluoromethyl)phenyl)-3-(4-cyanophenoxy)-2-hydroxy-2-methyl propanamide, and uses thereof.

(R) or (S)—N-(4-cyano-3-(trifluoromethyl)phenyl)-3-(4-cyanophenoxy)-2-hydroxy-2-methylpropanamide are androgen receptor targeting agents (ARTA), which demonstrate androgenic and anabolic activity. In some embodiments, the methyl propionamides as herein described are selective androgen receptor modulators (SARM), which in some embodiments are useful for a) male contraception; b) treatment of a variety of hormone-related conditions, for example conditions associated with Androgen Decline in Aging Male (ADAM), such as fatigue, depression, decreased libido, sexual dysfunction, erectile dysfunction, hypogonadism, osteoporosis, hair loss, anemia, obesity, sarcopenia, osteopenia, osteoporosis, benign prostate hyperplasia, alterations in mood and cognition and prostate cancer; c) treatment of conditions associated with Androgen Decline in Female (ADIF), such as sexual dysfunction, decreased sexual libido, hypogonadism, sarcopenia, osteopenia, osteoporosis, alterations in cognition and mood, depression, anemia, hair loss, obesity, endometriosis, breast cancer, uterine cancer and ovarian cancer; d) treatment and/or prevention of chronic muscular wasting; e) decreasing the incidence of, halting or causing a regression of prostate cancer; f) oral androgen replacement and/or other clinical therapeutic and/or diagnostic areas.

In some embodiments, this invention provides polymorphic solid forms of (R) or (S)—N-(4-cyano-3-(trifluoromethyl)phenyl)-3-(4-cyanophenoxy)-2-hydroxy-2-methylpropanamide compounds of this invention. In one embodiment the term "polymorph" refers to a specific form of the SARM compounds of this invention, for example, polymorphs may represent crystalline forms that can vary in pharmaceutically relevant physical properties between one form and another, for example under different crystallization conditions, environmental conditions, hygroscopic activity of the compounds, etc.

In one embodiment, this invention provides, a crystalline form of (R) or (S)—N-(4-cyano-3-(trifluoromethyl)phenyl)-3-(4-cyanophenoxy)-2-hydroxy-2-methylpropanamide compound.

In one embodiment, this invention provides, a crystalline form of anhydrous (R) or (S)—N-(4-cyano-3-(trifluoromethyl)phenyl)-3-(4-cyanophenoxy)-2-hydroxy-2-methylpropanamide compound.

In one embodiment, this invention provides, a crystalline form of anhydrous (S)—N-(4-cyano-3-(trifluoromethyl) phenyl)-3-(4-cyanophenoxy)-2-hydroxy-2-methylpropanamide compound.

In another embodiment, the crystalline form of (S)—N-(4-cyano-3-(trifluoromethyl)phenyl)-3-(4-cyanophenoxy)-2-hydroxy-2-methylpropanamide (compound S-1), is characterized by:
    a. an X-Ray Powder diffraction pattern comprising peaks at °2θ (d value Å) angles of about 5.6 (15.9), 7.5 (11.8), 8.6 (10.3), 9.9 (8.9), 12.4 (7.1), 15.0 (5.9), 16.7 (5.3), 17.3 (5.1), 18.0 (4.9), 18.5 (4.8), 19.3 (4.6), 19.8 (4.5), 20.6 (4.3), 21.8 (4.1), 22.3 (4.0), 23.4 (3.8), 23.9 (3.7), 24.6 (3.6), 24.9 (3.6), 25.4 (3.5), 26.0 (3.4), 26.5 (3.4), 27.8 (3.2); and
    b. a melting point of about 80° C.

According to this aspect and in another embodiment, such a crystalline form of compound S-1, having all or part of the characteristics listed in (a) and (b) is referred to herein as crystalline Form A.

In another embodiment, the solubility of Form A in water is between 20-30 mg/L at 22° C. In another embodiment, the solubility of Form A in water is between 23-27 mg/L at 22° C.

In one embodiment, this invention provides a crystalline form of an (R)—N-(4-cyano-3-(trifluoromethyl)phenyl)-3-(4-cyanophenoxy)-2-hydroxy-2-methylpropanamide (compound R-1), wherein said crystalline form is obtained by methods similar to that of the S isomer, as described herein. In some embodiments, such a crystalline form of compound R-1, is structurally related and/or possesses similar characteristics to that of compound S-1.

In one embodiment this invention provides a paracrystalline (R) or (S)—N-(4-cyano-3-(trifluoromethyl)phenyl)-3-(4-cyanophenoxy)-2-hydroxy-2-methylpropanamide compound.

In one embodiment this invention provides a paracrystalline (S)—N-(4-cyano-3-(trifluoromethyl)phenyl)-3-(4-cyanophenoxy)-2-hydroxy-2-methylpropanamide compound.

In one embodiment, the paracrystalline form of (S)—N-(4-cyano-3-(trifluoromethyl)phenyl)-3-(4-cyanophenoxy)-2-hydroxy-2-methylpropanamide (compound S-1) is characterized by:
a. an X-Ray Powder diffraction pattern displaying a broad halo with two harmonic peaks between 15-25 °2θ and
b. a glass transition point of about 55° C.

According to this aspect and in another embodiment, such a paracrystalline form of compound S-1, having all or part of the characteristics listed in (a) and (b) is referred herein as paracrystalline form B'.

In one embodiment the term "paracrystalline" refers to the state of material exhibiting short-range order without long-range order such as liquid crystals or other type of lamellar structures. In one embodiment, the paracrystalline form is a liquid crystal. In another embodiment, the Form B' of compound S-1 is a paracrystalline. In another embodiment, form A of S-1 may convert in whole or in part to paracrystalline Form B' of S-1.

In another embodiment, the solubility of Form B' in water is between 20-30 mg/L at 22° C. In another embodiment, the solubility of Form B' in water is between 23-27 mg/L at 22° C.

In one embodiment, this invention provides an paracrystalline form B" of (S)—N-(4-cyano-3-(trifluoromethyl)phenyl)-3-(4-cyanophenoxy)-2-hydroxy-2-methylpropanamide, characterized by:
a. an X-Ray Powder diffraction pattern displaying a broad halo with two harmonic peaks between 15-25 °2θ and
b. a glass transition point of about 55° C.

In one embodiment, this invention provides a crystalline Form C of (S)—N-(4-cyano-3-(trifluoromethyl)phenyl)-3-(4-cyanophenoxy)-2-hydroxy-2-methylpropanamide characterized by:
a. an X-Ray Powder diffraction pattern comprising unique peaks at °2θ (d value Å) angles of about 6.9 (12.8), 9.5 (9.3), 13.5 (6.6), 16.0 (5.6), 22.8 (3.9).

In another embodiment, crystalline Form C of compound S-1 is obtained as a mixture of Form A and C, by evaporating A out of THF.

In one embodiment, this invention provides a crystalline Form D of (S)—N-(4-cyano-3-(trifluoromethyl)phenyl)-3-(4-cyanophenoxy)-2-hydroxy-2-methylpropanamide characterized by:
a. an X-Ray powder diffraction pattern comprising unique peaks at °2θ (d value Å) angles of about 4.4 (19.9), 8.5 (10.4), 8.8 (10.0), 11.3 (7.8), 12.7 (6.9), 13.8 (6.4), 14.4 (6.1), 14.6 (6.0), 15.1 (5.8), 16.1 (5.5), 16.6 (5.3), 16.9 (5.2), 18.0 (4.9), 18.7 (4.7), 19.0 (4.6), 19.4 (4.55), 20.8 (4.25), 22.1 (4.0), 22.7 (3.9), 23.1 (3.8), 23.4 (3.8), 24.7 (3.6), 24.9 (3.56), 25.3 (3.51), 27.8 (3.2), 29.3 (3.0); and
b. a melting point of about 130° C.

In another embodiment, crystalline Form D of compound S-1 is stable at 50° C./75% RH (Relative Humidity) as well as the other conditions of ambient/75% RH, ambient/100% RH, 30° C./75% RH and 50° C./0% RH.

In another embodiment the characteristics of the different solid forms of S-1 are presented in Example 2 and FIG. 4-FIG. 20.

Solid forms of this invention can be analysed by any method known in the art for example and in one embodiment, X-ray powder diffraction. In another embodiment analysis of the solid forms of this invention may comprise Raman Spectroscopy. In another embodiment analysis of the solid forms of this invention may comprise TG-FTIR (thermo gravimetric fourier transform infrared). In another embodiment analysis of the solid forms of this invention may comprise FT-Raman (fourier transform-Raman). In another embodiment analysis of the solid forms of this invention may comprise DSC (differential scanning calorimetry). In another embodiment analysis of the solid forms of this invention may comprise DVS (dynamic vapor sorption). In another embodiment analysis of the solid forms of this invention may comprise SEM (Scanning electron microscopy).

In one embodiment, this invention provides a polymorphic mixture comprising crystalline forms A and B' in a ratio of between about 95:5 to 85:15, respectively. In another embodiment, the ratio is between about 85:15 to 75:25, respectively. In another embodiment, the ratio is between about 75:25 to 65:35, respectively. In another embodiment, the ratio is between about 95:5 to 90:10, respectively. In another embodiment, the ratio is between about 90:10 to 85:15, respectively. In another embodiment, the ratio is between about 97:3 to 93:7, respectively. In another embodiment, the ratio is between about 85:15 to 80:20. In another embodiment, the ratio is between about 70:20 to 60:20. In another embodiment, the ratio is 50:50, respectively.

In one embodiment, this invention provides a polymorphic mixture comprising crystalline forms A, B' and C in a ratio of between about 90:5:5 to 80:10:10, respectively. In another embodiment, the ratio is between about 80:10:10 to 75:15:10, respectively. In another embodiment, the ratio is between about 95:3:2 to 90:7:3, respectively. In another embodiment, the ratio is between about 75:15:10 to 65:20:15. In another embodiment, the ratio is between about 70:20:10 to 60:20:20.

In one embodiment, this invention provides a polymorphic mixture comprising crystalline forms A, B' and D in a ratio of between about 5:5:90 to 10:10:80, respectively. In another embodiment, the ratio is between about 10:10:80 to 10:15:75, respectively. In another embodiment, the ratio is between about 2:3:95 to 3:7:90, respectively. In another embodiment, the ratio is between about 10:15:75 to 15:20:65. In another embodiment, the ratio is between about 10:20:70 to 20:20:60.

In one embodiment, this invention provides a polymorphic mixture comprising crystalline forms A and C in a ratio of between about 98:2 to 95:5, respectively. In one embodiment, this invention provides a polymorphic mixture comprising crystalline forms A and C in a ratio of between about 95:5 to 90:10, respectively. In one embodiment, this invention provides a polymorphic mixture comprising crystalline forms A and C in a ratio of between about 90:10 to 85:15, respectively. In one embodiment, this invention provides a polymorphic mixture comprising crystalline forms A, and C in a ratio of between about 85:15 to 80:20, respectively. In one embodiment, this invention provides a polymorphic mixture comprising crystalline forms A, and C in a ratio of about 50:50, respectively.

In one embodiment, this invention provides a polymorphic mixture comprising crystalline forms A and D in a ratio of between about 2:98 to 5:95, respectively. In one embodiment, this invention provides a polymorphic mixture comprising crystalline forms A and D in a ratio of between about 5:95 to 10:90, respectively. In one embodiment, this invention provides a polymorphic mixture comprising crystalline forms A and D in a ratio of between about 10:90 to 15:85, respectively. In one embodiment, this invention provides a polymorphic mixture comprising crystalline forms A, and D in a ratio of between about 15:85 to 20:80, respectively. In one embodiment, this invention provides a polymorphic mixture comprising crystalline forms A, and D in a ratio of about 50:50, respectively.

In one embodiment, this invention provides a polymorphic mixture comprising crystalline forms B' and D in a ratio of between about 2:98 to 5:95, respectively. In one embodiment, this invention provides a polymorphic mixture comprising crystalline forms B' and D in a ratio of between about 5:95 to 10:90, respectively. In one embodiment, this invention provides a polymorphic mixture comprising crystalline forms B' and D in a ratio of between about 10:90 to 15:85, respectively. In one embodiment, this invention provides a polymorphic mixture comprising crystalline forms B', and D in a ratio of between about 15:85 to 20:80, respectively. In one embodiment, this invention provides a polymorphic mixture comprising crystalline forms B', and D in a ratio of about 50:50, respectively.

In one embodiment, this invention provides a polymorphic mixture comprising crystalline forms B' and C in a ratio of between about 98:2 to 95:5, respectively. In one embodiment, this invention provides a polymorphic mixture comprising crystalline forms B' and C in a ratio of between about 95:5 to 90:10, respectively. In one embodiment, this invention provides a polymorphic mixture comprising crystalline forms B' and C in a ratio of between about 90:10 to 85:15, respectively. In one embodiment, this invention provides a polymorphic mixture comprising crystalline forms B' and C in a ratio of between about 85:15 to 80:20, respectively. In one embodiment, this invention provides a polymorphic mixture comprising crystalline forms B' and C in a ratio of about 50:50, respectively.

In another embodiment, the ratio between crystalline form A to crystalline form B' is between about 95:5 to 85:15. In another embodiment, the ratio between crystalline form A to crystalline form B' is between about 98:2 to 95:5. In another embodiment, the ratio between crystalline form A to crystalline form B' is between about 85:15 to 75:25. In another embodiment, the ratio between crystalline form A to crystalline form B' is between about 75:25 to 65:35 respectively.

In one embodiment a sample of (S)—N-(4-cyano-3-(trifluoromethyl)phenyl)-3-(4-cyanophenoxy)-2-hydroxy-2-methylpropanamide may comprise a mixture of solid form A, B', B", C and D. In another embodiment the percentage of several solid forms in a sample (for example the percentage of solid form A and B in a sample) can be determined by running a Modulated DSC (Differential Scanning Calorimetry) at a heating rate of 3° C./min. from 10° C. to 130° C., followed by linear integration of the solid form A and/or solid form B to obtain the enthalpy of each.

In one embodiment the solid form of a SARM compound can influence its bioavailability, stability, processability and ease of manufacture and uses thereof are to be considered part of this invention.

In one embodiment, this invention provides a process for the preparation of a crystalline form of (R) or (S)—N-(4-cyano-3-(trifluoromethyl)phenyl)-3-(4-cyanophenoxy)-2-hydroxy-2-methylpropanamide comprising dissolving amorphous (R) or (S)—N-(4-cyano-3-(trifluoromethyl)phenyl)-3-(4-cyanophenoxy)-2-hydroxy-2-methylpropanamide in at least one organic solvent at a temperature of between about −20° C. to +30° C. under conditions permissive to crystallization, thereby obtaining the crystalline form.

In one embodiment, this invention provides a process for the preparation of a crystalline form A of (S)—N-(4-cyano-3-(trifluoromethyl)phenyl)-3-(4-cyanophenoxy)-2-hydroxy-2-methylpropanamide comprising dissolving amorphous (S)—N-(4-cyano-3-(trifluoromethyl)phenyl)-3-(4-cyanophenoxy)-2-hydroxy-2-methylpropanamide in at least one organic solvent at a temperature of between about −20° C. to +30° C. under conditions permissive to crystallization, thereby obtaining the crystalline form.

In another embodiment, the temperature for crystallization of (S)—N-(4-cyano-3-(trifluoromethyl)phenyl)-3-(4-cyanophenoxy)-2-hydroxy-2-methylpropanamide, is about 5° C. In another embodiment, the temperature is of about −20° C. In another embodiment, the temperature is of about 20° C. In another embodiment, the temperature is between about 20 to 50° C. In another embodiment, the temperature is about −10 to 0° C. In another embodiment, the temperature is about 0 to 5° C. In another embodiment, the temperature is about −10 to −20° C.

In another embodiment, form A of (S)—N-(4-cyano-3-(trifluoromethyl)phenyl)-3-(4-cyanophenoxy)-2-hydroxy-2-methylpropanamide (compound S-1) is prepared by crystallization from an organic solvent comprising a mixture of solvents. In another embodiment the mixture comprises two solvents in a 1:2 v/v ratio, respectively. In another embodiment the mixture comprises two solvents in a 1:3 v/v ratio, respectively. In another embodiment the mixture comprises two solvents in a 1:4 v/v ratio, respectively. In another embodiment the mixture comprises ethyl formate and pentane in a 1:2 v/v ratio, respectively. In another embodiment, the mixture comprises methyl acetate and pentane in a 1:2 v/v ratio, respectively. In another embodiment the mixture comprises ethylacetate and n-hexane. In another embodiment the mixture comprises toluene and n-hexane. In another embodiment the mixture comprises dichloromethane and n-hexane. In another embodiment the mixture comprises acetic acid and water in a 1:2 v/v ratio. In another embodiment, form A is prepared by crystallization from a solvent/antisolvent mixture at ambient temperature. In another embodiment, ethyl acetate, ethanol, dichloromethane or acetonitrile are the solvents and n-hexane, n-pentane, n-heptane and cyclohexane etc. are used as antisolvents. In another embodiment the solvent/antisolvent ratios are between 1:2 and 1:3.

In another embodiment, the crystalline form A of compound S-1 is prepared by forming a suspension of a paracrystalline form of compound of formula S-1 in a solvent/antisolvent mixture. In another embodiment solid form A is prepared by forming a suspension of a paracrystalline form of compound of formula S-1 in ethylacetate and heptane mixture in a 1:2 v/v ratio, respectively. In another embodiment, solid form A is prepared by forming a suspension of a paracrystalline form of compound of formula S-1 in a mixture of ethylacetate and pentane in a 1:2 v/v ratio, respectively. In another embodiment, the crystalline form A of compound S-1 is prepared by forming a suspension of form B' in a solvent/antisolvent mixture at concentrations above the saturation limit at 23° C. for several hours followed by drying to obtain form A.

In another embodiment, form D of (S)—N-(4-cyano-3-(trifluoromethyl)phenyl)-3-(4-cyanophenoxy)-2-hydroxy-2-methylpropanamide (compound S-1) is prepared by crystallization from solvent/antisolvent mixture at 50° C. using ethyl acetate and cyclohexane as the solvent and antisolvents, respectively. In another embodiment, form D is prepared from other polymorphic forms by "seeding" the sample with a small amount of D and storing it at 110° C./0% RH for 7 days or at 50° C. in water for 24 hours followed by drying. In another embodiment, heating forms A and/or B" to 110° C. in the presence of D causes the A and B" forms to rearrange into form D. In another embodiment, form D in the presence of moisture acts as the seed for the crystallization process and drives the transformation of forms A and B' into D.

Figure 17A:
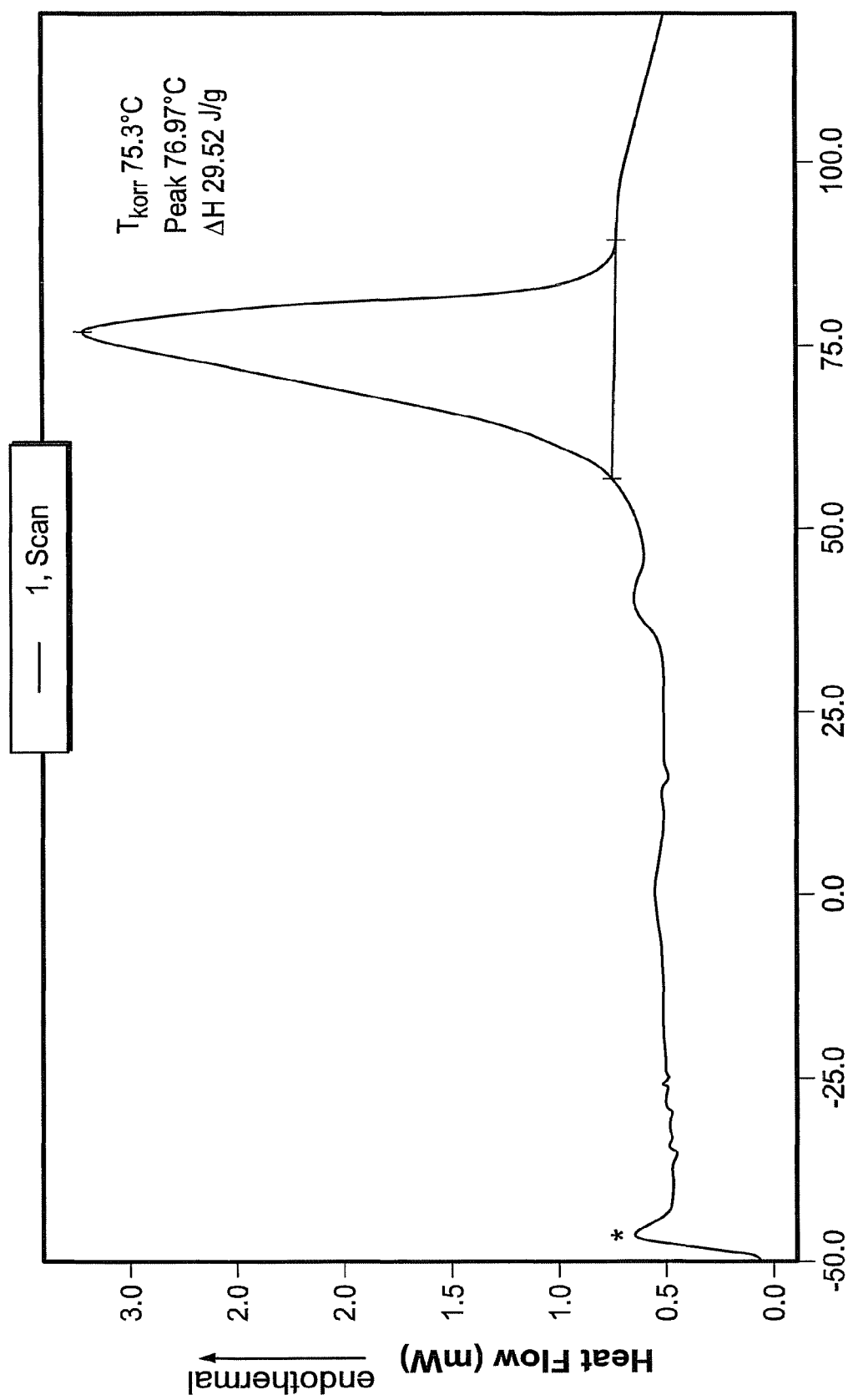
FIG. 17A-FIG. 17G provides a DSC thermogram and XRPD pattern, representing the results of water vapor sorption where S-1 (batch P1) was stored in a glass tube under 96% r.h (relative humidity) at room temperature.
Figure 17B:
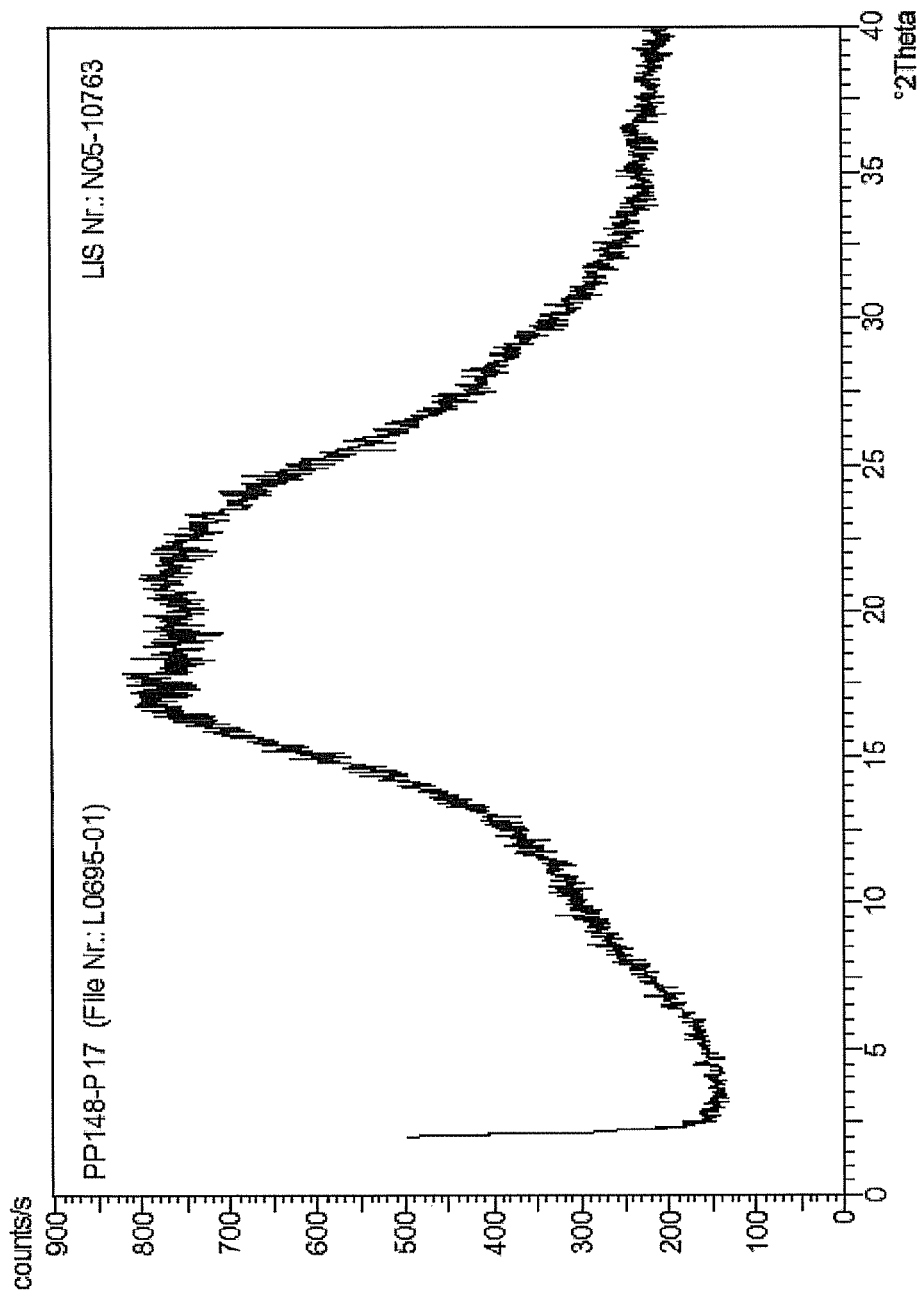
Figure 17C:
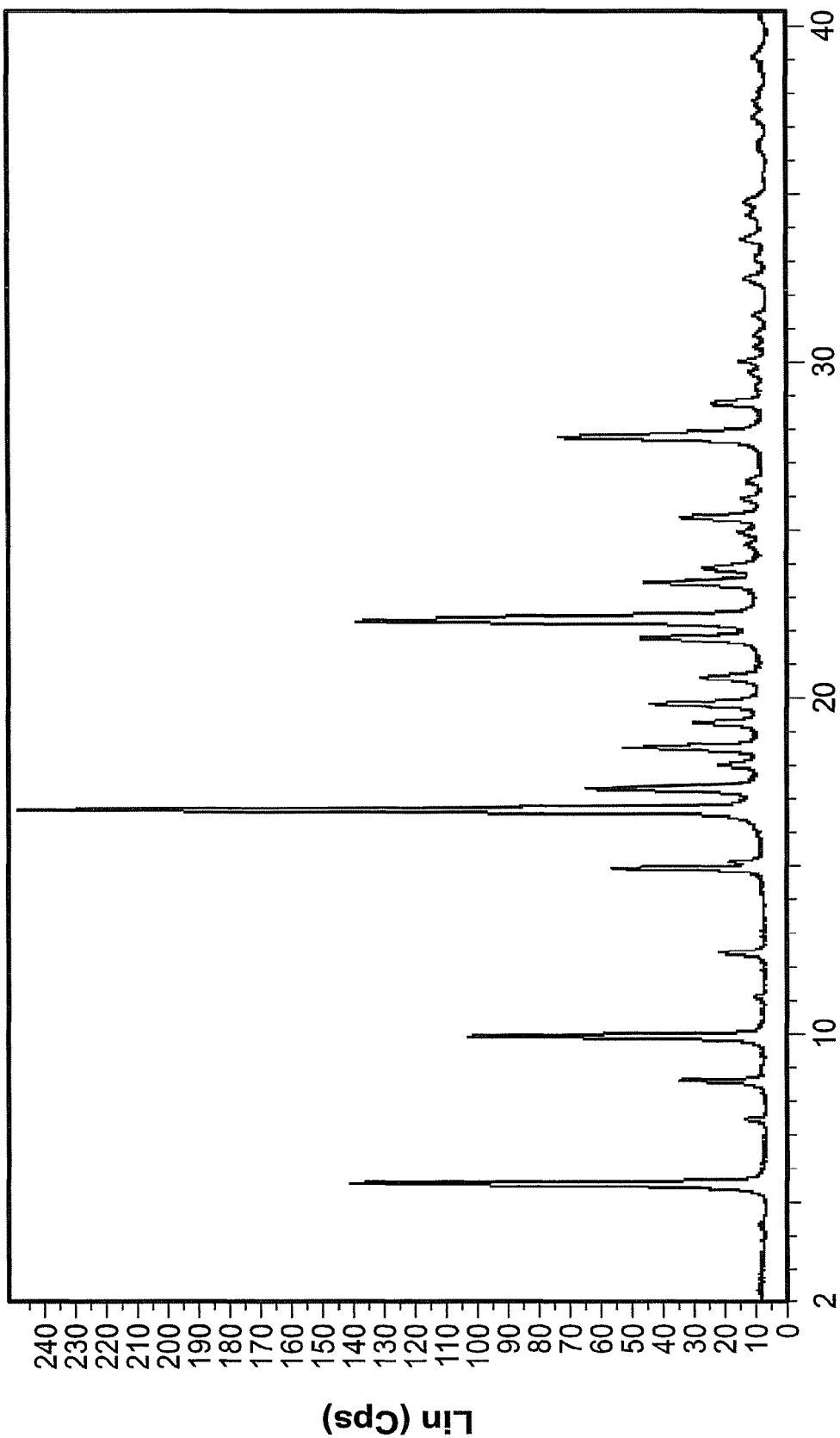
Figure 17D:
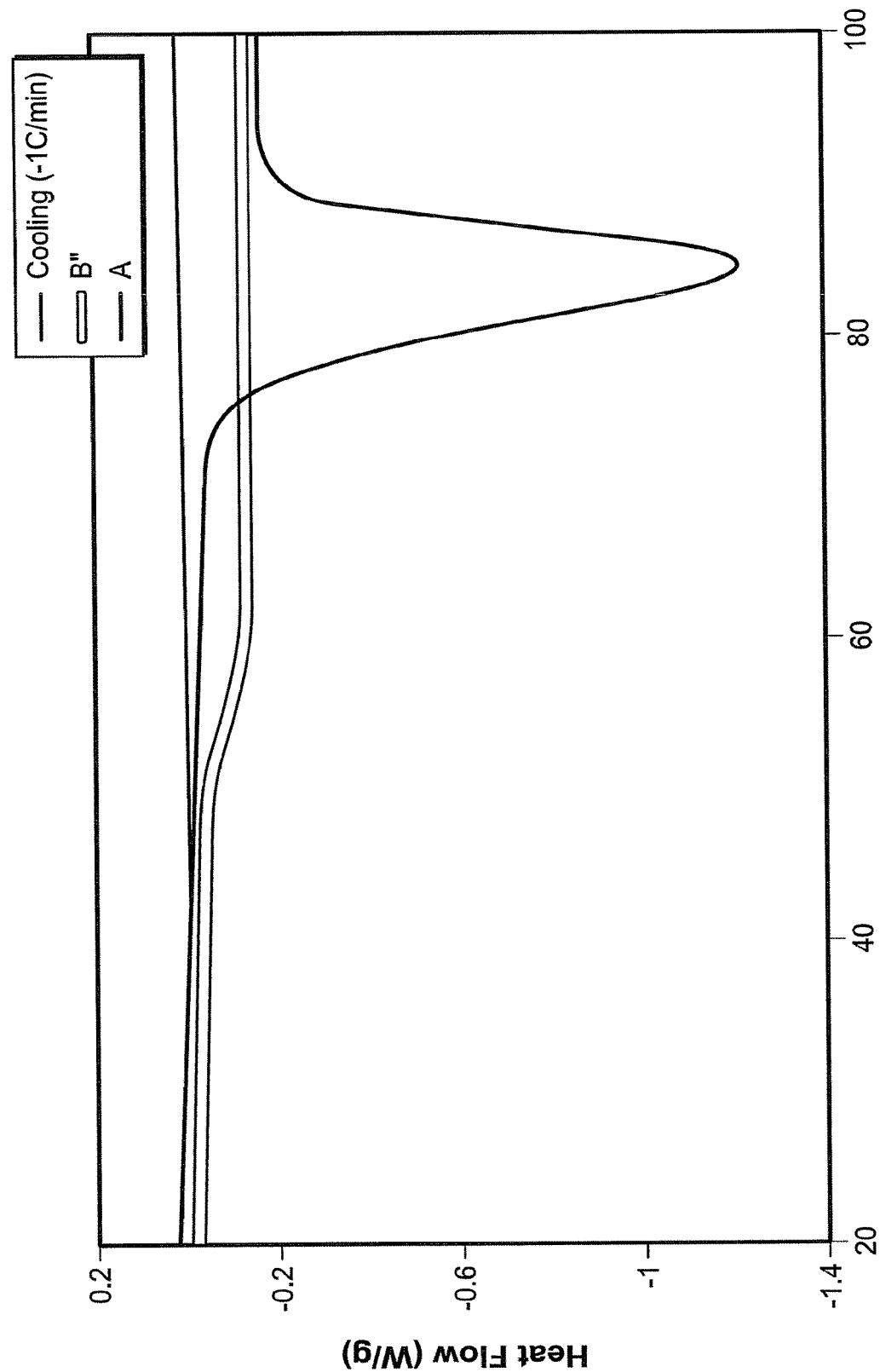
Figure 17E:
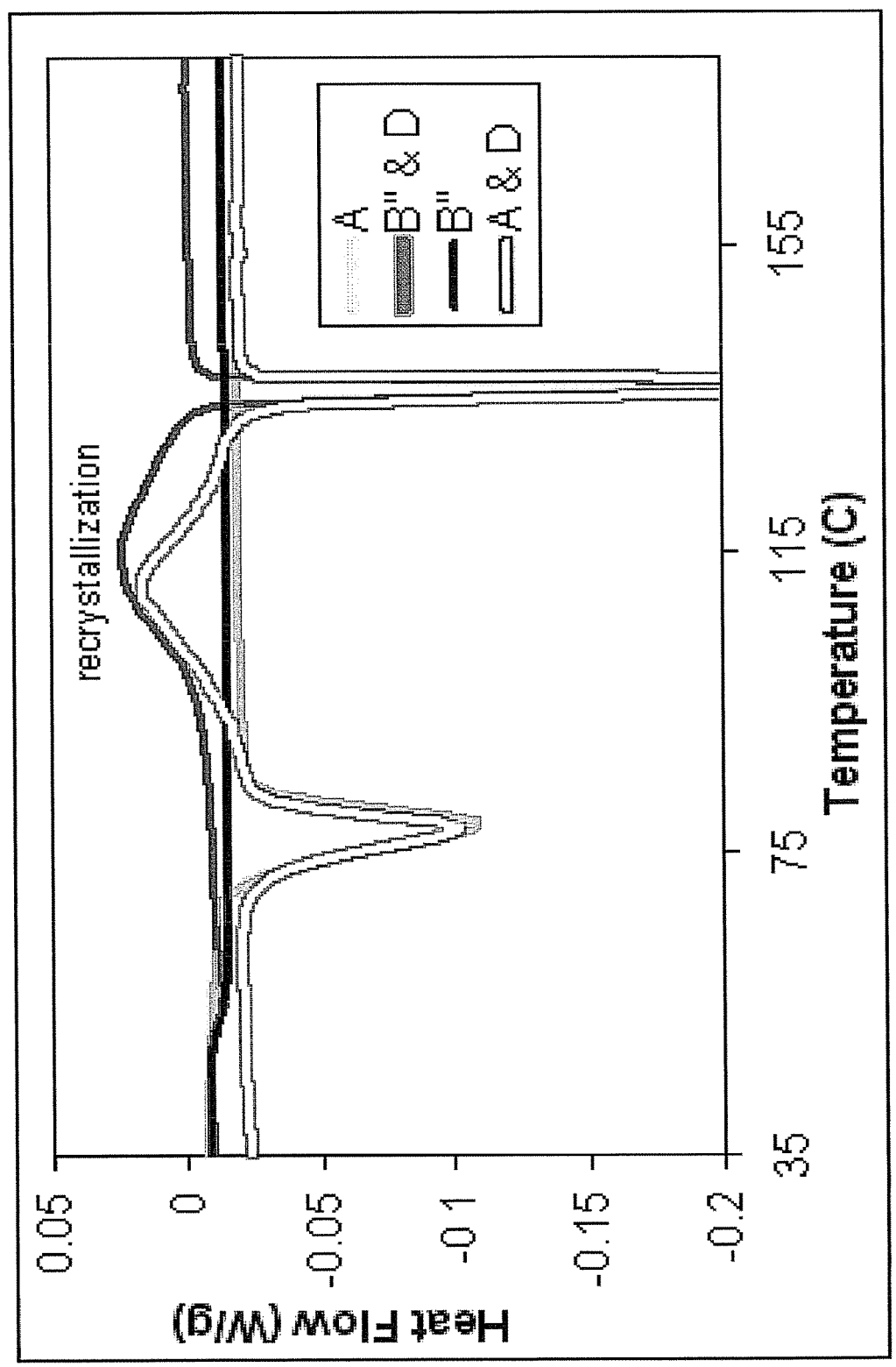
Figure 17F:
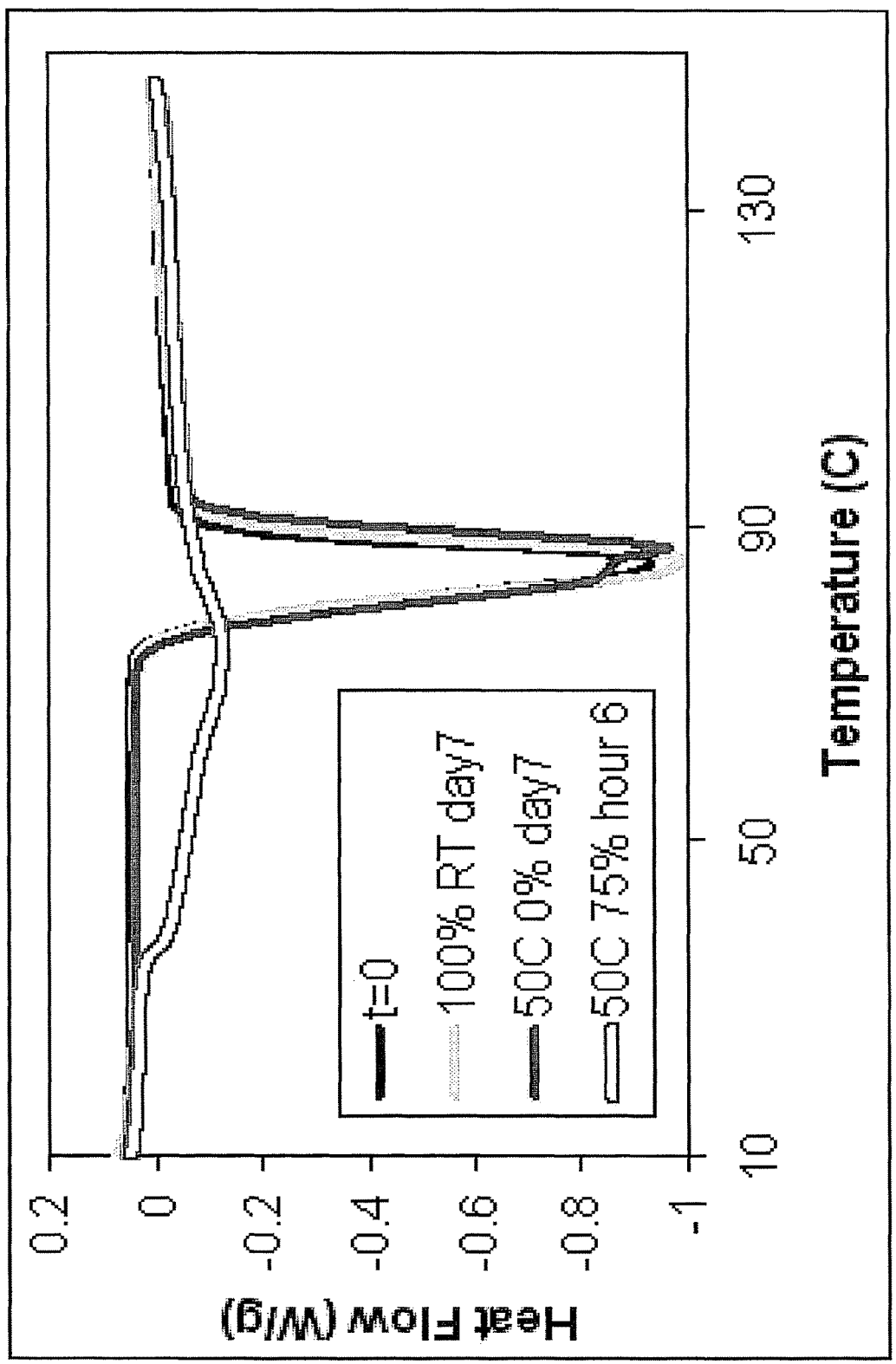
Figure 17G:
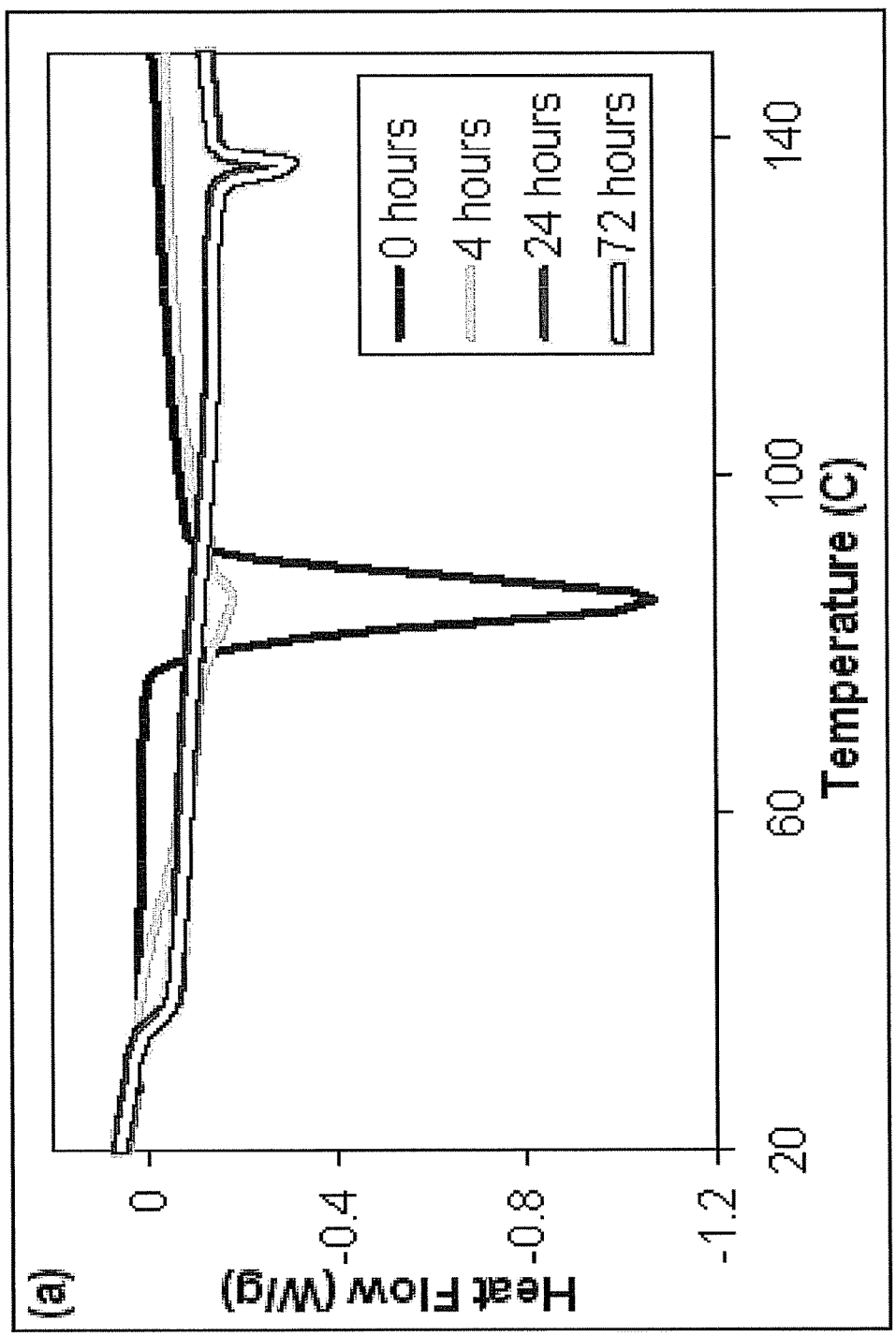
Figure 17G:
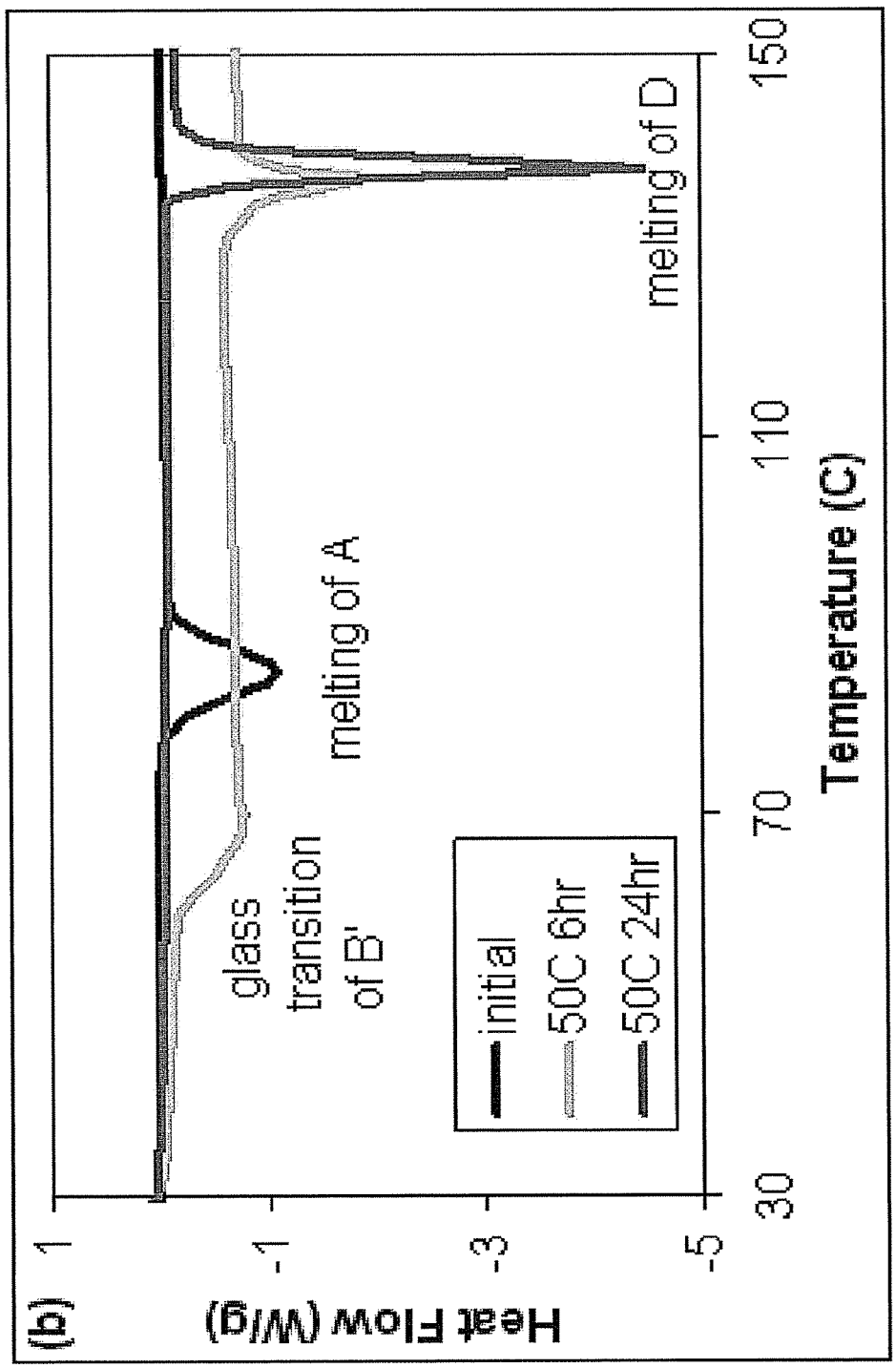

In another embodiment, FIG. 17G shows the time evolution of polymorph A seeded with a small amount of D at 50° C./75% RH. The amount of polymorph D initially added to the sample is very small that it isn't detectable by the DSC with heating rate of 10° C./min. After 24 hours, most of the polymorph form A has been converted to B' but a small amount of sample has also been converted to D and the amount of sample in D increases over time. The transformation process is speeded up in FIG. 17G by storing the sample in water at 50° C. Form A has been converted to both B' and D after 6 hours but the sample is predominantly in form D by 24 hours.

In one embodiment this invention provides a process for the preparation of paracrystalline (R) or (S)—N-(4-cyano-3-(trifluoromethyl)phenyl)-3-(4-cyanophenoxy)-2-hydroxy-2-methylpropanamide comprising stirring a suspension of a crystalline form of (R) or (S)—N-(4-cyano-3-(trifluoromethyl)phenyl)-3-(4-cyanophenoxy)-2-hydroxy-2-methylpropanamide in water at ambient temperature of about 20-30° C. for at least 0.5 hours, to obtain a paracrystalline compound.

In one embodiment this invention provides a process for the preparation of paracrystalline form B' of (S)—N-(4-cyano-3-(trifluoromethyl)phenyl)-3-(4-cyanophenoxy)-2-hydroxy-2-methylpropanamide comprising stirring a suspension of a crystalline form of (S)—N-(4-cyano-3-(trifluoromethyl)phenyl)-3-(4-cyanophenoxy)-2-hydroxy-2-methylpropanamide in water at ambient temperature of about 20-30° C. for at least 0.5 hours, to obtain a paracrystalline compound.

In one embodiment this invention provides a process for the preparation of paracrystalline form B' of (S)—N-(4-cyano-3-(trifluoromethyl)phenyl)-3-(4-cyanophenoxy)-2-hydroxy-2-methylpropanamide comprising stirring a suspension of a crystalline form A of (S)—N-(4-cyano-3-(trifluoromethyl)phenyl)-3-(4-cyanophenoxy)-2-hydroxy-2-methylpropanamide in water at ambient temperature of about 20-30° C. for at least 0.5 hours, to obtain a paracrystalline compound. In another embodiment, paracrystalline form B' is prepared by stirring a suspension of crystalline form A at 50° C. in water for 24 h. In another embodiment paracrystalline form B' is prepared by stirring a suspension of crystalline form A at 37° C. overnight to obtain paracrystalline form B'.

In one embodiment solid form B' of (S)—N-(4-cyano-3-(trifluoromethyl)phenyl)-3-(4-cyanophenoxy)-2-hydroxy-2-methylpropanamide is prepared by storage of solid form A at 40° C. and 75% relative humidity (r.h.) for 1-2 h. In another embodiment, solid form A is stored at 40° C. and 75% r.h. for 2-4 h. In another embodiment, solid form A is stored at 40° C. and 75% r.h. for 4-10 h. In another embodiment, solid form A is stored at 40° C. and 75% r.h. for 10-15 h. In another embodiment, solid form A is stored at 40° C. and 75% r.h. for 15-24 h. In another embodiment, solid form A is stored at 40° C. and 75% r.h. for 24 h. In another embodiment, solid form A is stored at 40° C. and 75% r.h. for 30 days.

In one embodiment solid form B' of (S)—N-(4-cyano-3-(trifluoromethyl)phenyl)-3-(4-cyanophenoxy)-2-hydroxy-2-methylpropanamide is prepared by storage of solid form A at 40° C. and 75% relative humidity (r.h.). In another embodiment, solid form A is stored at a temperature range of about of 30-40° C. and relative humidity range of about 50-75%. In another embodiment, solid form A is stored at a temperature range of about of 40-50° C. and a relative humidity of about 60-80%. In another embodiment, solid form A is stored at a temperature range of about 40-50° C. and a relative humidity of about 60-80%.

In one embodiment, form B' is assigned as a lyotropic liquid crystalline form due to its solvent mediated formation.

In one embodiment liquid crystalline form B" of (S)—N-(4-cyano-3-(trifluoromethyl)phenyl)-3-(4-cyanophenoxy)-2-hydroxy-2-methylpropanamide is prepared by melting or heating solid form A of (S)—N-(4-cyano-3-(trifluoromethyl)phenyl)-3-(4-cyanophenoxy)-2-hydroxy-2-methylpropanamide to 80° C. followed by cooling.

In one embodiment form B" of (S)—N-(4-cyano-3-(trifluoromethyl)phenyl)-3-(4-cyanophenoxy)-2-hydroxy-2-methylpropanamide is prepared by melting or heating to 130° C. solid form D of (S)—N-(4-cyano-3-(trifluoromethyl)phenyl)-3-(4-cyanophenoxy)-2-hydroxy-2-methylpropanamide followed by cooling.

In one embodiment, evaporation of (S)—N-(4-cyano-3-(trifluoromethyl)phenyl)-3-(4-cyanophenoxy)-2-hydroxy-2-methylpropanamide from solvents such as ethanol without an antisolvent yield form B".

In one embodiment, form B" is assigned as a thermotropic liquid crystalline form from its thermal method of preparation.

In one embodiment this invention provides a process for the preparation of solid form C of (S)—N-(4-cyano-3-(trifluoromethyl)phenyl)-3-(4-cyanophenoxy)-2-hydroxy-2-methylpropanamide comprising dissolving crystalline form A of (S)—N-(4-cyano-3-(trifluoromethyl)phenyl)-3-(4-cyanophenoxy)-2-hydroxy-2-methylpropanamide in THF, followed by evaporation to obtain solid form C.

In another embodiment, form C is obtained as a mixture with form A.

In one embodiment this invention provides a process for the preparation of toluene solvate solid form of (S)—N-(4-cyano-3-(trifluoromethyl)phenyl)-3-(4-cyanophenoxy)-2-hydroxy-2-methylpropanamide comprising using any solvent/antisolvent crystallization method that uses toluene as the antisolvent.

In another embodiment, the toluene solvate solid form has a melting point about 100° C. with the enthalpy of melting 70±5 J/g.

Figure 20:
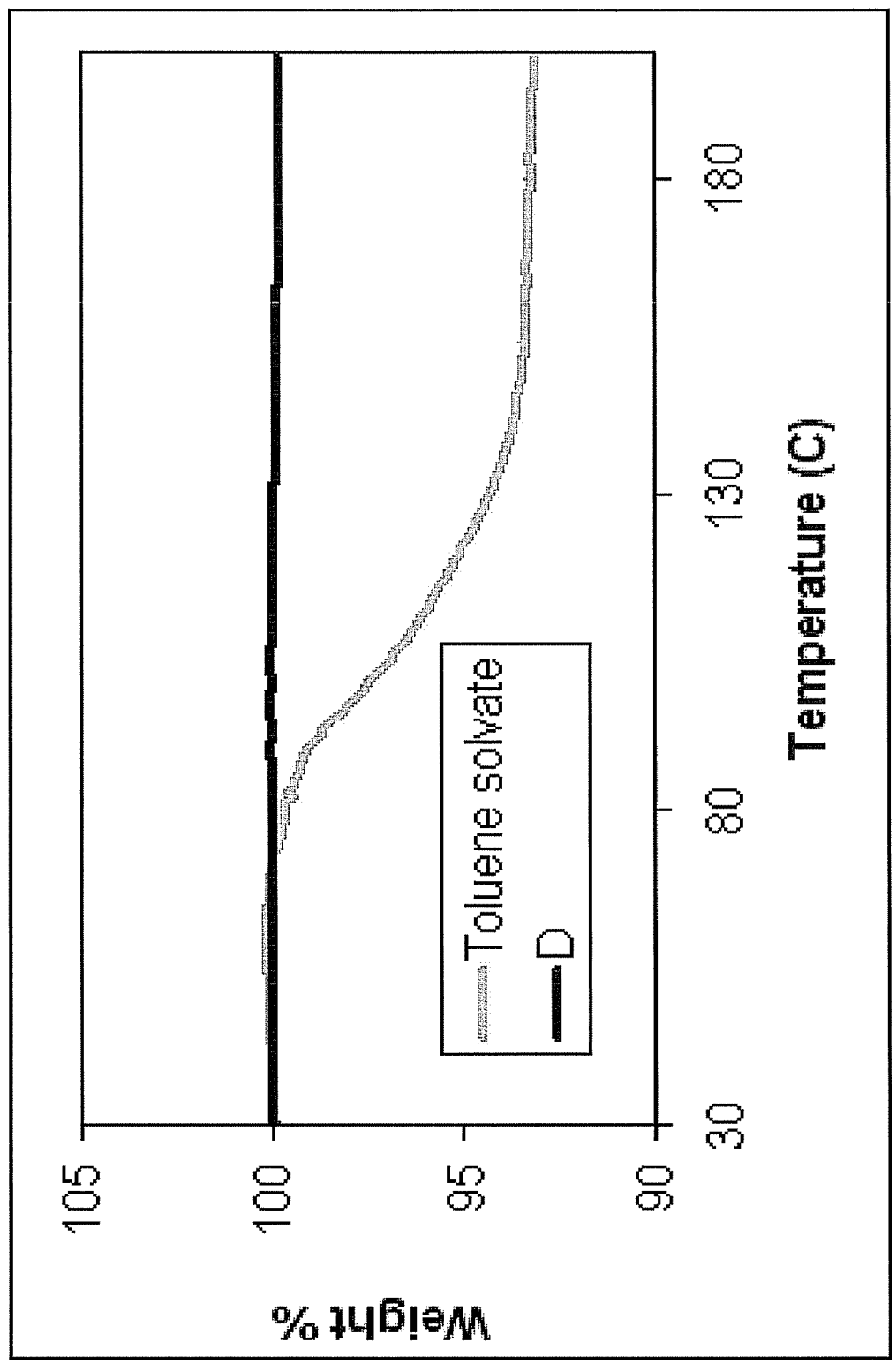
FIG. 20 Thermogravimetric analysis (TGA) graph of the toluene solvate (red) and form D (black).

In another embodiment, thermogravimetric analysis (TGA) graph of the toluene solvate in FIG. 20 shows that the toluene content in the solvate is about 7% which corresponds to one toluene molecule for every three molecules of S-1. In another embodiment the toluene molecules reside inside the unit cell structure rather than in channels or layers outside the lattice. In another embodiment, the toluene solvate solid form is the most stable form in toluene.

In some embodiments, crystalline forms of the SARMs of this invention comprise alteration of a given crystalline form to one structurally similar, yet not identical to the original form. In one embodiment, such changes in crystalline forms may produce one that is more structurally stable than the original form. In some embodiments, the crystalline forms of this invention comprise altered crystalline forms, as well as original forms, in a single preparation. In some embodiments, such altered crystalline forms may comprise a small percentage of the whole SARM compound preparation, for example, up to 1%, or in another embodiment, up to 5%, or up to 10%, or up to 15%, or up to 25% of the preparation. In another embodiment, such altered forms may comprise the majority of the SARM compound preparation and may comprise 55%, or in another embodiment, 65%, or in another embodiment, 75%, or 80%, or 85%, or 90%, or 95% or up to 100% of the SARM compound preparation. In one embodiment, the favorable crystalline form is thermodynamically favorable. In another embodiment the crystalline favorable form is a result of a change in humidity. In another embodiment the crystalline favorable form is a result of a change in temperature. In another embodiment the crystalline favorable form is a result of a change in solvents.

In some embodiments, the process for the preparation of polymorph of (R) or (S)—N-(4-cyano-3-(trifluoromethyl) phenyl)-3-(4-cyanophenoxy)-2-hydroxy-2-methylpropanamide compounds yield various crystalline forms. In one embodiment the process yields a mixture of crystalline/paracrystalline forms A, B', C and D. In one embodiment the process yields a mixture of crystalline/paracrystalline forms A, B', B", C and D. In another embodiment, the process yields a mixture of crystalline forms A and C. In another embodiment, the process yields a mixture of crystalline/paracrystalline forms A and B'. In another embodiment, the process yields a mixture of crystalline forms A and D. In another embodiment, the process yields a mixture of crystalline/paracrystalline forms B' and D. In another embodiment, the process yields a mixture of crystalline/paracrystalline forms B" and D. In another embodiment, the process yields a mixture of crystalline forms C and D. In another embodiment, the process yields a mixture of crystalline/paracrystalline forms B' and C. In another embodiment, the process yields a mixture of crystalline/paracrystalline forms A and B". In another embodiment, the process yields a mixture of paracrystalline forms B' and B". In another embodiment, the process yields a mixture of crystalline/paracrystalline forms C and B". In another embodiment, the process yields a mixture of crystalline/paracrystalline forms A, C and B". In another embodiment, the process yields a mixture of crystalline/paracrystalline forms A, D and B". In another embodiment, the process yields a mixture of crystalline/paracrystalline forms B', B" and C. In another embodiment, the process yields a mixture of crystalline/paracrystalline forms A, B' and B". In another embodiment, the process yields a mixture of crystalline/paracrystalline forms D, B' and B".

In one embodiment, the solid form compounds of this invention are dried from solution by vacuum at room temperature, followed by gradually increasing the temperature. In another embodiment, the solid form compounds of this invention are filtered from solution In one embodiment, the term "ambient temperature" refers to room temperature. In another embodiment, the term "ambient temperature" refers to 20-25° C. In another embodiment, "ambient temperature" refers to 25-30° C.

Figure 19:
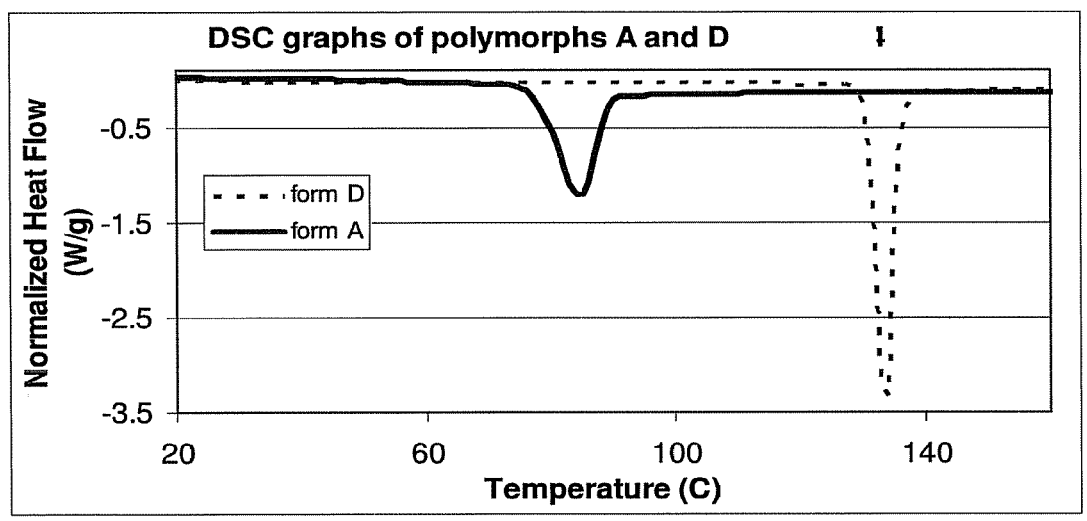
FIG. 19 demonstrates a DSC thermograms of forms A and D.

In another embodiment, form D is the most thermodynamically stable polymorph in both dry conditions and in the presence of water at ambient temperature up to its melting point of 130° C. In another embodiment, FIG. 19 depicts a differential scanning calorimeter (DSC) thermogram of form A and form D, where form A melts at about 80° C. and form D melts at about 130° C. In another embodiment, the enthalpy of melting for form A is 40±5 J/g while the enthalpy of melting for form D is 75±5 J/g.

In another embodiment form A is stable in its A form for at least 7 days under storage conditions of ambient temperature/75% RH (Relative Humidity), ambient temperature/100% RH, 30° C./75% RH and 50° C./0% RH. In another embodiment, form A converts to B' when stored at 50° C./75% RH. In another embodiment, form A converts to B' when stored at 40° C./75% RH within one month. In another embodiment form A stored at 25° C./60% RH and 30° C./65% RH is stable through 36 months and 9 months respectively.

In one embodiment, (R) or (S)—N-(4-cyano-3-(trifluoromethyl)phenyl)-3-(4-cyanophenoxy)-2-hydroxy-2-methylpropanamide are prepared by chiral synthesis.

In one embodiment, the (S)—N-(4-cyano-3-(trifluoromethyl)phenyl)-3-(4-cyanophenoxy)-2-hydroxy-2-methylpropanamide may be prepared by a process according to the following synthetic scheme:

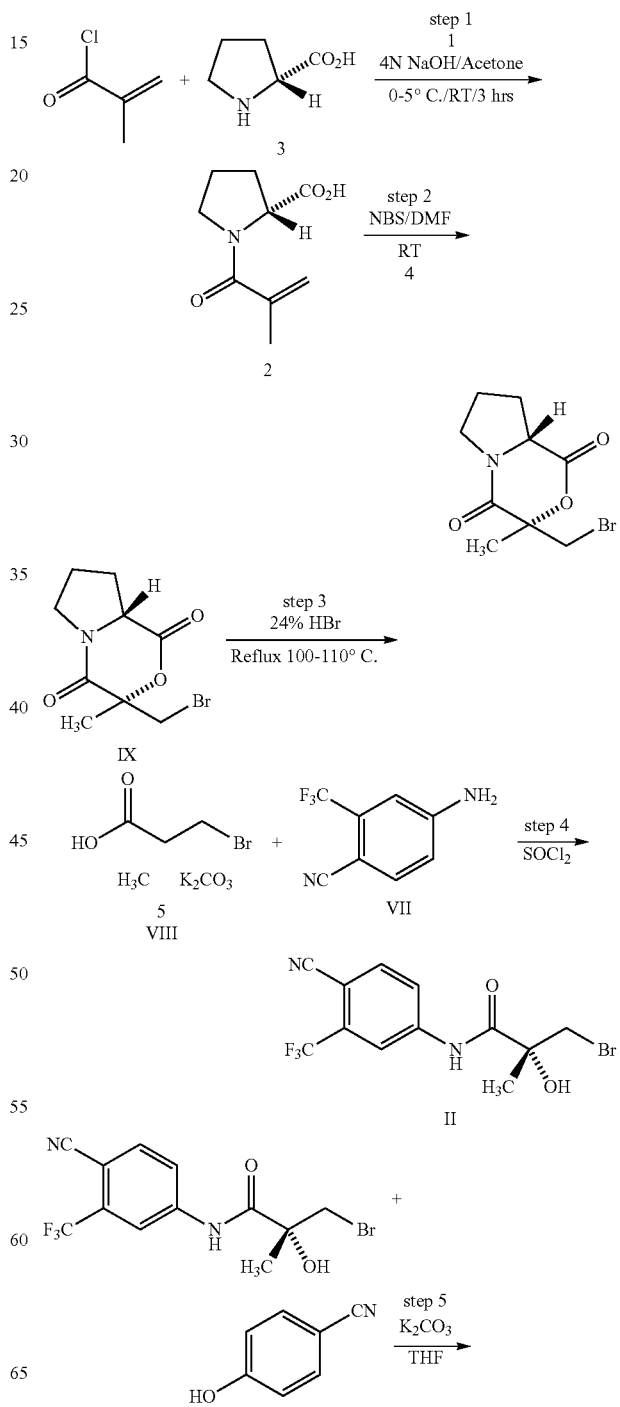

-continued

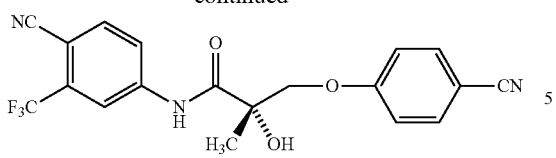

In one embodiment, the process described in the above scheme comprises reacting the acylanilide in step 5 with the cyanophenol, and such reaction may be conducted in the presence of potassium carbonate, sodium carbonate, or cesium carbonate. In one embodiment, reaction in the presence of potassium carbonate unexpectedly results in a product with fewer impurities as compared to a reaction conducted in the presence of cesium carbonate. This represents an improved and more efficient synthetic process for producing an end product, minimizing the need for additional purification steps. This finding is also advantageous to the production of other compounds such as 6, 9, 12, and 14 below.

In one embodiment, this invention provides a process for preparing (S)—N-(4-cyano-3-(trifluoromethyl)phenyl)-3-(4-cyanophenoxy)-2-hydroxy-2-methylpropanamide, said process comprising the steps of:

a) preparing a carboxylic acid of formula 1 by ring opening of a cyclic compound of formula 2 in the presence of HBr

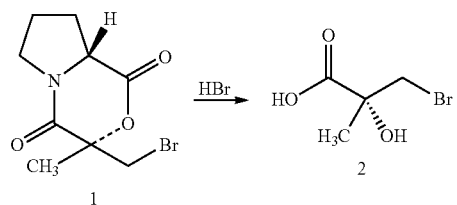

b) reacting an amine of formula 3:

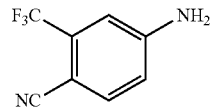

with the carboxylic acid of formula 2 in the presence of a coupling reagent, to produce an amide of formula 4

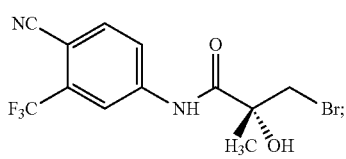

and c) reacting the amide of formula 4 with a compound of formula 5:

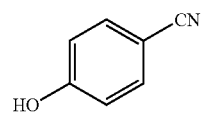

wherein step (c) is carried out in the presence of potassium carbonate and tetrahydrofuran.

In one embodiment, this invention provides a process for preparing a compound of formula 6:

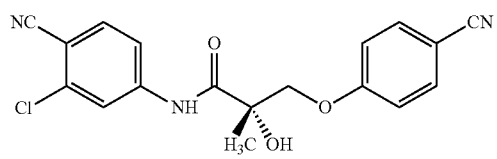 [SMILES: C[C@](O)(COc1ccc(C#N)cc1)C(=O)Nc1ccc(C#N)c(Cl)c1]

said process comprising the steps of:

a) preparing a carboxylic acid of formula 1 by ring opening of a cyclic compound of formula 2 in the presence of HBr

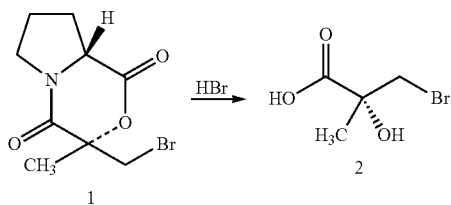

b) reacting an amine of formula 7:

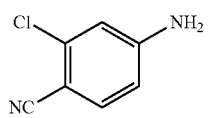

with the carboxylic acid of formula 2 in the presence of a coupling reagent, to produce an amide of formula 8:

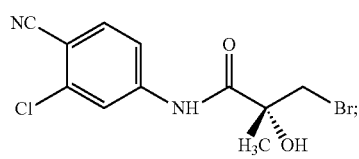

and c) reacting the amide of formula 8 with a compound of formula 5:

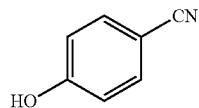
5 wherein step (c) is carried out in the presence of potassium carbonate and tetrahydrofuran.

In one embodiment, this invention provides a process for preparing a compound of formula 9:

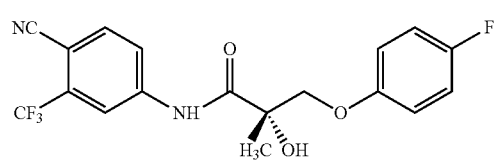
9 said process comprising the steps of:

a) preparing a carboxylic acid of formula 1 by ring opening of a cyclic compound of formula 2 in the presence of HBr

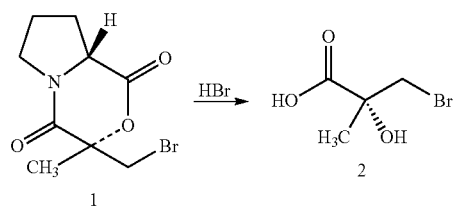

b) reacting an amine of formula 3:

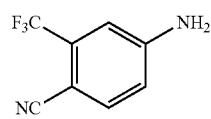
3 with the carboxylic acid of formula 2 in the presence of a coupling reagent, to produce an amide of formula 4

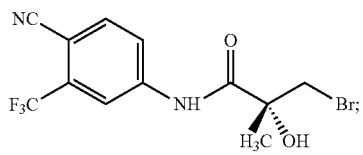
4 and c) reacting the amide of formula 4 with a compound of formula 10:

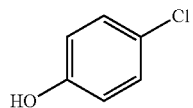
10 wherein step (c) is carried out in the presence of potassium carbonate and tetrahydrofuran.

In one embodiment, this invention provides a process for preparing a compound of formula 12:

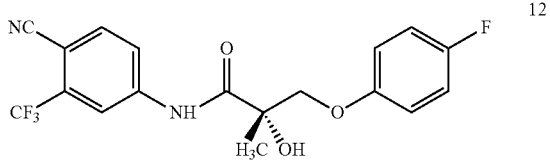 [SMILES: C[C@](O)(COc1ccc(F)cc1)C(=O)Nc1ccc(C#N)c(C(F)(F)F)c1]
12 said process comprising the steps of:

a) preparing a carboxylic acid of formula 1 by ring opening of a cyclic compound of formula 2 in the presence of HBr

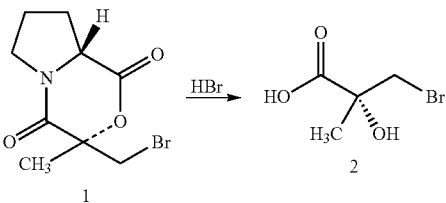

b) reacting an amine of formula 3:

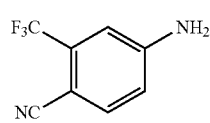
3 with the carboxylic acid of formula 2 in the presence of a coupling reagent, to produce an amide of formula 4

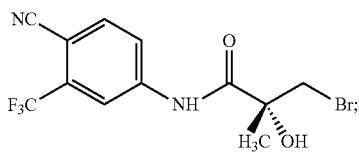 [SMILES: C[C@](O)(CBr)C(=O)Nc1ccc(C#N)c(C(F)(F)F)c1]

and c) reacting the amide of formula 4 with a compound of formula 13:

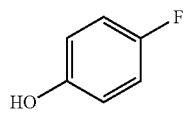

13 wherein step (c) is carried out in the presence of potassium carbonate and tetrahydrofuran.

In one embodiment, this invention provides a process for preparing a compound of formula 14:

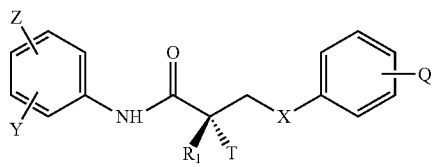

14

X is O, NH, Se, PR, or NR;

T is OH, OR, NHCOCH$_3$, or NHCOR;

Z is NO$_2$, CN, COOH, COR, NHCOR or CONHR;

Y is CF$_3$, F, I, Br, Cl, CN, CR$_3$ or SnR$_3$;

Q is alkyl, halogen, CF$_3$, CN, CR$_3$, SnR$_3$, NR$_2$, NHCOCH$_3$, NHCOCF$_3$, NHCOR, NHCONHR, NHCOOR, OCONHR, CONHR, NHCSCH$_3$, NHCSCF$_3$, NHCSR NHSO$_2$CH$_3$, NHSO$_2$R, OR, COR, OCOR, OSO$_2$R, SO$_2$R, SR; or Q together with the benzene ring to which it is attached is a fused ring system represented by structure A, B or C:

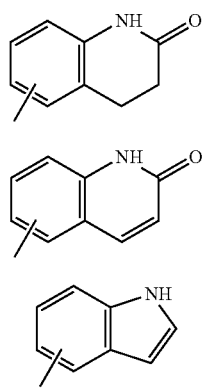

R is alkyl, haloalkyl, dihaloalkyl, trihaloalkyl, CH$_2$F, CHF$_2$, CF$_3$, CF$_2$CF$_3$, aryl, phenyl, halogen, alkenyl or OH; and R$_1$ is CH$_3$, CH$_2$F, CHF$_2$, CF$_3$, CH$_2$CH$_3$, or CF$_2$CF$_3$;

said process comprising the steps of:

a) preparing a carboxylic acid of formula 15 by ring opening of a cyclic compound of formula 16 in the presence of HBr

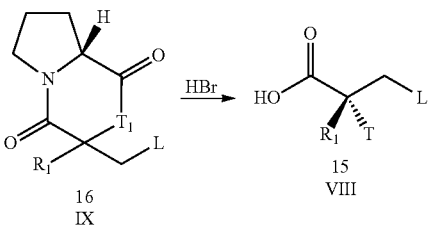

wherein L, R$_1$ and T are as defined above, and T$_1$ is O or NH;

b) reacting an amine of formula 17:

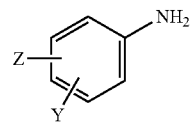

17 wherein Z and Y are as defined above, with the carboxylic acid of formula 17 in the presence of a coupling reagent, to produce an amide of formula 18

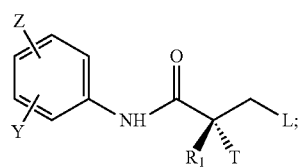

18 and c) coupling the amide of formula II with a compound of formula 19:

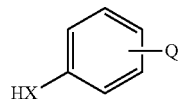

19 wherein Q and X are as defined above and wherein step (c) is carried out in the presence of potassium carbonate and tetrahydrofuran.

In one embodiment, crystalline and paracrystalline forms of this invention are prepared by any process which may yield the same, such as, but not limited to those exemplified herein, as will be appreciated by one skilled in the art. In one embodiment, such a process will utilize a starting material for the preparation of crystalline and paracrystalline forms of this invention, which in turn, in some embodiments is prepared according to the method schematically depicted hereinabove. In some embodiments, preparing the starting material comprises specific reaction of the amide of formula 4 with a compound of formula 5 in the presence of potassium carbonate and a polar solvent, such as for example and in some embodiments, tetrahydrofuran, results in the production of a highly pure preparation, which in turn may enhance the rate of crystallization. In some embodiments, use of the pure preparation as described herein, depending upon crystallization conditions employed may result in varied ratio of crystalline forms obtained. In some embodiments, use of the pure preparation as described herein, depending upon crystallization conditions employed may result in varied ratio of crystalline forms, and the rate at which such forms are produced.

In one embodiment, the process further comprises the step of converting the selective androgen receptor modulator (SARM) compound (R) or (S)—N-(4-cyano-3-(trifluoromethyl)phenyl)-3-(4-cyanophenoxy)-2-hydroxy-2-methylpropanamide to its analog, isomer, polymorph, polymorph form A, paracrystalline form B', solvate, metabolite, derivative, pharmaceutically acceptable salt, pharmaceutical product, N-oxide, hydrate, hemi-hydrate or any combination thereof.

In one embodiment, this invention provides a process for preparing an analog of a selective androgen modulator compound of this invention. In another embodiment, this invention provides a process for preparing an isomer of a selective androgen modulator compound of this invention. In another embodiment, this invention provides a process for preparing a metabolite of a selective androgen modulator compound of this invention. In another embodiment, this invention provides a process for preparing a derivative of a selective androgen modulator compound of this invention. In another embodiment, this invention provides a process for preparing a pharmaceutically acceptable salt of a selective androgen modulator compound of this invention. In another embodiment, this invention provides a process for preparing a pharmaceutical product of a selective androgen modulator compound of this invention. In another embodiment, this invention provides a process for preparing an N-oxide of a selective androgen modulator compound of this invention. In another embodiment, this invention provides a process for preparing a hydrate of a selective androgen modulator compound of this invention. In another embodiment, this invention provides a process for preparing a polymorph of a selective androgen modulator compound of this invention. In another embodiment, this invention provides a process for preparing a polymorph form A as herein described of a selective androgen modulator compound of this invention. In another embodiment, this invention provides a process for preparing a paracrystalline form B' as herein described of a selective androgen modulator compound of this invention. In another embodiment, this invention provides a process for preparing a polymorph form C as herein described of a selective androgen modulator compound of this invention. In another embodiment, this invention provides a process for preparing a polymorph form D as herein described of a selective androgen modulator compound of this invention. In another embodiment, this invention provides a process for preparing a paracrystalline form of a selective androgen modulator compound of this invention. In another embodiment, this invention provides a process for preparing a solvate of a selective androgen modulator compound of this invention. In another embodiment, this invention provides a process for preparing a combination of any of an analog, isomer, metabolite, derivative, polymorph, polymorph form A, paracrystalline form B', paracrystalline, solvate, pharmaceutically acceptable salt, N-oxide and/or hydrates of a selective androgen modulator compound of this invention. In one embodiment this invention comprises any compound thus prepared.

In one embodiment, the term "isomer" includes, but is not limited to, optical isomers and analogs, structural isomers and analogs, conformational isomers and analogs, and the like.

In one embodiment, the SARMs are the pure (R)-enantiomer. In another embodiment, the SARMs are the pure (S) enantiomer. In another embodiment, the SARMs are a mixture of the (R) and the (S) enantiomers. In another embodiment, the SARMs are a racemic mixture comprising an equal amount of the (R) and the (S) enantiomers. In one embodiment, the process of the present invention further provides a step of converting the SARM compound into its optically active isomer.

In one embodiment, separation of the optically-active (R) enantiomer or (S) enantiomer, from the racemic SARM compounds of this invention comprises crystallization techniques. In another embodiment, the crystallization techniques include differential crystallization of enantiomers. In another embodiment, the crystallization techniques include differential crystallization of diastereomeric salts (tartaric salts or quinine salts). In another embodiment, the crystallization techniques include differential crystallization of chiral auxillary derivatives (menthol esters, etc). In another embodiment, separation of the optically-active (R) enantiomer or (S) enantiomer, from the racemic SARM compounds of this invention comprises reacting the racemate mixture with another chiral group, forming of a diastereomeric mixture followed by separation of the diastereomers and removing the additional chiral group to obtain pure enantiomers. In another embodiment, separation of the optically-active (R) enantiomer or (S) enantiomer, from the racemic SARM compounds of this invention comprises chiral synthesis. In another embodiment, separation of the optically-active (R) enantiomer or (S) enantiomer, from the racemic SARM compounds of this invention comprises biological resolution. In another embodiment, separation of the optically-active (R) enantiomer or (S) enantiomer, from the racemic SARM compounds of this invention comprises enzymatic resolution. In another embodiment, separation of the optically-active (R) enantiomer or (S) enantiomer, from the racemic SARM compounds of this invention comprises chromatographic separation using a chiral stationary phase. In another embodiment, separation of the optically-active (R) enantiomer or (S) enantiomer, from the racemic SARM compounds of this invention comprises affinity chromatography. In another embodiment, separation of the optically-active (R) enantiomer or (S) enantiomer, from the racemic SARM compounds of this invention comprises capillary electrophoresis. In another embodiment, separation of the optically-active (R) enantiomer or (S) enantiomer, from the racemic SARM compounds of this invention comprises forming an ester group of the hydroxyl group of the chiral carbon with an optically-active acid, for example (−)-camphanic acid, separating the diastereomers esters, thus obtained, by fractional crystallization or preferably, by flash-chromatography, and then hydrolyzing each separate ester to the alcohol.

In another embodiment the S-enantiomer of SARM compound of this invention can be converted to the R-enantiomer or to its racemate. In another embodiment the R-enantiomer of SARM compound of this invention can be converted to the S-enantiomer or to its racemate. In one embodiment, one enantiomer can be converted to the other enantiomer or its racemate by using a chiral reactant, a solvent, a biocatalyst, chiral catalyst, asymmetric hydrogenation, an enzyme, or combination thereof.

In some embodiments the solid compounds of this invention comprise solvates. In one embodiment the term "solvate" refers to solvents combined with SARM compounds, for example, a solvate of ethylacetate, which is part of a polymorph structure of the SARM compound. Such solvents include ethanol, acetone, ethylacetate, THF, acetonitrile, dichloromethane, 1,4-dioxane, acetic acid, toluene, water, n-heptane, toluene, n-pentane TBME, or any combination thereof.

In another embodiment, the process of the present invention further provides a step of converting the SARM compound into its pharmaceutically acceptable salt. In one embodiment, pharmaceutically acceptable salts include salts of amino-substituted compounds with organic and inorganic acids, for example, citric acid and hydrochloric acid. The invention also includes N-oxides of the amino substituents of the compounds described herein. Pharmaceutically acceptable salts can also be prepared from phenolic compounds by treatment with inorganic bases, for example, sodium hydroxide. Also, esters of the phenolic compounds can be made with aliphatic and aromatic carboxylic acids, for example, acetic acid and benzoic acid esters.

The invention includes "pharmaceutically acceptable salts" of the compounds of this invention, which may be produced, by reaction of a compound of this invention with an acid or base.

Suitable pharmaceutically-acceptable salts of amines of Formula I may be prepared from an inorganic acid or from an organic acid. In one embodiment, examples of inorganic salts of amines are bisulfates, borates, bromides, chlorides, hemisulfates, hydrobromates, hydrochlorates, 2-hydroxyethylsulfonates (hydroxyethanesulfonates), iodates, iodides, isothionates, nitrate, persulfates, phosphate, sulfates, sulfamates, sulfanilates, sulfonic acids (alkylsulfonates, arylsulfonates, halogen substituted alkylsulfonates, halogen substituted arylsulfonates), sulfonates and thiocyanates.

In one embodiment, examples of organic salts of amines comprise aliphatic, cycloaliphatic, aromatic, araliphatic, heterocyclic, carboxylic and sulfonic classes of organic acids, examples of which are acetates, arginines, aspartates, ascorbates, adipates, anthranilate, algenate, alkane carboxylates, substituted alkane carboxylates, alginates, benzenesulfonates, benzoates, bisulfates, butyrates, bicarbonates, bitartrates, carboxilates, citrates, camphorates, camphorsulfonates, cyclohexylsulfamates, cyclopentanepropionates, calcium edetates, camsylates, carbonates, clavulanates, cinnamates, dicarboxylates, digluconates, dodecylsulfonates, dihydrochlorides, decanoates, enanthuates, ethanesulfonates, edetates, edisylates, estolates, esylates, fumarates, formates, fluorides, galacturonates, gluconates, glutamates, glycolates, glucorate, glucoheptanoates, glycerophosphates, gluceptates, glycollylarsanilates, glutarates, glutamate, heptanoates, hexanoates, hydroxymaleates, hydroxycarboxlic acids, hexylresorcinates, hydroxybenzoates, hydroxynaphthoate, hydrofluorate, lactates, lactobionates, laurates, malates, maleates, methylenebis(beta-oxynaphthoate), malonates, mandelates, mesylates, methane sulfonates, methylbromides, methylnitrates, methylsulfonates, monopotassium maleates, mucates, monocarboxylates, mitrates, naphthalenesulfonates, 2-naphthalenesulfonates, nicotinates, napsylates, N-methylglucamines, oxalates, octanoates, oleates, pamoates, phenylacetates, picrates, phenylbenzoates, pivalates, propionates, phthalates, phenylacetate, pectinates, phenylpropionates, palmitates, pantothenates, polygalacturates, pyruvates, quinates, salicylates, succinates, stearates, sulfanilate, subacetates, tartarates, theophyllineacetates, p-toluenesulfonates (tosylates), trifluoroacetates, terephthalates, tannates, teoclates, trihaloacetates, triethiodide, tricarboxylates, undecanoates or valerates.

In one embodiment, examples of inorganic salts of carboxylic acids or phenols comprise ammonium, alkali metals to include lithium, sodium, potassium, cesium; alkaline earth metals to include calcium, magnesium, aluminium; zinc, barium, cholines or quaternary ammoniums.

In another embodiment, examples of organic salts of carboxylic acids or phenols comprise arginine, organic amines to include aliphatic organic amines, alicyclic organic amines, aromatic organic amines, benzathines, t-butylamines, benethamines (N-benzylphenethylamine), dicyclohexylamines, dimethylamines, diethanolamines, ethanolamines, ethylenediamines, hydrabamines, imidazoles, lysines, methylamines, meglamines, N-methyl-D-glucamines, N,N'-dibenzylethylenediamines, nicotinamides, organic amines, ornithines, pyridines, picolinates, piperazines, procain, tris(hydroxymethyl)methylamines, triethylamines, triethanolamines, trimethylamines, tromethamines or ureas.

In one embodiment, the salts may be formed by conventional means, such as by reacting the free base or free acid form of the product with one or more equivalents of the appropriate acid or base in a solvent or medium in which the salt is insoluble or in a solvent such as water, which is removed in vacuo or by freeze drying or by exchanging the ions of a existing salt for another ion or suitable ion-exchange resin.

In one embodiment, the invention also includes N-oxides of the amino substituents of the compounds described herein. Also, esters of the phenolic compounds can be made with aliphatic and aromatic carboxylic acids, for example, acetic acid and benzoic acid esters.

This invention further includes a process for preparing derivatives of the SARM compounds. In some embodiments, the term "derivative" includes, but is not limited to, ether derivatives, acid derivatives, amide derivatives, ester derivatives and the like. Methods of preparing derivatives are known to a person skilled in the art. For example, ether derivatives are prepared by coupling of the corresponding alcohols. Amide and ester derivatives are prepared from the corresponding carboxylic acid by a reaction with amines and alcohols, respectively.

In some embodiments, this invention comprises a process for preparing hydrates of the SARM compounds. In one embodiment the term "hydrate" includes, but is not limited to, hemi-hydrate, monohydrate, dihydrate, trihydrate and the like. Hydrates of the SARM compounds may be prepared by contacting the SARM compound with water under suitable conditions to produce the hydrate of choice. The term "hemi-hydrate" refers to hydrate in which the molecular ratio of water molecules to anhydrous compound is 1:2.

This invention further includes a process for preparing pharmaceutical products of the SARM compounds. The term "pharmaceutical product" means a composition suitable for pharmaceutical use (pharmaceutical composition), as defined herein.

In some embodiments, this invention comprises a process for preparing analogs of the SARM compounds. In one embodiment the term "analog" refers to a compound with a structure, which is similar, but not identical to that of the referenced compound. In another embodiment the term "analog" refers to an isomer or derivative of the SARM compound. In another embodiment the term "analog of a SARM compound" of this invention refers to a compound having different substituents on each or both phenyl rings in the compound. In another embodiment, the term "analog" refers to the incorporation of different aromatic rings, for example pyridyl rings, in place of the one or both benzene rings. In another embodiment, the term "analog" refers to the incorporation of a sulfur atom instead of each or both ether and keto groups.

In some embodiments, this invention comprises a metabolite of the SARM compounds. The term "metabolite" refers, in some embodiments to any substance produced from another substance by mimicking or via metabolic process. In some embodiment such metabolites can be prepared synthetically and are active in situ, as they are comparable to naturally produced metabolites.

In some embodiments, the term "about" refers to an up to 10% variance from a specified value, or in some embodiments, an up to 5% variance from a specified value, or in some embodiments, an up to 1% variance from a specified value. In some embodiments, the term "about" refers to a value falling within a scientifically acceptable error range for that type of value, which will depend on the qualitative nature of the measurement obtained given the tools and methodology available.

In some embodiments, the term "unique" as used herein refers to being the only one, or in some embodiments, the term "unique" refers to being without a like or equal.

Pharmaceutical Compositions

In one embodiment, this invention provides a composition comprising a crystalline form of anhydrous (R) or (S)—N-(4-cyano-3-(trifluoromethyl)phenyl)-3-(4-cyanophenoxy)-2-hydroxy-2-methylpropanamide and a suitable carrier or diluent.

In another embodiment, this invention provides a composition comprising a crystalline form A of anhydrous (S)—N-(4-cyano-3-(trifluoromethyl)phenyl)-3-(4-cyanophenoxy)-2-hydroxy-2-methylpropanamide and a suitable carrier or diluent.

In one embodiment, this invention provides a composition comprising a paracrystalline form of (R) or (S)—N-(4-cyano-3-(trifluoromethyl)phenyl)-3-(4-cyanophenoxy)-2-hydroxy-2-methylpropanamide and a suitable carrier or diluent.

In one embodiment, this invention provides a composition comprising a paracrystalline form B' of (S)—N-(4-cyano-3-(trifluoromethyl)phenyl)-3-(4-cyanophenoxy)-2-hydroxy-2-methylpropanamide and a suitable carrier or diluent.

In one embodiment, this invention provides a composition comprising a mixture of any solid forms of (R) or (S)—N-(4-cyano-3-(trifluoromethyl)phenyl)-3-(4-cyanophenoxy)-2-hydroxy-2-methylpropanamide compound of this invention and a suitable carrier or diluent.

In another embodiment, this invention provides a composition comprising a mixture of crystalline and paracrystalline solid forms of (R) or (S)—N-(4-cyano-3-(trifluoromethyl)phenyl)-3-(4-cyanophenoxy)-2-hydroxy-2-methylpropanamide compound and a suitable carrier or diluent.

In another embodiment, this invention provides a composition comprising a mixture of crystalline form A and paracrystalline solid form B' of (S)—N-(4-cyano-3-(trifluoromethyl)phenyl)-3-(4-cyanophenoxy)-2-hydroxy-2-methylpropanamide compound and a suitable carrier or diluent.

In one embodiment, this invention encompasses compositions comprising the different forms of (R) or (S)—N-(4-cyano-3-(trifluoromethyl)phenyl)-3-(4-cyanophenoxy)-2-hydroxy-2-methylpropanamide they can be in different ratios or a single form per composition, which possesses properties useful in the treatment of androgen-related conditions described herein. In another embodiment, this invention encompasses compositions comprising different isomers of N-(4-cyano-3-(trifluoromethyl)phenyl)-3-(4-cyanophenoxy)-2-hydroxy-2-methylpropanamide, they can be in different ratios or a single isomer per composition, which possesses properties useful in the treatment of androgen-related conditions described herein.

In some embodiments, the phrase, "pharmaceutical composition" refers to a "therapeutically effective amount" of the active ingredient, i.e. the SARM compound, together with a pharmaceutically acceptable carrier or diluent. In some embodiments, the phrase "therapeutically effective amount" refers to an amount which provides a therapeutic effect for a given condition and administration regimen.

The pharmaceutical compositions containing the SARM agent can be administered to a subject by any method known to a person skilled in the art, such as parenterally, paracancerally, transmucosally, transdermally, intramuscularly, intravenously, intradermally, subcutaneously, intraperitoneally, intraventricularly, intracranially or intratumorally.

In another embodiment this invention provides, a composition of the solid forms of this invention and a suitable carrier or diluent.

In one embodiment, the pharmaceutical compositions are administered orally, and are thus formulated in a form suitable for oral administration, i.e. as a solid preparation.

Suitable solid oral formulations include tablets, capsules, pills, granules, pellets and the like.

In one embodiment of the present invention, the SARM compounds are formulated in a capsule. In accordance with this embodiment, the compositions of the present invention comprise in addition to the SARM active compound and the inert carrier or diluent, a hard gelating capsule.

Oral formulations containing the present polymorph can comprise any conventionally used oral forms, including tablets, capsules, buccal forms, troches, or lozenges. Capsules may contain mixtures of the crystalline form A in the desired percentage together any other polymorph(s) of SARM or amorphous SARM. Capsules or tablets of the desired crystalline form of the desired percentage composition may also be combined with mixtures of other active compounds or inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc.

Tablet formulations can be made by conventional compression, wet granulation, or dry granulation methods and utilize pharmaceutically acceptable diluents (fillers), binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations, in some embodiments, utilize standard delay or time release formulations or spansules.

Example excipient systems suitable for preparing formulations of the present polymorph include one or more fillers, disintegrants, and lubricants.

The filler component can be any filler component known in the art including, but not limited to, lactose, microcrystalline cellulose, sucrose, mannitol, calcium phosphate, calcium carbonate, powdered cellulose, maltodextrin, sorbitol, starch, or xylitol.

Disintegrants suitable for use in the present formulations can be selected from those known in the art, including pregelatinized starch and sodium starch glycolate. Other useful disintegrants include croscarmellose sodium, crospovidone, starch, alginic acid, sodium alginate, clays (e.g. veegum or xanthan gum), cellulose floc, ion exchange resins, or effervescent systems, such as those utilizing food acids (such as citric acid, tartaric acid, malic acid, fumaric acid, lactic acid, adipic acid, ascorbic acid, aspartic acid, erythorbic acid, glutamic acid, and succinic acid) and an alkaline carbonate component (such as sodium bicarbonate, calcium carbonate, magnesium carbonate, potassium carbonate, ammonium carbonate, etc.). The disintegrant(s) useful herein can comprise from about 4% to about 40% of the composition by weight, preferably from about 15% to about 35%, more preferably from about 20% to about 35%.

The pharmaceutical formulations can also contain an antioxidant or a mixture of antioxidants, such as ascorbic acid. Other antioxidants which can be used include sodium ascorbate and ascorbyl palmitate, preferably in conjunction with an amount of ascorbic acid.

An example range for the antioxidant(s) is from about 0.5% to about 15% by weight, most preferably from about 0.5% to about 5% by weight.

In some embodiments of this invention, the active pharmacological agent(s) comprise from about 0.5% to about 20%, by weight, of the final composition, or in some embodiments, from about 1% to about 5%, and the coating or capsule comprises up to about 8%, by weight, of the final composition.

The formulations described herein can be used in an uncoated or non-encapsulated solid form. In some embodiments, the pharmacological compositions are optionally coated with a film coating, for example, comprising from about 0.3% to about 8% by weight of the overall composition. Film coatings useful with the present formulations are known in the art and generally consist of a polymer (usually a cellulosic type of polymer), a colorant and a plasticizer. Additional ingredients such as wetting agents, sugars, flavors, oils and lubricants may be included in film coating formulations to impart certain characteristics to the film coat. The compositions and formulations herein may also be combined and processed as a solid, then placed in a capsule form, such as a gelatin capsule.

In another embodiment, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

As used herein "pharmaceutically acceptable carriers or diluents" are well known to those skilled in the art. The carrier or diluent may be a solid carrier or diluent for solid formulations.

Solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In addition, the compositions may further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), antioxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweetners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

In one embodiment, the pharmaceutical compositions provided herein are controlled release compositions, i.e. compositions in which the SARM compound is released over a period of time after administration. In another embodiment, the composition is an immediate release composition, i.e. a composition in which all of the SARM compound is released immediately after administration.

In yet another embodiment, the pharmaceutical composition can be delivered in a controlled release system. For example, the agent may be administered using liposomes, or other modes of oral administration.

The compositions may also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance.

The preparation of pharmaceutical compositions which contain an active component is well understood in the art, for example by mixing, granulating, or tablet-forming processes. The active therapeutic ingredient is often mixed with excipients which are pharmaceutically acceptable and compatible with the active ingredient. For oral administration, the SARM agents or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicine, the salts of the SARM will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic: acid, oxalic acid, citric acid, tartaric acid, carbonic acid or phosphoric acid.

Biological Activity of Selective Androgen Modulator Compounds

The solid forms and processes for producing the same provided herein are, in some embodiments, directed to selective androgen receptor modulators (SARMs), which are useful for oral testosterone replacement therapy, having unexpected in-vivo androgenic and anabolic activity. In some embodiments, appropriately substituted compounds are effective to treat prostate cancer and useful for imaging of prostate cancer.

As contemplated herein, the appropriately substituted SARM compounds of the present invention are useful for a) male contraception; b) treatment of a variety of hormone-related conditions, for example conditions associated with Androgen Decline in Aging Male (ADAM), such as fatigue, depression, decreased libido, sexual dysfunction, erectile dysfunction, hypogonadism, osteoporosis, hair loss, anemia, obesity, sarcopenia, osteopenia, osteoporosis, benign prostate hyperplasia, alterations in mood and cognition and prostate cancer; c) treatment of conditions associated with ADIF, such as sexual dysfunction, decreased sexual libido, hypogonadism, sarcopenia, osteopenia, osteoporosis, alterations in cognition and mood, depression, anemia, hair loss, obesity, endometriosis, breast cancer, uterine cancer and ovarian cancer; d) treatment and/or prevention of chronic muscular wasting; e) decreasing the incidence of, halting or causing a regression of prostate cancer; f) oral androgen replacement and/or other clinical therapeutic and/or diagnostic areas.

As used herein, receptors for extracellular signaling molecules are collectively referred to as "cell signaling receptors". Many cell signaling receptors are transmembrane proteins on a cell surface; when they bind an extracellular signaling molecule (i.e., a ligand), they become activated so as to generate a cascade of intracellular signals that alter the behavior of the cell. In contrast, in some cases, the receptors are inside the cell and the signaling ligand has to enter the cell to activate them; these signaling molecules therefore must be sufficiently small and hydrophobic to diffuse across the plasma membrane of the cell. As used herein, these receptors are collectively referred to as "intracellular cell signaling receptors".

Steroid hormones are one example of small hydrophobic molecules that diffuse directly across the plasma membrane of target cells and bind to intracellular cell signaling receptors. These receptors are structurally related and constitute the intracellular receptor superfamily (or steroid-hormone receptor superfamily). Steroid hormone receptors include progesterone receptors, estrogen receptors, androgen receptors, glucocorticoid receptors, and mineralocorticoid receptors. The present invention is particularly directed to androgen receptors.

In addition to ligand binding to the receptors, the receptors can be blocked to prevent ligand binding. When a substance binds to a receptor, the three-dimensional structure of the substance fits into a space created by the three-dimensional structure of the receptor in a ball and socket configuration.

In one embodiment, the present invention is directed to processes for preparing solid forms of selective androgen receptor modulator compounds which are agonist compounds. Thus, in one embodiment, the SARM compounds of the present invention are useful in binding to and activating steroidal hormone receptors. In one embodiment, the agonist compound of the present invention is an agonist which binds the androgen receptor. In another embodiment, the compound has high affinity for the androgen receptor. In another embodiment, the agonist compound also has anabolic activity. In another embodiment, the present invention provides selective androgen modulator compounds which have agonistic and anabolic activity of a nonsteroidal compound for the androgen receptor.

In one embodiment, the present invention is directed to processes for preparing solid forms of selective androgen receptor modulator compounds which are antagonist compounds. Thus, in one embodiment, the solid forms of the SARM compounds of the present invention are useful in binding to and inactivating steroidal hormone receptors. In another embodiment, the solid forms of the invention have a high affinity for the androgen receptor. In another embodiment, the solid forms of this invention also have anabolic activity. In another embodiment, the solid forms of the SARM compounds bind irreversibly to the androgen receptor. In another embodiment, the solid forms of the SARM compounds are alkylating agents.

In yet another embodiment, the solid forms of the SARM compounds of the present invention can be classified as partial AR agonist/antagonists. The solid forms of the SARMs are AR agonists in some tissues, and cause increased transcription of AR-responsive genes (e.g. muscle anabolic effect). In other tissues, these compounds serve as inhibitors at the AR to prevent agonistic effects of the native androgens.

Assays to determine whether the compounds of the present invention are AR agonists or antagonists are well known to a person skilled in the art. For example, AR agonistic activity can be determined by monitoring the ability of the solid forms of the SARM compounds to maintain and/or stimulate the growth of AR containing tissue such as prostate and seminal vesicles, as measured by weight. AR antagonistic activity can be determined by monitoring the ability of the SARM compounds to inhibit the growth of AR containing tissue.

In another embodiment, the solid forms of the SARM compounds bind irreversibly to the androgen receptor of a mammal, for example a human. Thus, in one embodiment, the compounds of the present invention may contain a functional group (e.g. affinity label) that allows alkylation of the androgen receptor (i.e. covalent bond formation). Thus, in this case, the compounds are alkylating agents which bind irreversibly to the receptor and, accordingly, cannot be displaced by a steroid, such as the endogenous ligands DHT and testosterone. An "alkylating agent" is defined herein as an agent which alkylates (forms a covalent bond) with a cellular component, such as DNA, RNA or protein. It is a highly reactive chemical that introduces alkyl radicals into biologically active molecules and thereby prevents their proper functioning. The alkylating moiety is an electrophilic group that interacts with nucleophilic moieties in cellular components.

According to one embodiment of the present invention, a method is provided for binding the solid forms of the SARM compounds of the present invention to an androgen receptor by contacting the receptor with the solid forms of the SARM compound, such as polymorph form A, polymorph form C, polymorph form D, paracrystalline form B', paracrystalline B", a solvate thereof, a polymorph thereof, a metabolite thereof, etc., or any combination thereof, under conditions effective to cause the selective androgen receptor modulator compound to bind the androgen receptor. The binding of the solid forms of the selective androgen receptor modulator compounds to the androgen receptor enables the compounds of the present invention to be useful as a male contraceptive and in a number of hormone therapies. The agonist compounds bind to and activate the androgen receptor. The antagonist compounds bind to and inactivate the androgen receptor. Binding of the agonist or antagonist compounds is either reversible or irreversible.

In one embodiment, the solid forms of the SARM compounds of the present invention are administered as the sole active ingredient. However, also encompassed within the scope of the present invention are methods for hormone therapy, for treating prostate cancer, for delaying the progression of prostate cancer, and for preventing and/or treating the recurrence of prostate cancer, which comprise administering the solid forms of the SARM compounds in combination with one or more therapeutic agents. These agents include, but are not limited to: LHRH analogs, reversible antiandrogens, antiestrogens, anticancer drugs, 5-alpha reductase inhibitors, aromatase inhibitors, progestins, agents acting through other nuclear hormone receptors, selective estrogen receptor modulators (SERM), progesterone, estrogen, PDE5 inhibitors, apomorphine, bisphosphonate, and one or more solid forms of the SARMS, for example one with AR agonistic activity.

Thus, in one embodiment, the present invention provides compositions and pharmaceutical compositions comprising the solid forms of the selective androgen receptor modulator compound, in combination with an LHRH analog. In another embodiment, the present invention provides compositions and pharmaceutical compositions comprising the solid forms of the selective androgen receptor modulator compound, in combination with a reversible antiandrogen. In another embodiment, the present invention provides compositions and pharmaceutical compositions comprising the solid forms of the selective androgen receptor modulator compound, in combination with an antiestrogen. In another embodiment, the present invention provides compositions and pharmaceutical compositions comprising the solid forms of the selective androgen receptor modulator compound, in combination with an anticancer drug. In another embodiment, the present invention provides compositions and pharmaceutical compositions comprising the solid forms of the selective androgen receptor modulator compound, in combination with a 5-alpha reductase inhibitor. In another embodiment, the present invention provides compositions and pharmaceutical compositions comprising the solid forms of the selective androgen receptor modulator compound, in combination with an aromatase inhibitor. In another embodiment, the present invention provides compositions and pharmaceutical compositions comprising the solid forms of the selective androgen receptor modulator compound, in combination with a progestin. In another embodiment, the present invention provides compositions and pharmaceutical compositions comprising the solid forms of the selective androgen receptor modulator compound, in combination with an agent acting through other nuclear hormone receptors. In another embodiment, the present invention provides compositions and pharmaceutical compositions comprising the solid forms of the selective androgen receptor modulator compound, in combination with a selective estrogen receptor modulators (SERM). In another embodiment, the present invention provides compositions and pharmaceutical compositions comprising the solid forms of the selective androgen receptor modulator compound, in combination with progesterone. In another embodiment, the present invention provides compositions and pharmaceutical compositions comprising the solid forms of the selective androgen receptor modulator compound, in combination with estrogen. In another embodiment, the present invention provides compositions and pharmaceutical compositions comprising the solid forms of the selective androgen receptor modulator compound, in combination with PDE5 inhibitors. In another embodiment, the present invention provides compositions and pharmaceutical compositions comprising the solid forms of the selective androgen receptor modulator compound, in combination with apomorphine. In another embodiment, the present invention provides compositions and pharmaceutical compositions comprising the solid forms of the selective androgen receptor modulator compound, in combination with a bisphosphonate. In another embodiment, the present invention provides compositions and pharmaceutical compositions comprising the solid forms of the selective androgen receptor modulator compound, in combination with one or more additional SARMs.

The following examples are presented in order to more fully illustrate the preferred embodiments of the invention. They should in no way be construed, however, as limiting the broad scope of the invention.

EXPERIMENTAL DETAILS SECTION

Example 1: Synthesis of Compound S-1

(2R)-1-Methacryloylpyrrolidin-2-carboxylic Acid

D-Proline, 14.93 g, 0.13 mol) was dissolved in 71 mL of 2 N NaOH and cooled in an ice bath; the resulting alkaline solution was diluted with acetone (71 mL). An acetone solution (71 mL) of methacrylolyl chloride (13.56 g, 0.13 mol) and 2N NaOH solution (71 mL) were simultaneously added over 40 min to the aqueous solution of D-proline in an ice bath. The pH of the mixture was kept at 10-11° C. during the addition of the methacrylolyl chloride. After stirring (3 h, room temperature), the mixture was evaporated in vacuo at a temperature at 35-45° C. to remove acetone. The resulting solution was washed with ethyl ether and was acidified to pH 2 with concentrated HCl. The acidic mixture was saturated with NaCl and was extracted with EtOAc (100 mL×3). The combined extracts were dried over $Na_2SO_4$, filtered through Celite, and evaporated in vacuo to give the crude product as a colorless oil. Recrystallization of the oil from ethyl ether and hexanes afforded 16.2 (68%) of the desired compound as colorless crystals: mp 102-103° C. (lit. [214] mp 102.5-103.5° C.); the NMR spectrum of this compound demonstrated the existence of two rotamers of the title compound. $^1$H NMR (300 MHz, DMSO-$d_6$) δ 5.28 (s) and 5.15 (s) for the first rotamer, 5.15 (s) and 5.03 (s) for the second rotamer (totally 2H for both rotamers, vinyl $CH_2$), 4.48-4.44 for the first rotamer, 4.24-4.20 (m) for the second rotamer (totally 1H for both rotamers, CH at the chiral canter), 3.57-3.38 (m, 2H, $CH_2$), 2.27-2.12 (1H, CH), 1.97-1.72 (m, 6H, $CH_2$, CH, Me); $^{13}$C NMR (75 MHz, DMSO-$d_6$) δ for major rotamer 173.3, 169.1, 140.9, 116.4, 58.3, 48.7, 28.9, 24.7, 19.5: for minor rotamer 174.0, 170.0, 141.6, 115.2, 60.3, 45.9, 31.0, 22.3, 19.7; IR (KBr) 3437 (OH), 1737 (C=O), 1647 (CO, COOH), 1584, 1508, 1459, 1369, 1348, 1178 cm$^{-1}$; $[\alpha]_D^{26}$+80.8° (c=1, MeOH); Anal. Calcd. for $C_9H_{13}NO_3$: C, 59.00, H, 7.15, N, 7.65. Found: C, 59.13, H, 7.19, N, 7.61.

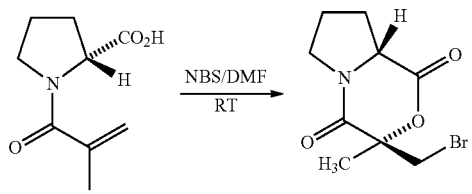

(3R,8aR)-3-Bromomethyl-3-methyl-tetrahydro-pyrrolo[2,1-c][1,4]oxazine-1,4-dione

A solution of NBS (23.5 g, 0.132 mol) in 100 mL of DMF was added dropwise to a stirred solution of the (methylacryloyl)-pyrrolidine (16.1 g, 88 mmol) in 70 mL of DMF under argon at room temperature, and the resulting mixture was stirred 3 days. The solvent was removed in vacuo, and a yellow solid was precipitated. The solid was suspended in water, stirred overnight at room temperature, filtered, and dried to give 18.6 (81%) (smaller weight when dried ~34%) of the title compound as a yellow solid: mp 152-154° C. (lit. [214] mp 107-109° C. for the S-isomer); $^1$H NMR (300 MHz, DMSO-$d_6$) δ 4.69 (dd, J=9.6 Hz, J=6.7 Hz, 1H, CH at the chiral center), 4.02 (d, J=11.4 Hz, 1H, $CHH_a$), 3.86 (d, J=11.4 Hz, 1H, $CHH_b$), 3.53-3.24 (m, 4H, $CH_2$), 2.30-2.20 (m, 1H, CH), 2.04-1.72 (m, 3H, $CH_2$ and CH), 1.56 (s, 2H, Me); $^{13}$C NMR (75 MHz, DMSO-$d_6$) δ 167.3, 163.1, 83.9, 57.2, 45.4, 37.8, 29.0, 22.9, 21.6; IR (KBr) 3474, 1745 (C=O), 1687 (C=O), 1448, 1377, 1360, 1308, 1227, 1159, 1062 cm$^{-1}$; $[\alpha]_D^{26}$+124.5° (c=1.3, chloroform); Anal. Calcd. for $C_9H_{12}BrNO_3$: C, 41.24, H, 4.61, N, 5.34. Found: C, 41.46, H, 4.64, N, 5.32.

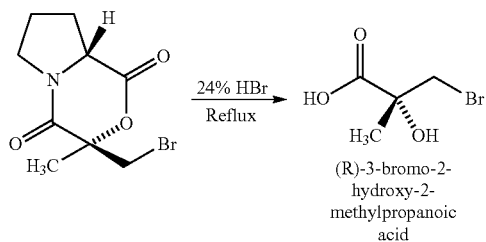

(2R)-3-Bromo-2-hydroxy-2-methylpropanoic Acid

A mixture of bromolactone (18.5 g, 71 mmol) in 300 mL of 24% HBr was heated at reflux for 1 h. The resulting solution was diluted with brine (200 mL), and was extracted with ethyl acetate (100 mL×4). The combined extracts were washed with saturated $NaHCO_3$ (100 mL×4). The aqueous solution was acidified with concentrated HCl to pH=1, which, in turn, was extracted with ethyl acetate (100 mL×4). The combined organic solution was dried over $Na_2SO_4$, filtered through Celite, and evaporated in vacuo to dryness. Recrystallization from toluene afforded 10.2 g (86%) of the desired compound as colorless crystals: mp 107-109° C. (lit. [214] mp 109-113° C. for the S-isomer); $^1$H NMR (300 MHz, DMSO-$d_6$) δ 3.63 (d, J=10.1 Hz, 1H, $CHH_a$), 3.52 (d, J=10.1 Hz, 1H, $CHH_b$), 1.35 (s, 3H, Me); IR (KBr) 3434 (OH), 3300-2500 (COOH), 1730 (C=O), 1449, 1421, 1380, 1292, 1193, 1085 cm$^{-1}$; $[\alpha]_D^{26}$+10.5° (c=2.6, MeOH); Anal. Calcd. for $C_4H_7BrO_3$: C, 26.25, H, 3.86. Found: C, 26.28, H, 3.75.

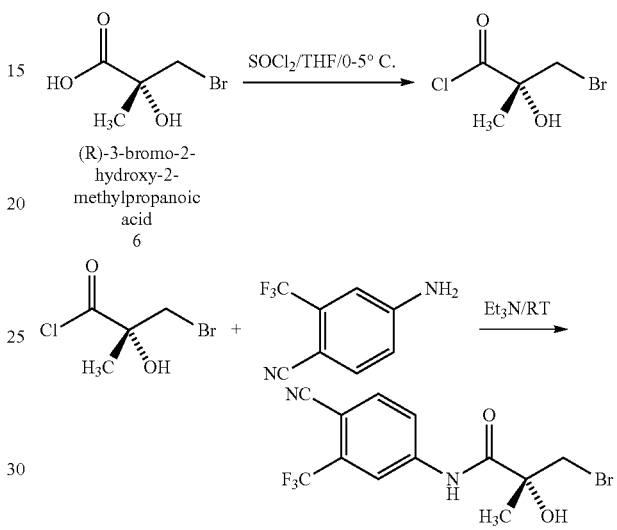

Synthesis of (2R)-3-Bromo-N-[4-cyano-3-(trifluoromethyl) phenyl]-2-hydroxy-2-methylpropanamide Thionyl chloride (46.02 g, 0.39 mol) was added dropwise to a cooled solution (less than 4° C.) of 6 (51.13 g, 0.28 mol) in 300 mL of THF under an argon atmosphere. The resulting mixture was stirred for 3 h under the same condition. To this was added $Et_3N$ (39.14 g, 0.39 mol) and stirred for 20 min under the same condition. After 20 min, 5-amino-2-cyanobenzotrifluoride (40.0 g, 0.21 mol), 400 mL of THF were added and then the mixture was allowed to stir overnight at room temperature. The solvent was removed under reduced pressure to give a solid which was treated with 300 mL of $H_2O$, extracted with EtOAc (2×400 mL). The combined organic extracts were washed with saturated $NaHCO_3$ solution (2×300 mL) and brine (300 mL). The organic layer was dried over $MgSO_4$ and concentrated under reduced pressure to give a solid which was purified from column chromatography using $CH_2Cl_2$/EtOAc (80:20) to give a solid. This solid was recrystallized from $CH_2Cl_2$/hexane to give 55.8 g (73.9%) of (2R)-3-Bromo-N-[4-cyano-3-(trifluoromethyl) phenyl]-2-hydroxy-2-methylpropanamide as a light-yellow solid.

$^1$H NMR (CDCl$_3$/TMS) δ 1.66 (s, 3H, $CH_3$), 3.11 (s, 1H, OH), 3.63 (d, J=10.8 Hz, 1H, $CH_2$), 4.05 (d, J=10.8 Hz, 1H, $CH_2$), 7.85 (d, J=8.4 Hz, 1H, ArH), 7.99 (dd, J=2.1, 8.4 Hz, 1H, ArH), 8.12 (d, J=2.1 Hz, 1H, ArH), 9.04 (bs, 1H, NH). Calculated Mass: 349.99, [M-H]$^-$ 349.0. M.p.: 124-126° C.

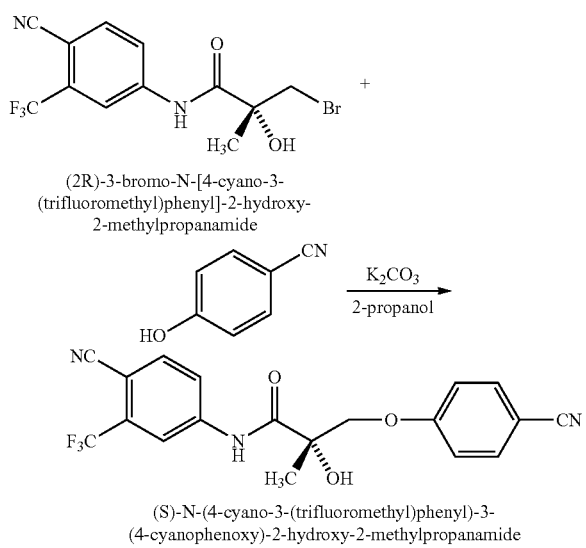

Synthesis of (S)—N-(4-cyano-3-(trifluoromethyl) phenyl)-3-(4-cyanophenoxy)-2-hydroxy-2-methyl-propanamide A mixture of bromoamide ((2R)-3-bromo-N-[4-cyano-3-(trifluoromethyl)phenyl]-2-hydroxy-2-methylpropanamide, 50 g, 0.14 mol), anhydrous $K_2CO_3$ (59.04 g, 0.43 mol), and 4-cyanophenol (25.44 g, 0.21 mol) in 500 mL of 2-propanol was heated to reflux for 3 h and then concentrated under reduced pressure to give a solid. The resulting residue was treated with 500 mL of $H_2O$ and then extracted with EtOAc (2×300 mL). The combined EtOAc extracts were washed with 10% NaOH (4×200 mL) and brine. The organic layer was dried over $MgSO_4$ and then concentrated under reduced pressure to give an oil which was treated with 300 mL of ethanol and an activated carbon. The reaction mixture was heated to reflux for 1 h and then the hot mixture was filtered through Celite. The filtrate was concentrated under reduced pressure to give an oil. This oil was purified by column chromatography using $CH_2Cl_2$/EtOAc (80:20) to give an oil which was crystallized from $CH_2Cl_2$/hexane to give 33.2 g (59.9%) of (S)—N-(4-cyano-3-(trifluoromethyl)phenyl)-3-(4-cyanophenoxy)-2-hydroxy-2-methylpropanamide as a colorless solid (a cotton type). $^1$H NMR (CDCl$_3$/TMS) δ 1.63 (s, 3H, CH$_3$), 3.35 (s, 1H, OH), 4.07 (d, J=9.04 Hz, 1H, CH), 4.51 (d, J=9.04 Hz, 1H, CH), 6.97-6.99 (m, 2H, ArH), 7.57-7.60 (m, 2H, ArH), 7.81 (d, J=8.55 Hz, 1H, ArH), 7.97 (dd, J=1.95, 8.55 Hz, 1H, ArH), 8.12 (d, J=1.95 Hz, 1H, ArH), 9.13 (bs, 1H, NH). Calculated Mass: 389.10, [M-H]$^-$ 388.1. Mp: 92-94° C.

Example 2: Crystallization of S-1 SARM Compound

Materials and Methods
Methods:
X-Ray Powder Diffraction (XRPD)

XRPD was used for the determination of the crystal structure or recognition of liquid crystals materials in partially crystalline mixtures. XRPD was performed with PANalytical X-ray diffractometer PW 1710, where the tube anode was Cu with Kα radiation. The pattern was collected in step scan mode (step size of 0.02 °2θ, counting time 2.4 s/step. The sample was measured without any special treatment other than the application of slight pressure to get a flat surface. The measurements were performed at an ambient air atmosphere.

Raman Spectroscopy

FT-Raman spectra were recorded on a Bruker RFS 100 FT-Raman system with a near infrared Nd:YAG laser operating at 1064 nm and a liquid nitrogen-cooled germanium detector. For each sample, 64 scans with a resolution of 2 cm$^{-1}$ were accumulated. The laser power used was at 100 mW. Raman measurements were conducted using aluminum sample holders or hermetically closed glass tubes at room temperature.

Thermo Gravimetric-FourierTransform Infrared (TG-FTIR) and Thermo Gravimetric Analysis The TG-FTIR instrument consists of a thermogravimetric analyzer (TG) coupled with a Fourier-Transform Infrared (FTIR) spectrometer for the analysis of evolved gases such as gases of $H_2O$, by their mass loss combined with characterization of the evolved components. Thermo gravimetric measurements were carried out with a Netzsch Thermo-Microbalance TG 209 coupled to a Bruker FTIR Spectrometer Vector 22. Sample pans with a pinhole were used under an $N_2$ atmosphere, at a heating rate of 10 K/min, with a temperature range of 25 to 250° C. Additional Thermo Gravimetric Analysis was conducted using a TA Instruments Q500 TGA under various conditions.

Differential Scanning Calorimetry (DSC)

Thermal analysis was carried out with a Perkin Elmer DSC7 with the following experimental conditions: 3 to 6 mg sample mass, closed gold sample pan, temperature range −50° C. to 120° C., heating rate 20 K/min. The samples were weighed in air or dry $N_2$ atmosphere. Additional thermal analysis was conducted using a TA Instruments Q1000 DSC using hermetic aluminum pans under various conditions.

Dynamic Vapor Sorption (DVS)

Dynamic vapor sorption quantification relates the mass of water absorbed and subsequently desorbed during the crystallization process. In order to define whether batch P1, P2 and P4 are hydrated polymorphs, DVS measurements were conducted (FIG. 9). A sample (13 to 14 mg) was placed on a Pt pan, and the sample was allowed to equilibrate at 25° C./50% r.h. before starting a pre-defined humidity program (1.0 hours 50%, from 50% r.h. to 95% r.h.: 5% r.h./hour, 10 hours at 95% r.h., from 95% r.h. to 0% r.h.: 5% r.h./hour, 10 hours at 0% r.h., from 0% r.h. to 50% r.h.: 5% r.h./hour, 1 hours at 50% r.h.

Scanning Electron Spectroscopy (SEM)

Images of S-1 batch P1, P2 and P4 (FIG. 8) were taken with an SEM CamScan CS24 system.

Filtration

During the following experiments: suspension equilibration, precipitation experiment, recrystallization, relative stability experiments and water solubility experiment, a filtration step was conducted. Centrifugal filter devices: Ultrafree-CL (0.22 la,m), Millipore; Centrifuge type or Eppendorf 5804R were used at a temperature of 22° C. and centrifugation program of 2 min 3000 rpm.

High Performance Liquid Chromatography (HPLC)

HPLC was used to analyse the purity of S-1. HP 1090M HPLC machine was used with the following conditions:
Column: Symmetry Shield RP18, 3.9×150 mm, 5 μm
Column temperature: 35° C.
Injection volume: 10 μL
Solvent: acetonitrile+water 1:1 v/v
Mobile phase A: 0.1% TFA—water
Mobile phase B: 0.1% TFA—acetonitrile Flow rate: 1 mL/min.
Detection: UV at 271 nm
Run time: 21 min.
Retention time (S-1): 10.7 min.
Materials:
Solvents
For all experiments, Fluka or Merck grade solvents were used. Water: deionized (Fluka no. 95305)
Chemicals
Compound S-1 was synthesized as described in Example 1.
Results:
Four batches of S-1 compound designated accordingly, (S-1-P1), (S-1-P2), (S-1-P3), and (S-1-P4) were selected for characterization. S-1-P1, S-1-P2, and S-1-P3 were individual batches prepared by the synthetic process described in Example 1. Batch S-1-P4 was a sample of batch S-1-P1 exposed to 40 C/75% r.h. during storage. The following experiments were conducted to determine the stability, solubility and characteristics of different solid forms of S-1 compound.

Figure 4A:
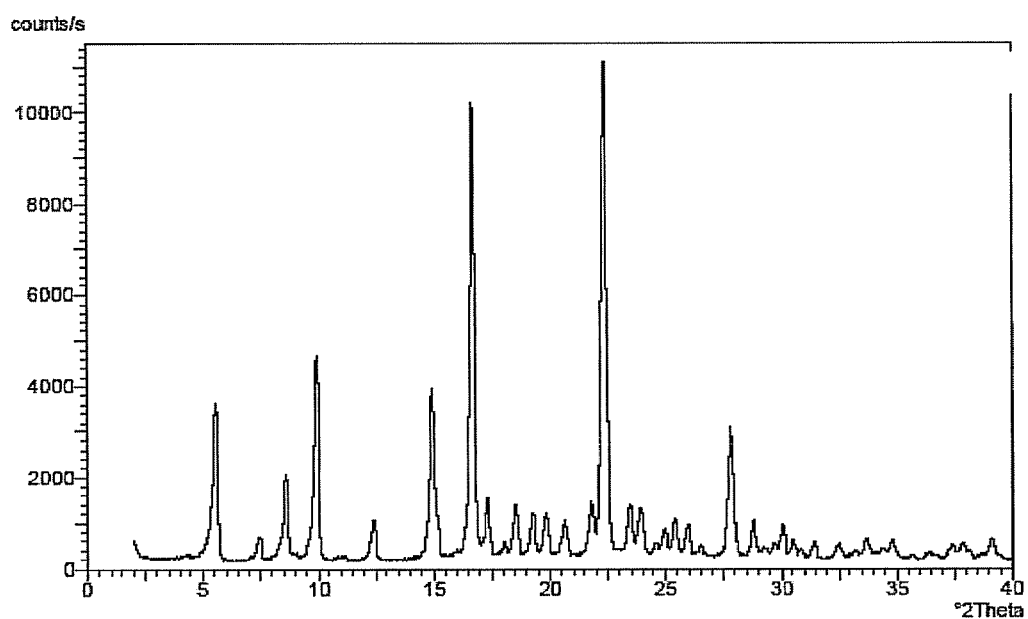
FIG. 4A-FIG. 4D depict XRPD patterns for solid forms of Compound S-1.
Figure 4B:
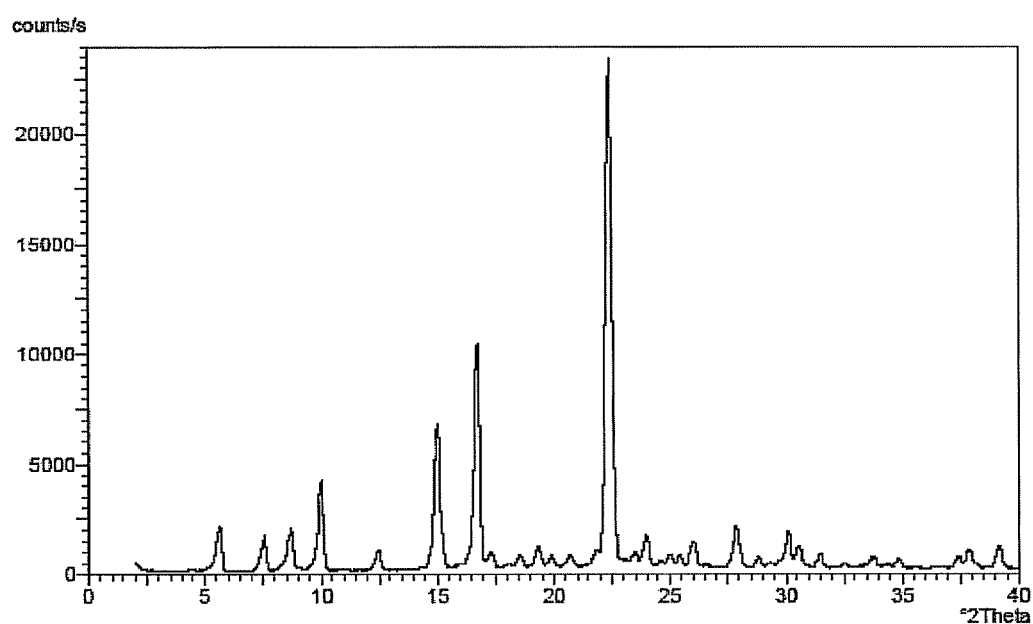
Figure 4C:
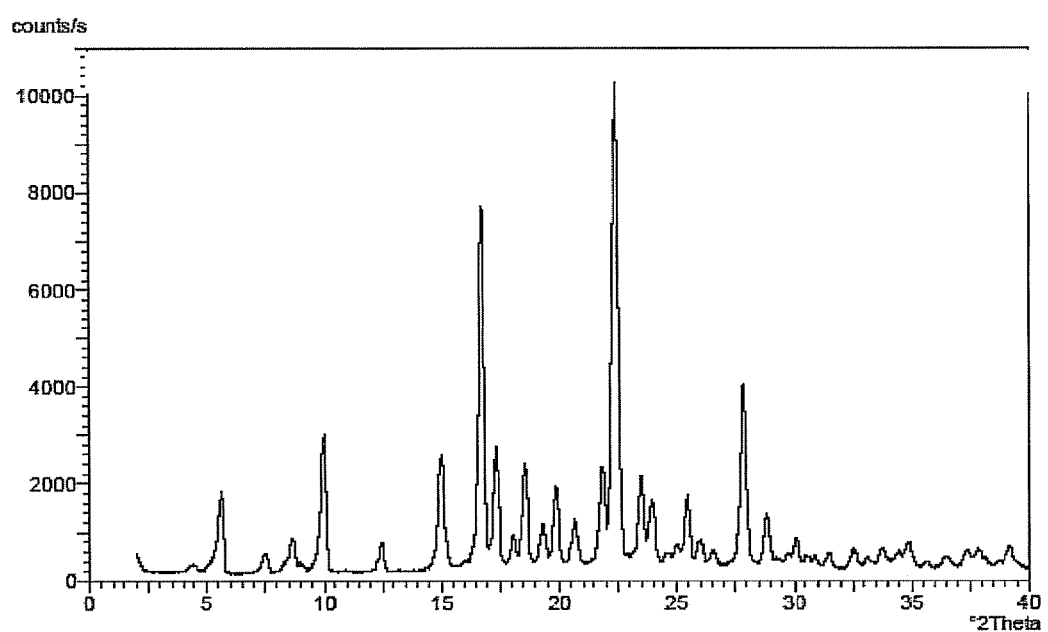

The following table presents the X-ray diffraction results of form A of S-1 as depicted in FIG. 4A:

| Angle 2-Theta ° | d value Angstrom | Intensity Cps | Intensity % |
| --- | --- | --- | --- |
| 5.56 | 15.9 | 2250 | 30 |
| 7.47 | 11.8 | 470 | 6 |
| 8.61 | 10.3 | 1399 | 19 |
| 9.93 | 8.9 | 3016 | 40 |
| 12.41 | 7.1 | 707 | 9 |
| 14.94 | 5.93 | 2647 | 35 |
| 16.66 | 5.32 | 6922 | 92 |
| 17.31 | 5.12 | 1049 | 14 |
| 18.03 | 4.92 | 397 | 5 |
| 18.52 | 4.79 | 930 | 12 |
| 19.25 | 4.61 | 830 | 11 |
| 19.83 | 4.47 | 823 | 11 |
| 20.63 | 4.30 | 740 | 10 |
| 21.80 | 4.07 | 988 | 13 |
| 22.33 | 3.98 | 7557 | 100 |
| 23.45 | 3.79 | 976 | 13 |
| 23.92 | 3.72 | 914 | 12 |
| 24.56 | 3.62 | 376 | 5 |
| 24.92 | 3.57 | 589 | 8 |
| 25.39 | 3.51 | 774 | 10 |
| 25.95 | 3.43 | 618 | 8 |
| 26.50 | 3.36 | 353 | 5 |
| 27.79 | 3.21 | 2123 | 28 |
| 28.80 | 3.10 | 734 | 10 |
| 29.68 | 3.01 | 410 | 5 |
| 30.07 | 2.97 | 656 | 9 |
| 30.49 | 2.93 | 423 | 6 |
| 31.42 | 2.84 | 391 | 5 |
| 32.49 | 2.75 | 330 | 4 |
| 33.66 | 2.66 | 431 | 6 |
| 34.78 | 2.58 | 444 | 6 |

Figure 12A:
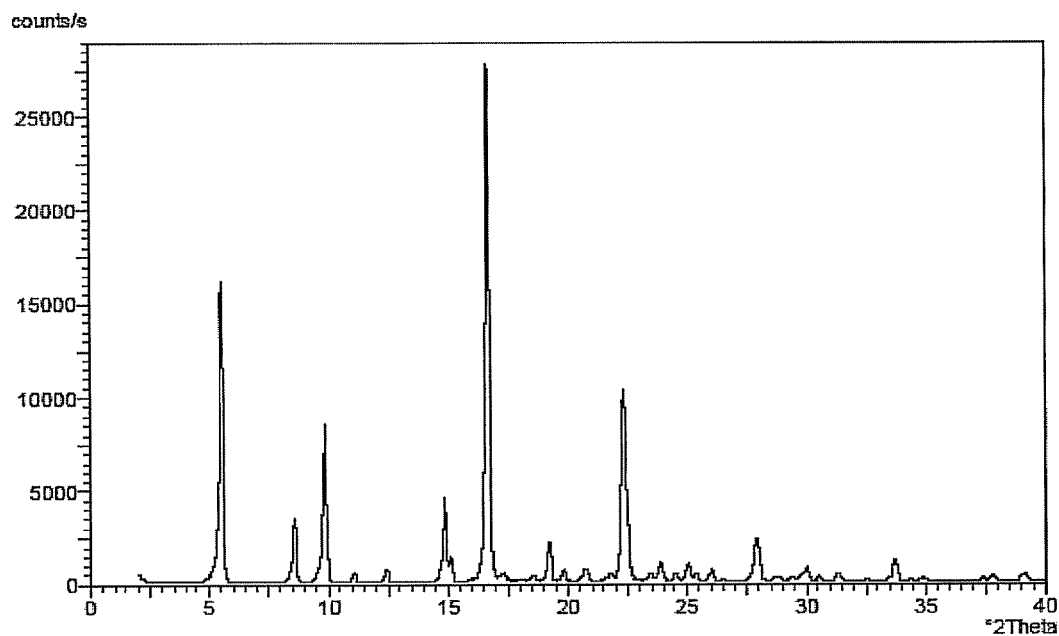
FIG. 12A-FIG. 12D shows the XRPD pattern representing the results of evaporation experiment wherein solutions of compounds were dried at room temperature (dry N$_2$ flow) without stirring.
Figure 12B:
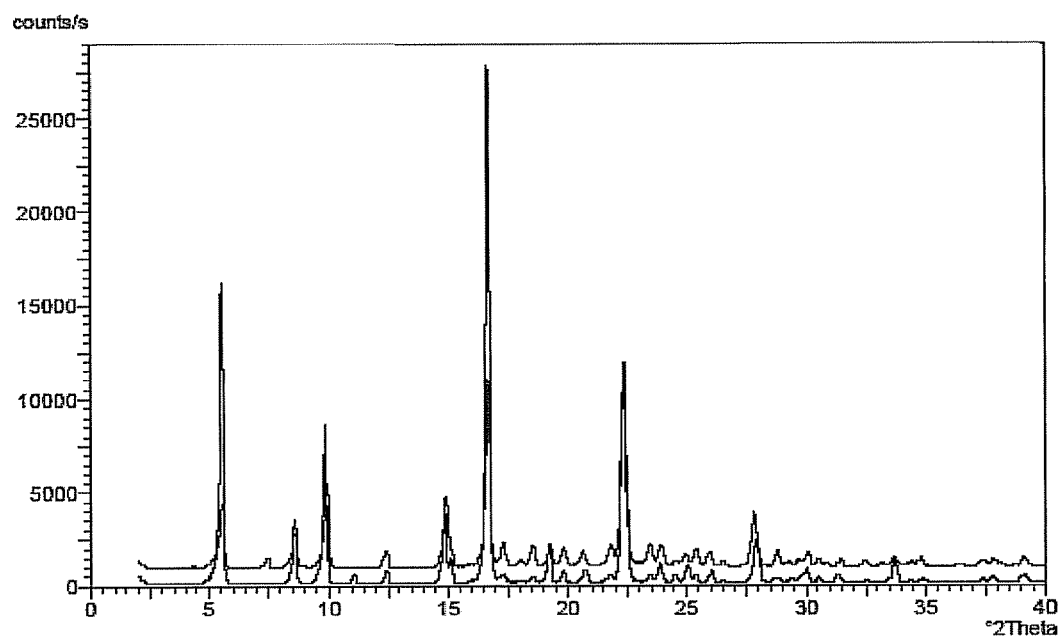
Figure 12C:
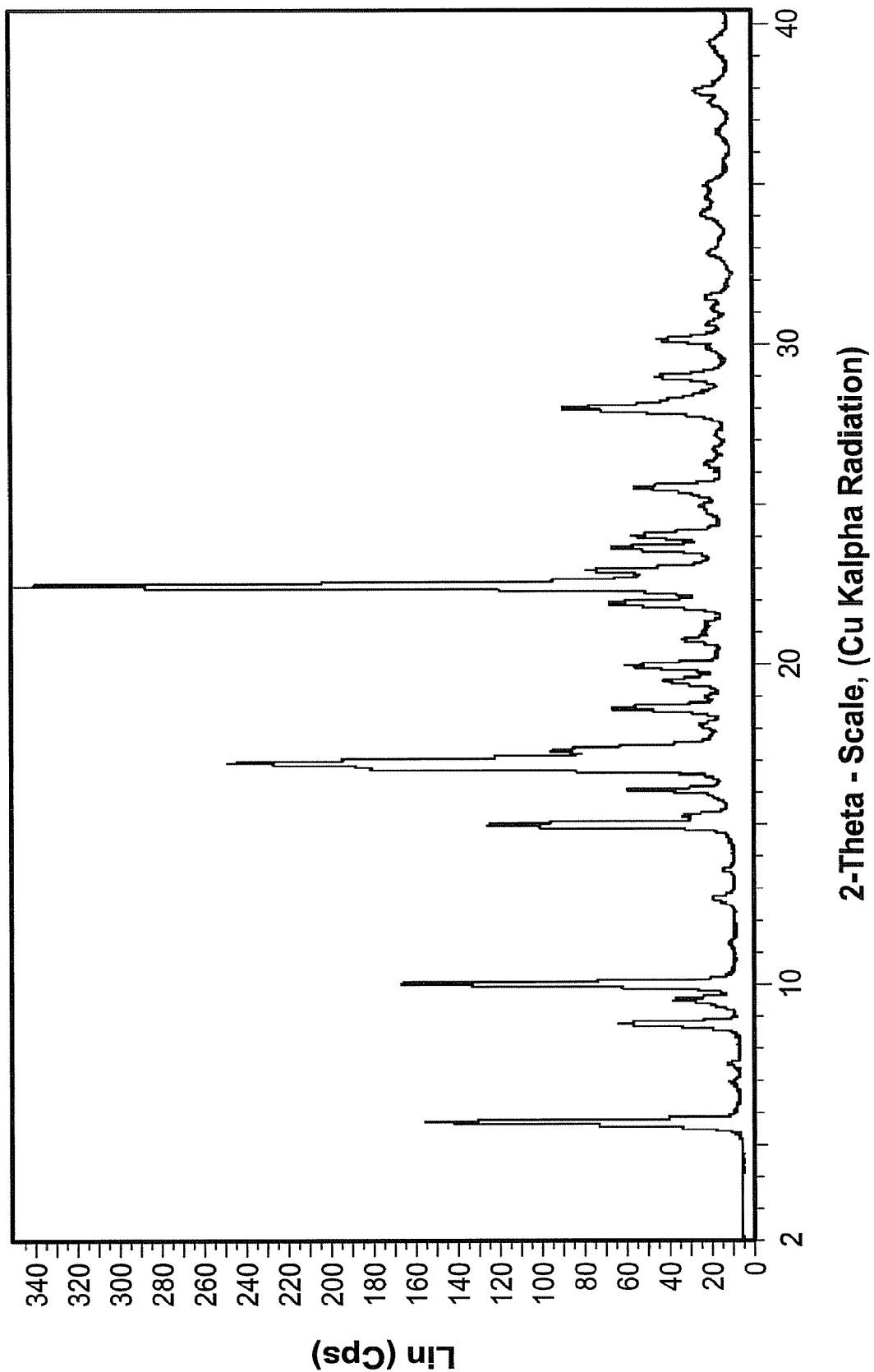
Figure 12D:
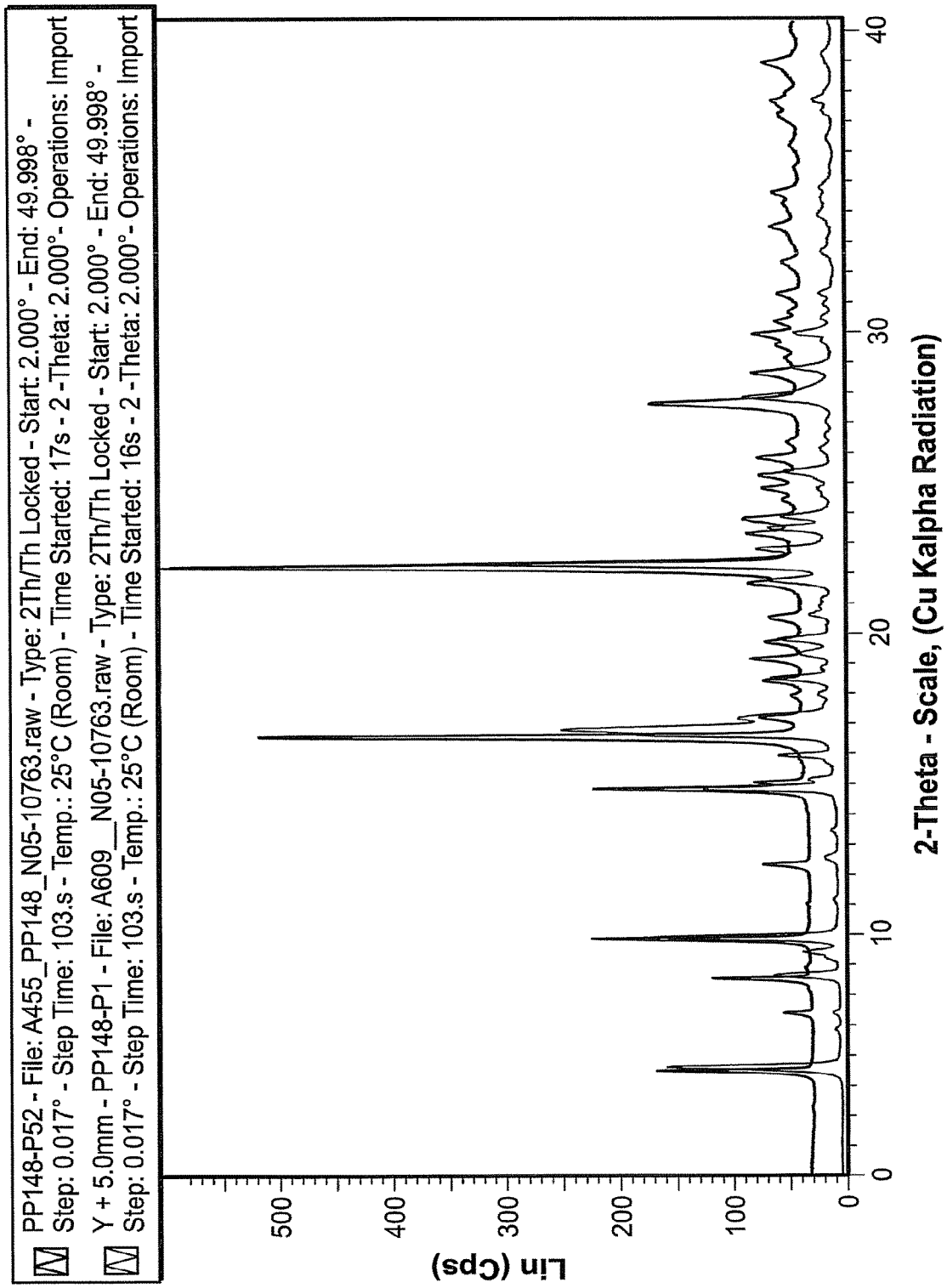
Figure 13A:
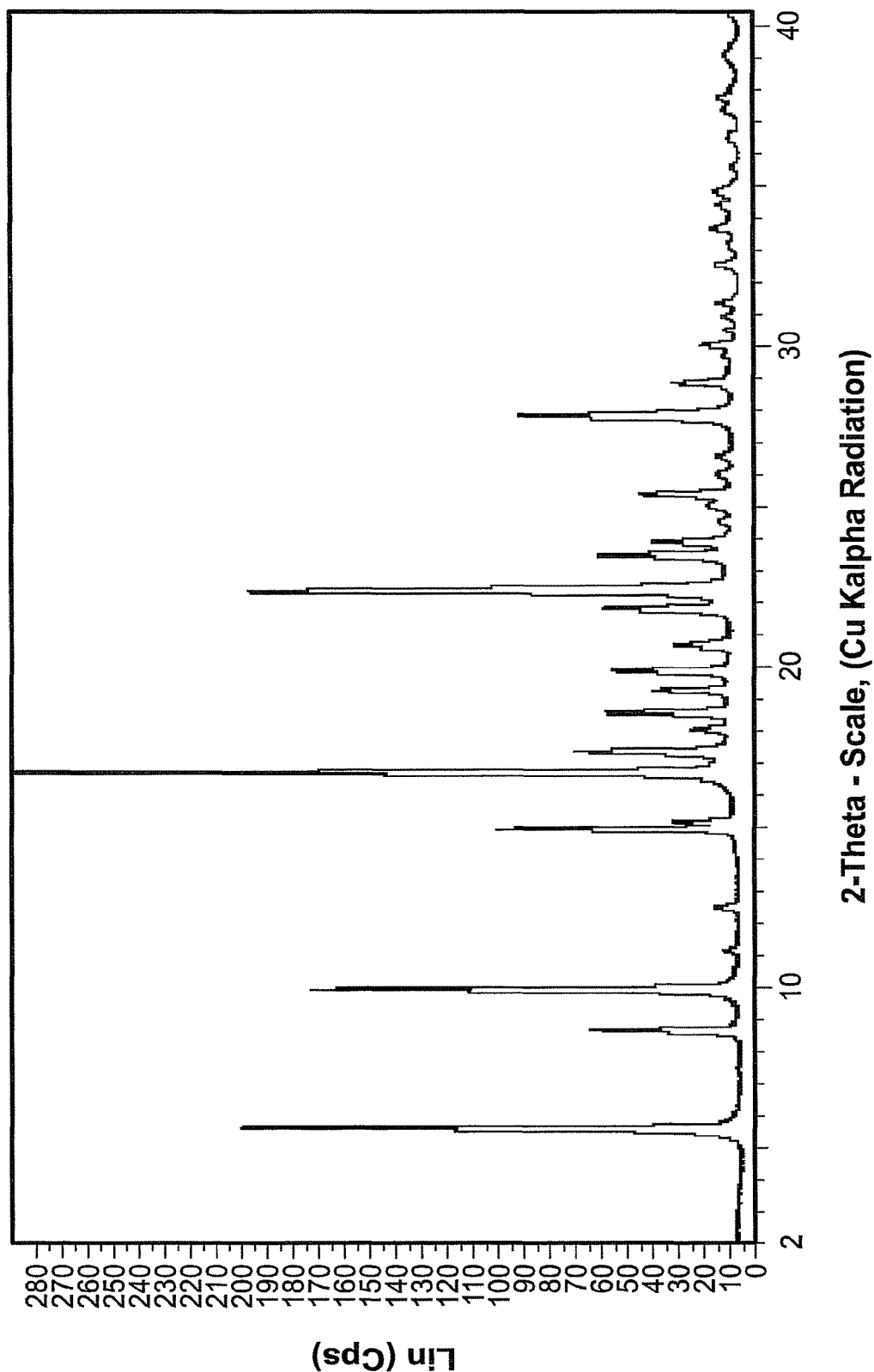
FIG. 13A-FIG. 13D shows the XRPD spectra representing the results of recrystallization from solution experiment wherein compound S-1 was dissolved in different solvent system at room temperature and cooled to +5° C. or to −20° C.
Figure 13B:
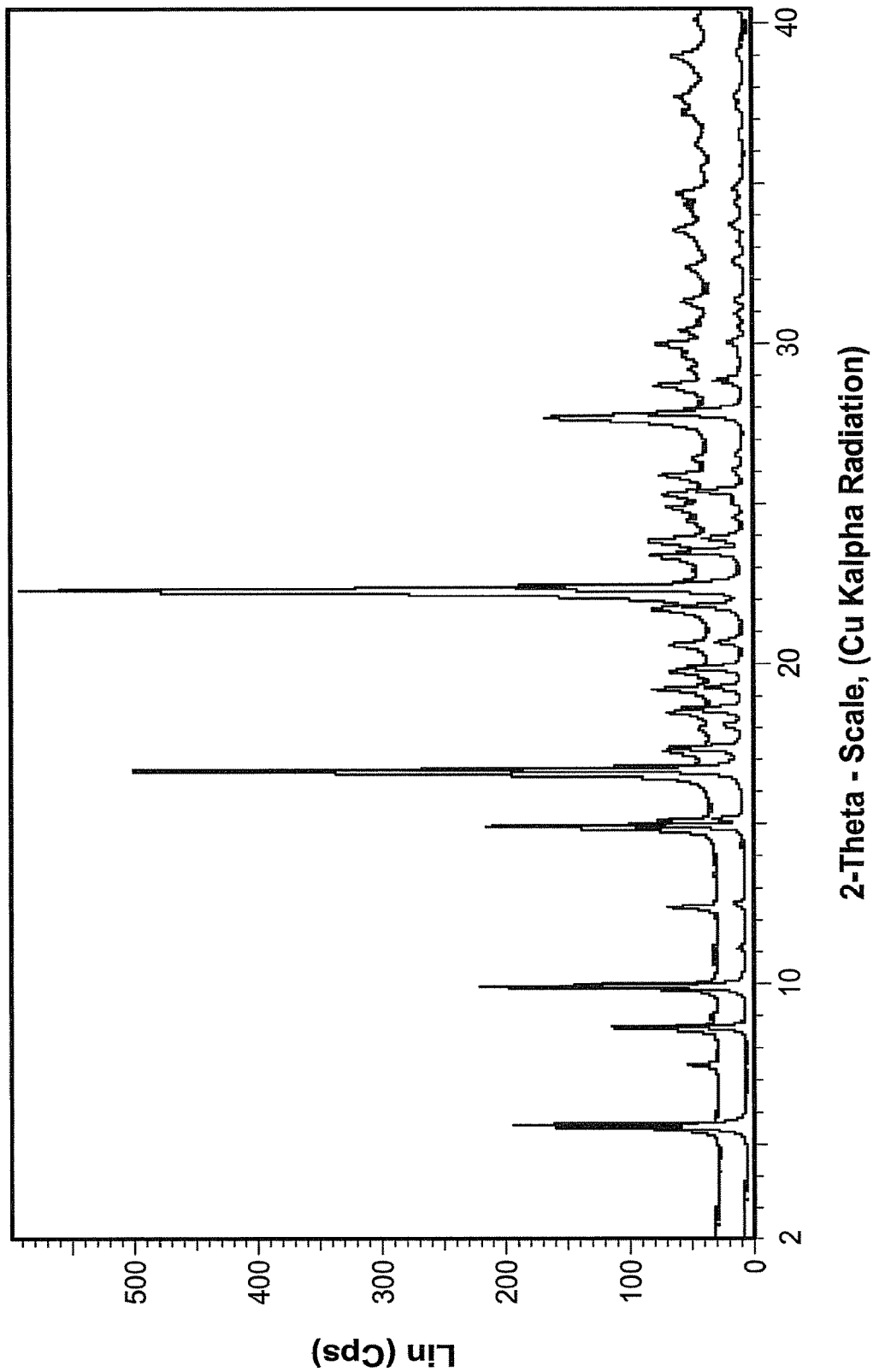
Figure 13C:
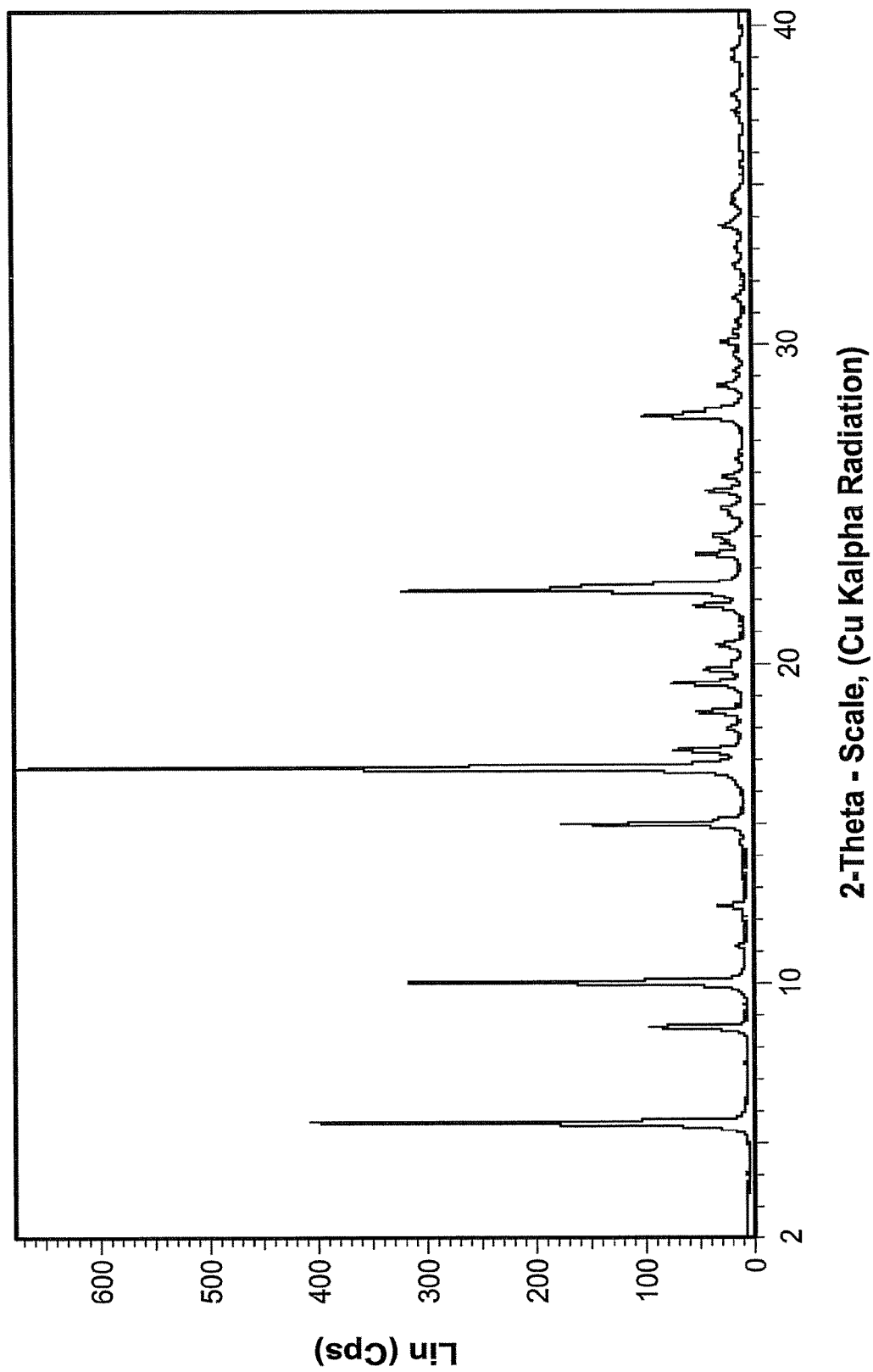
Figure 13D:
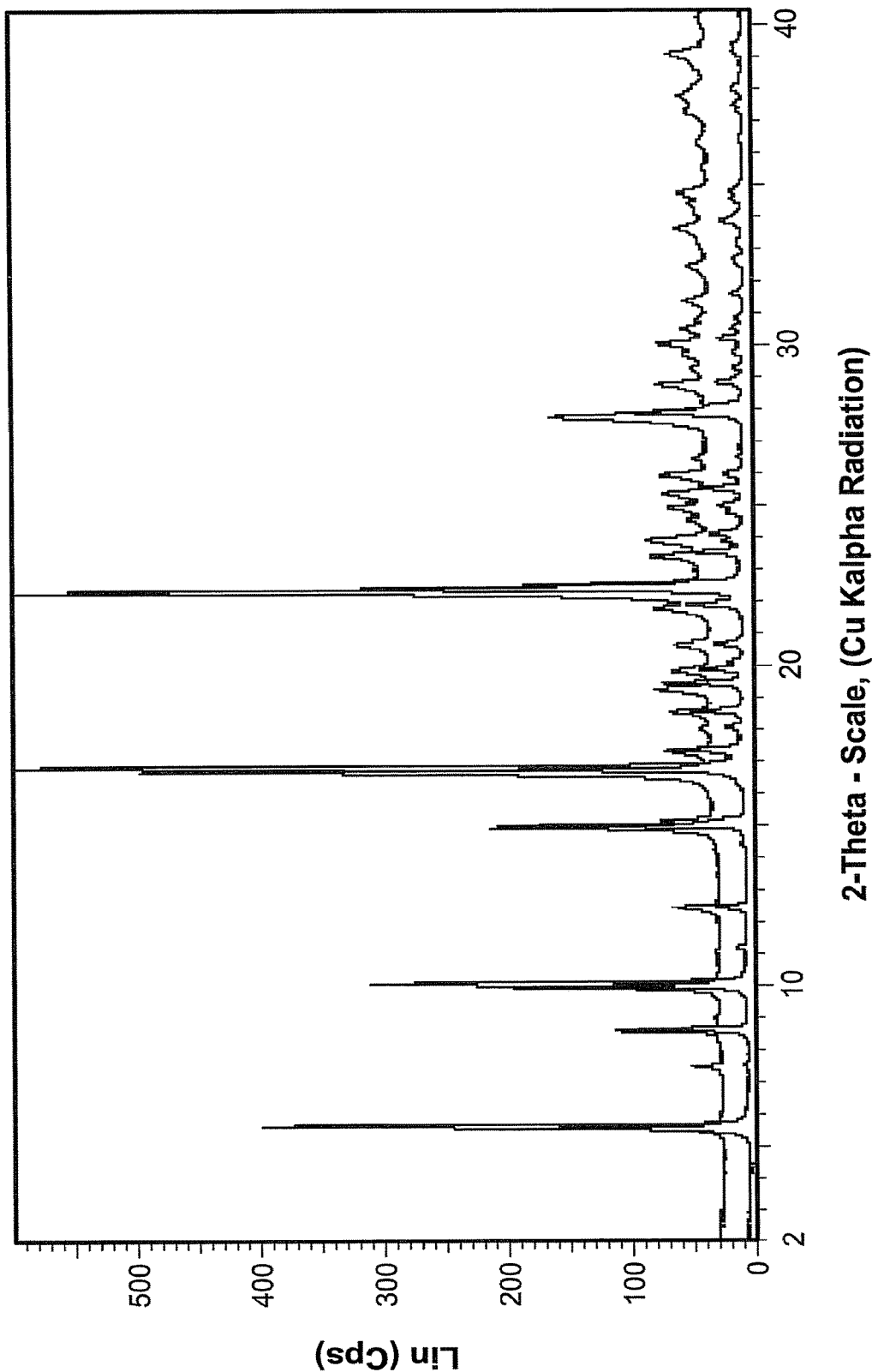
Figure 14A:
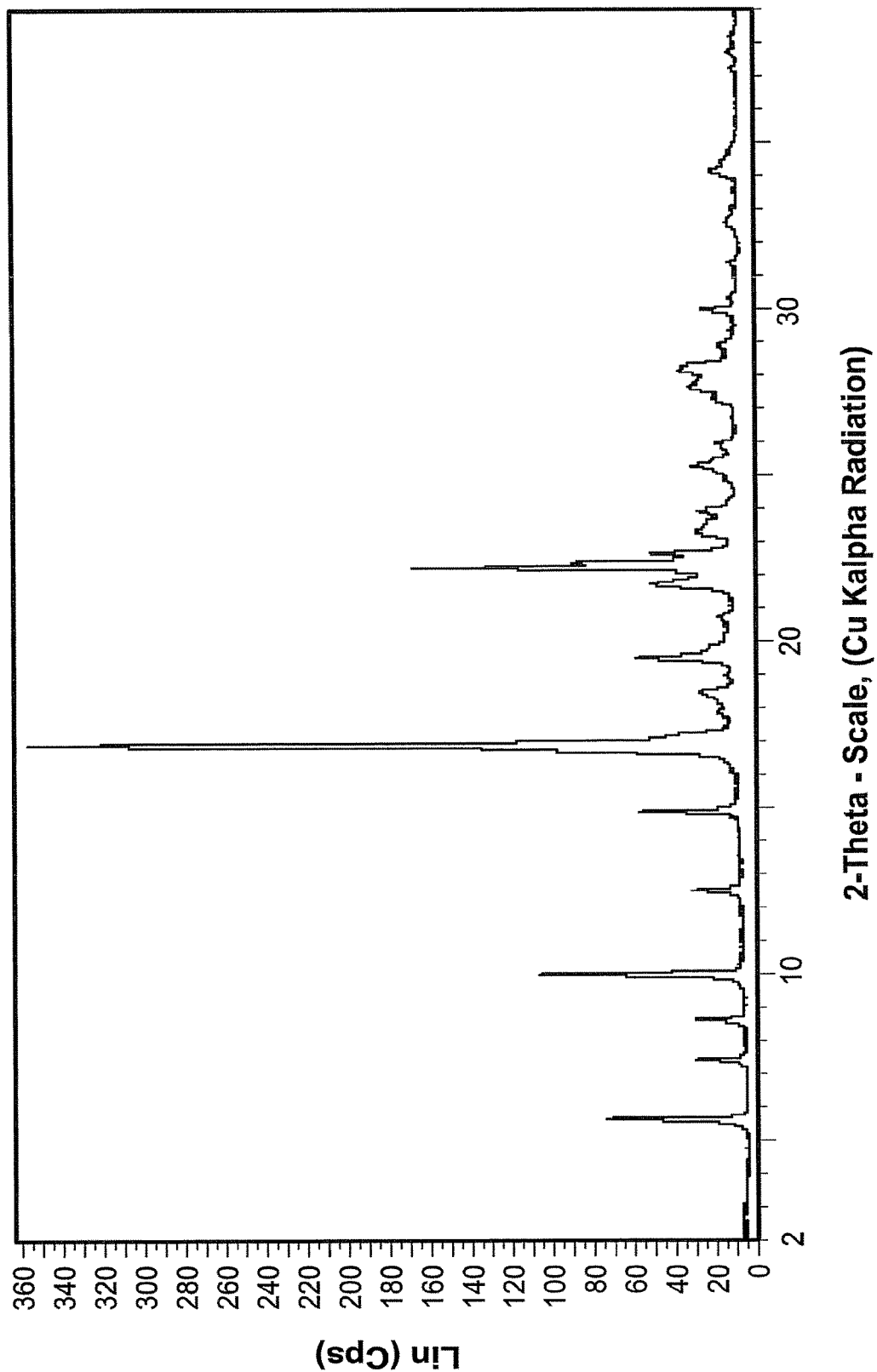
FIG. 14A-FIG. 14B shows the XRPD spectra representing the results of freeze drying experiment.
Figure 14B:
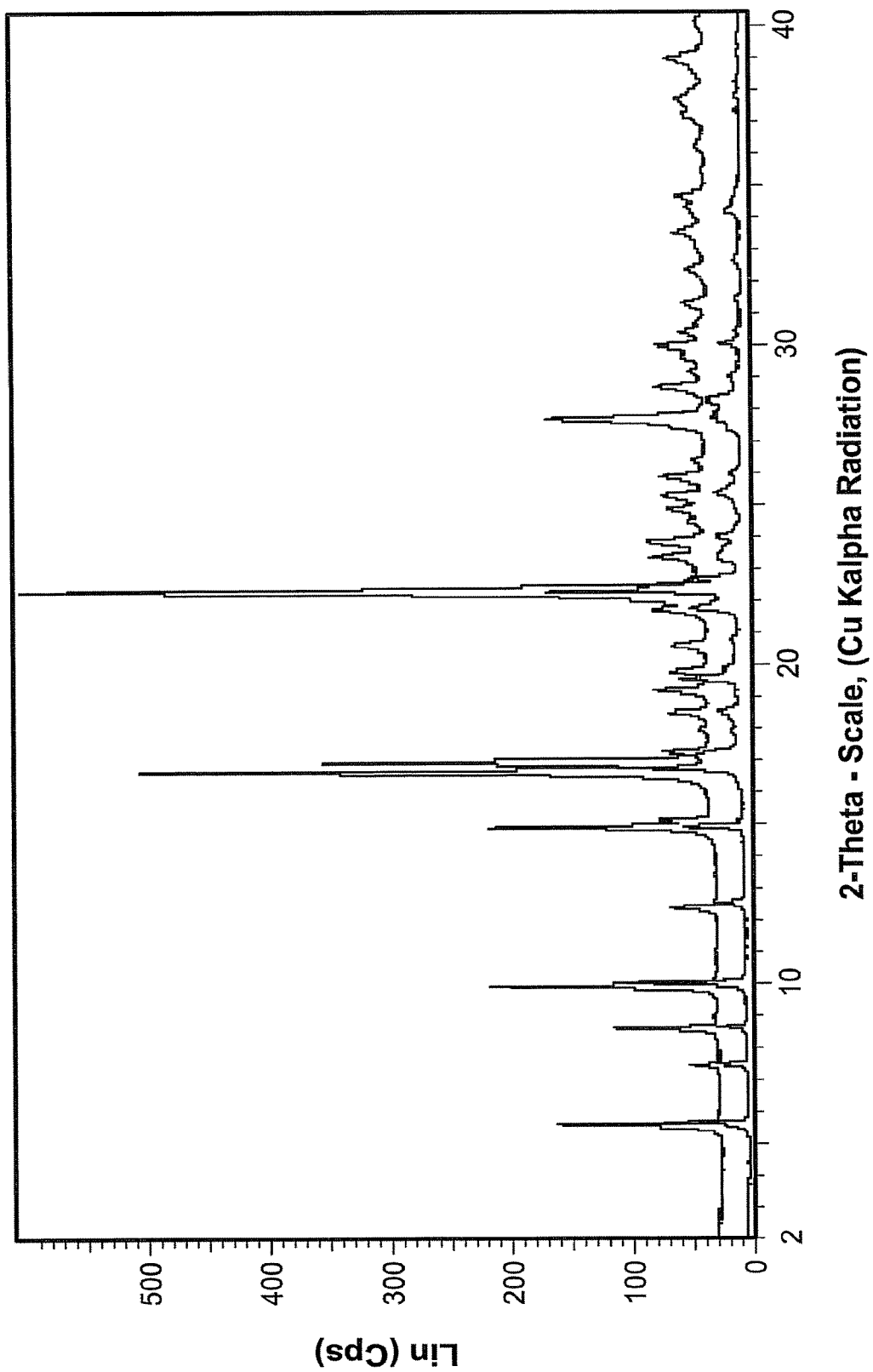
Figure 15:
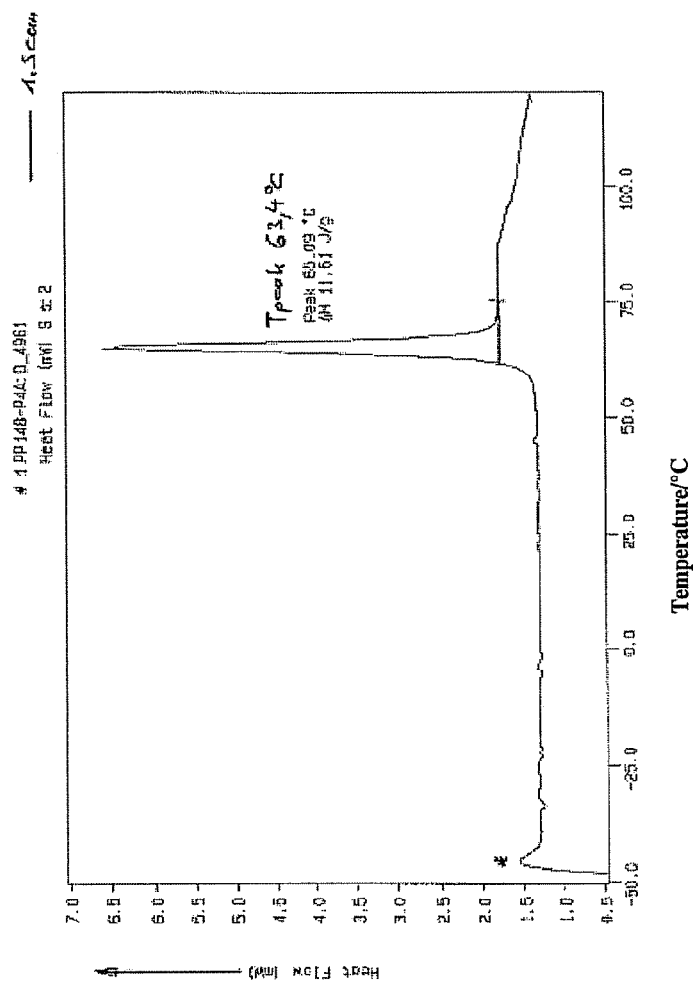
FIG. 15 demonstrates a DSC thermogram representing the results of a drying experiment when compound S-1 (batch P4) was dried overnight in a dry N$_2$ atmosphere. The asterisk indicates a settling effect, an artifact of the machinery used.
Figure 16A:
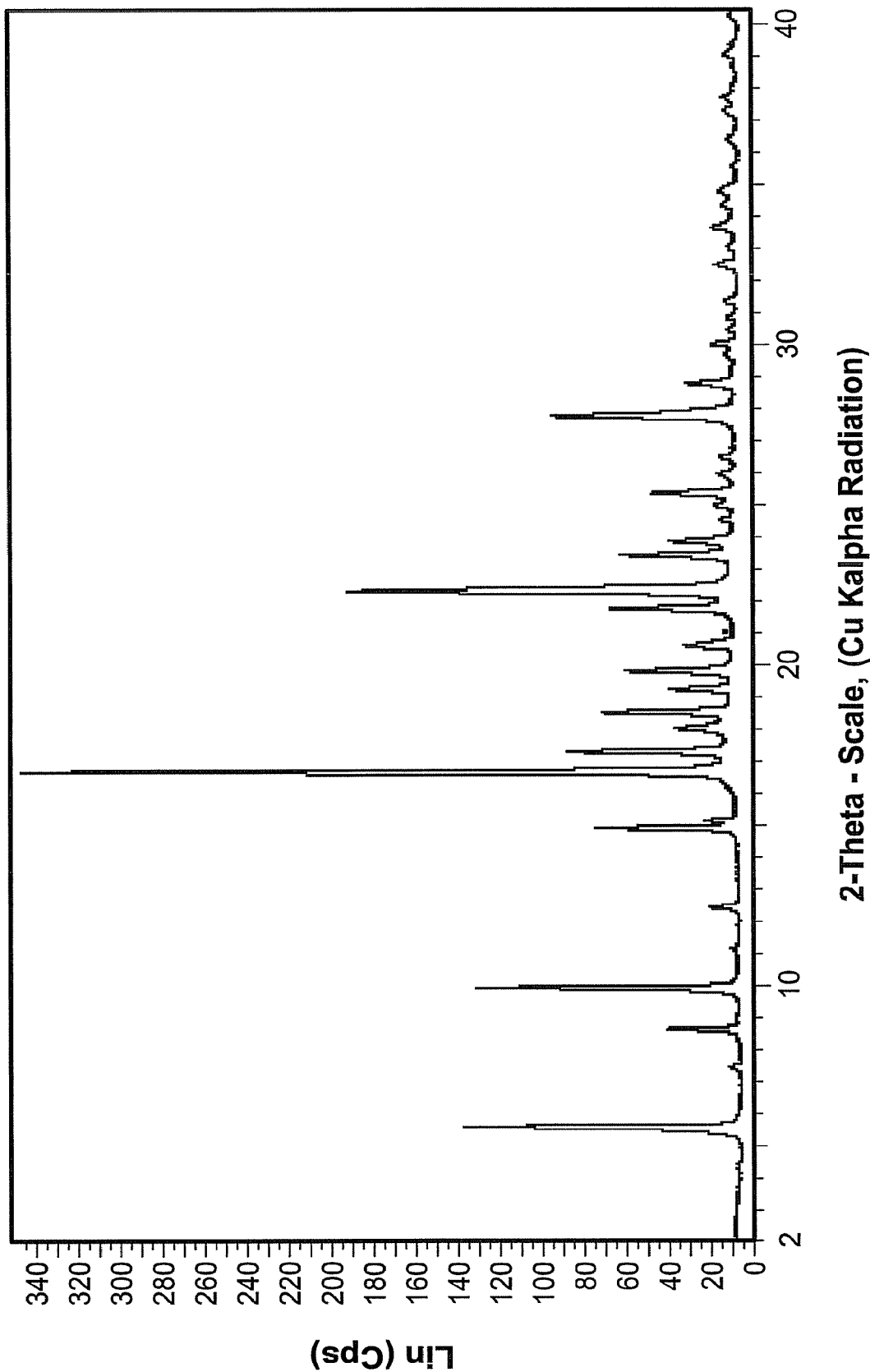
FIG. 16A-FIG. 16D demonstrates XRPD spectra representing the results of relative stability experiments wherein suspension experiments were carried out with mixtures of batches of S-1.
Figure 16B:
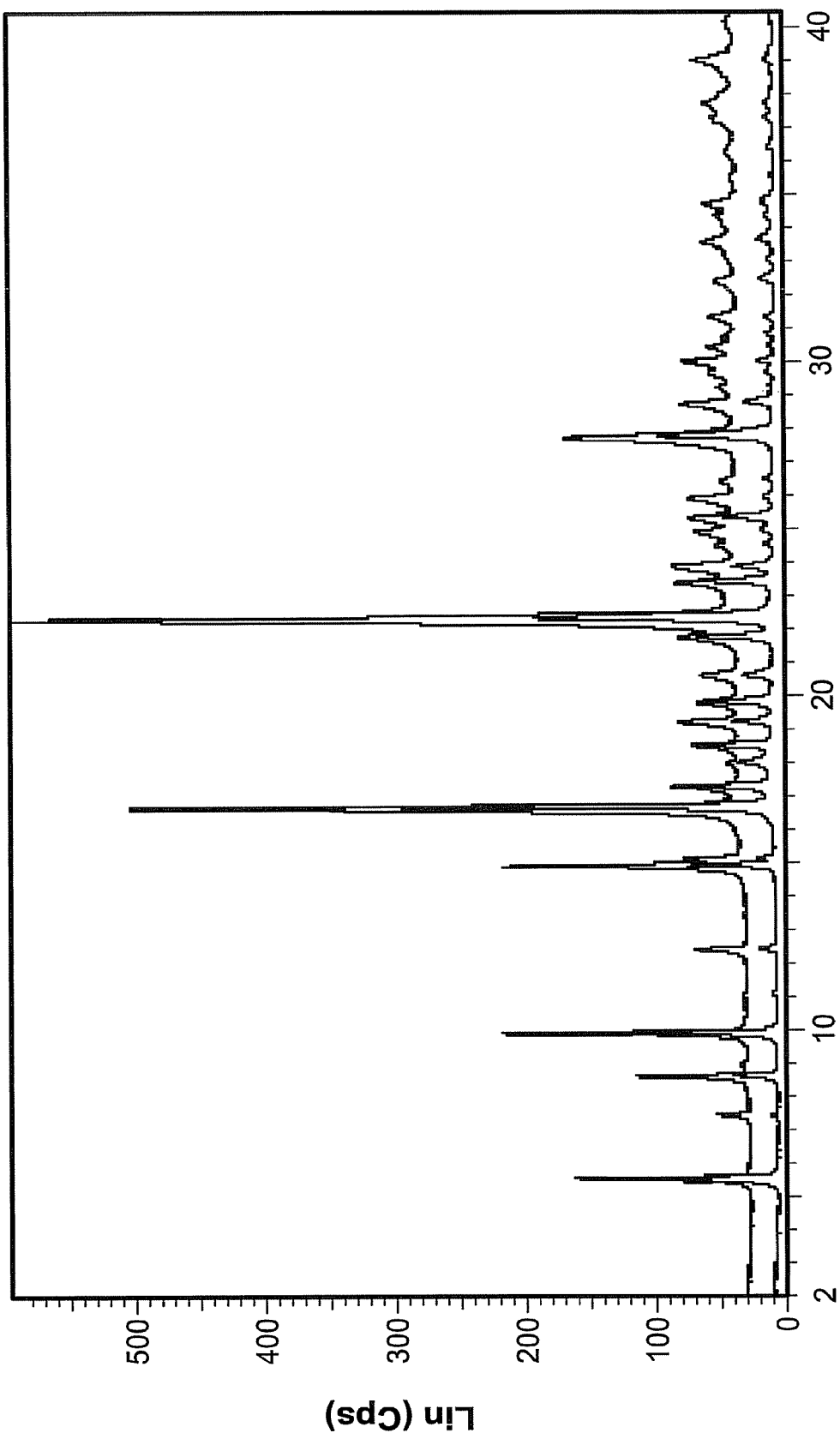
Figure 16C:
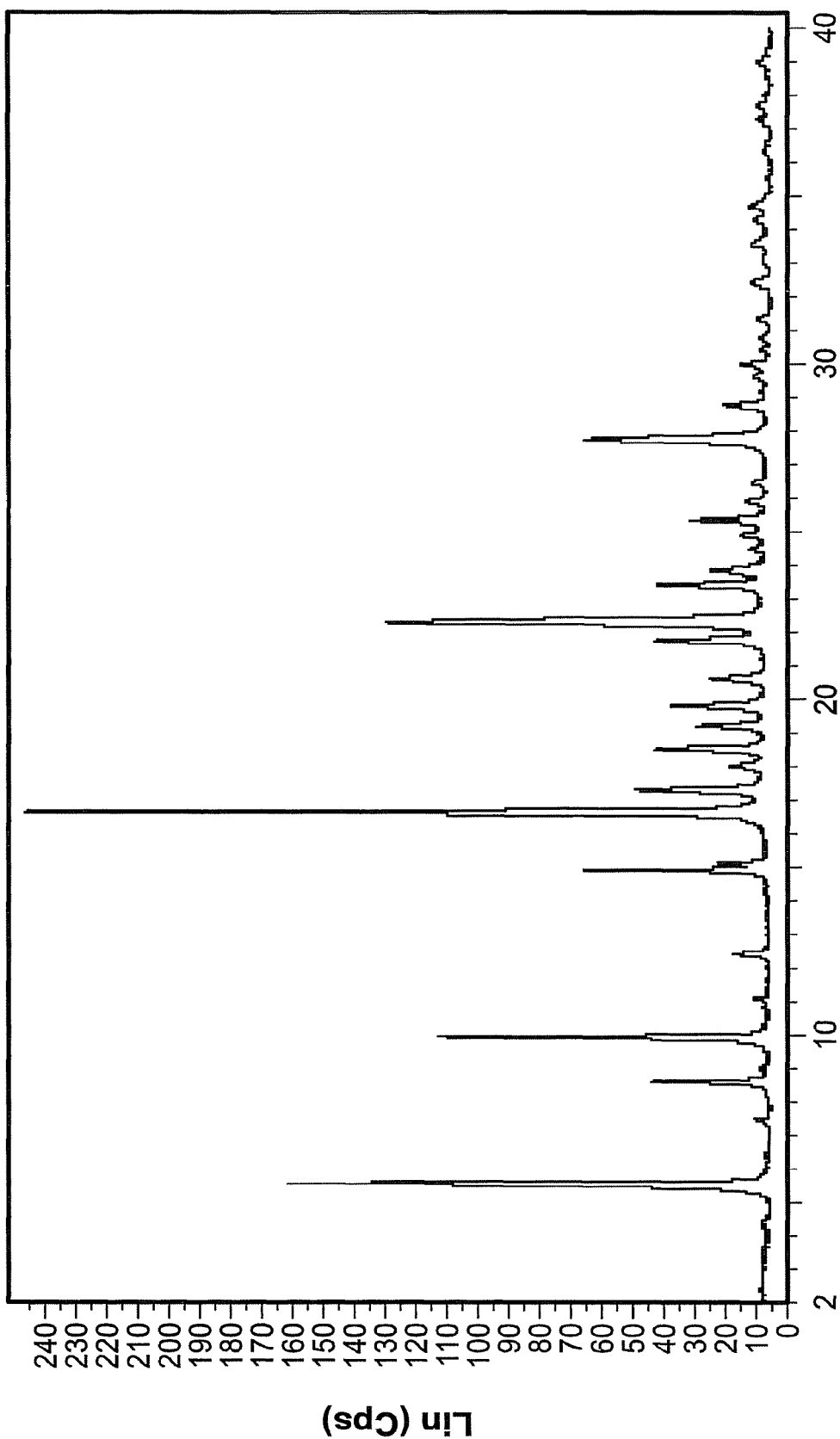
Figure 16D:
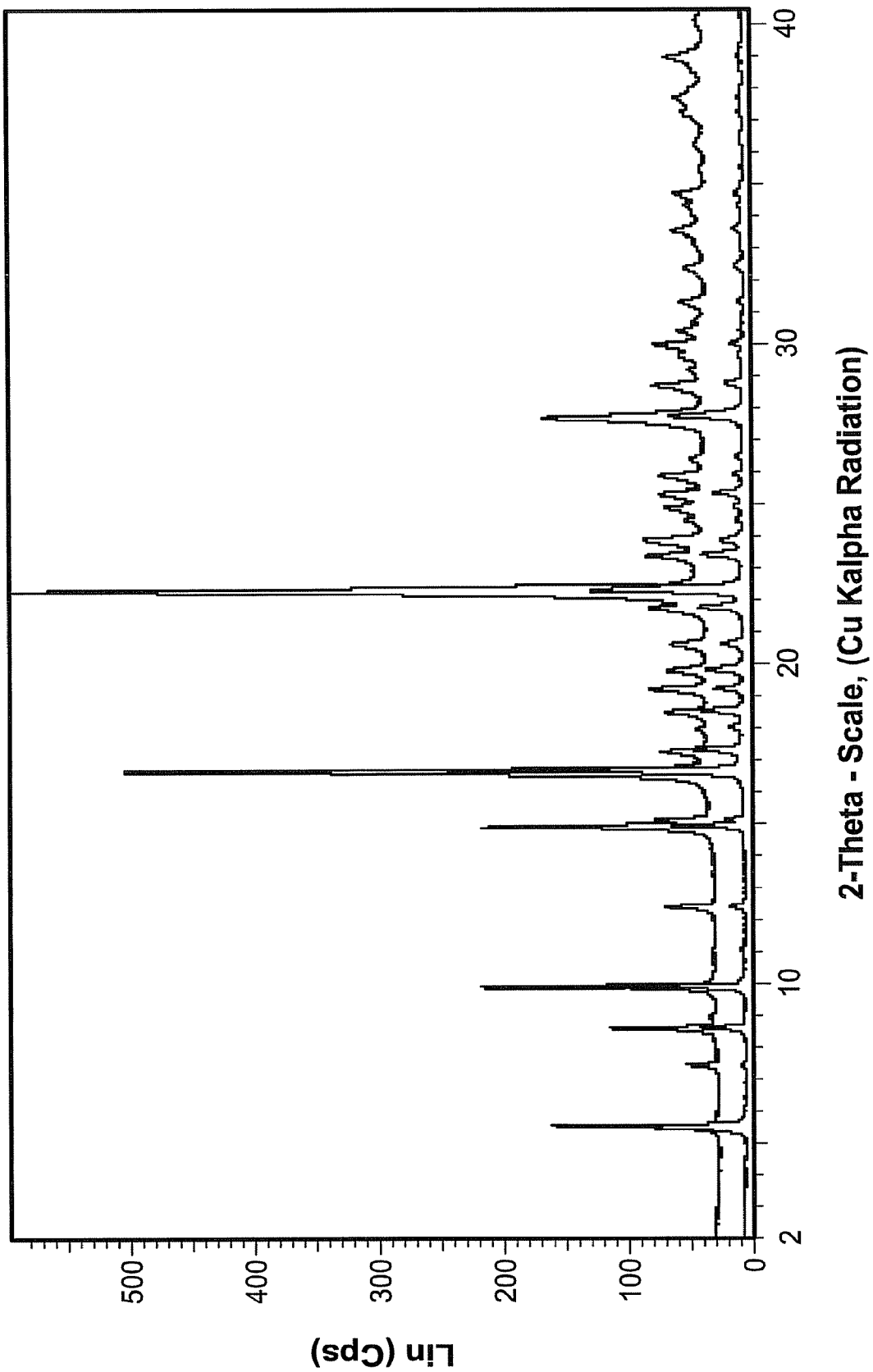

The following table presents the X-ray diffraction results of form A+C of S-1 as depicted in FIG. 12D, wherein the diffraction angles of form C were identified:

| | Mixture Form A with Form C | | | |
| --- | --- | --- | --- | --- |
| Peak Assignment not form A line | Angle 2-Theta ° | d value Angstrom | Intensity Cps | Intensity % |
| | 5.65 | 15.6 | 100 | 41 |
| certain | 6.89 | 12.8 | 7 | 3 |
| | 7.43 | 11.9 | 8 | 3 |
| | 8.68 | 10.2 | 42 | 17 |
| probable | 9.46 | 9.3 | 25 | 10 |
| | 9.94 | 8.9 | 111 | 45 |
| | 11.20 | 7.9 | 7 | 3 |
| | 12.60 | 7.0 | 12 | 5 |
| certain | 13.49 | 6.6 | 9 | 4 |
| | 14.89 | 5.95 | 82 | 33 |
| | 15.17 | 5.84 | 22 | 9 |
| Probable | 15.99 | 5.54 | 41 | 17 |
| | 16.84 | 5.26 | 164 | 67 |
| | 17.21 | 5.15 | 64 | 26 |
| | 18.00 | 4.92 | 17 | 7 |
| | 18.54 | 4.78 | 45 | 18 |
| | 19.37 | 4.58 | 27 | 11 |
| | 19.86 | 4.47 | 39 | 16 |
| | 20.66 | 4.29 | 21 | 9 |
| | 21.79 | 4.08 | 46 | 19 |
| | 22.36 | 3.97 | 246 | 100 |
| certain | 22.84 | 3.89 | 52 | 21 |
| | 23.53 | 3.78 | 46 | 19 |
| | 23.91 | 3.72 | 38 | 15 |
| | 24.84 | 3.58 | 16 | 7 |
| | 25.41 | 3.50 | 37 | 15 |
| | 26.15 | 3.41 | 14 | 6 |
| | 26.60 | 3.35 | 12 | 5 |
| | 27.89 | 3.20 | 60 | 24 |
| | 28.86 | 3.09 | 31 | 13 |
| | 30.01 | 2.98 | 30 | 12 |
| | 30.52 | 2.93 | 14 | 6 |
| | 30.98 | 2.88 | 13 | 5 |
| | 31.34 | 2.85 | 15 | 6 |
| | 32.72 | 2.73 | 14 | 6 |
| | 33.93 | 2.64 | 15 | 6 |
| | 34.84 | 2.57 | 15 | 6 |

In one embodiment form C has additional lines which are overlaid by signals of form A.

Peak search and d-value calculation were performed with software EVA version 10, 0, 0, 0, Cu Kalpha2 was removed by software, and only lines up to 35° 2theta were listed.

The sample PP148-P1 was measured on a 0.1 mm sample holder on a PANalytical PW 1710 diffractometer.

The sample PP148-P52 was measured on a 0.1 mm sample holder on a Bruker D8 Advance diffractometer.

Figure 18:
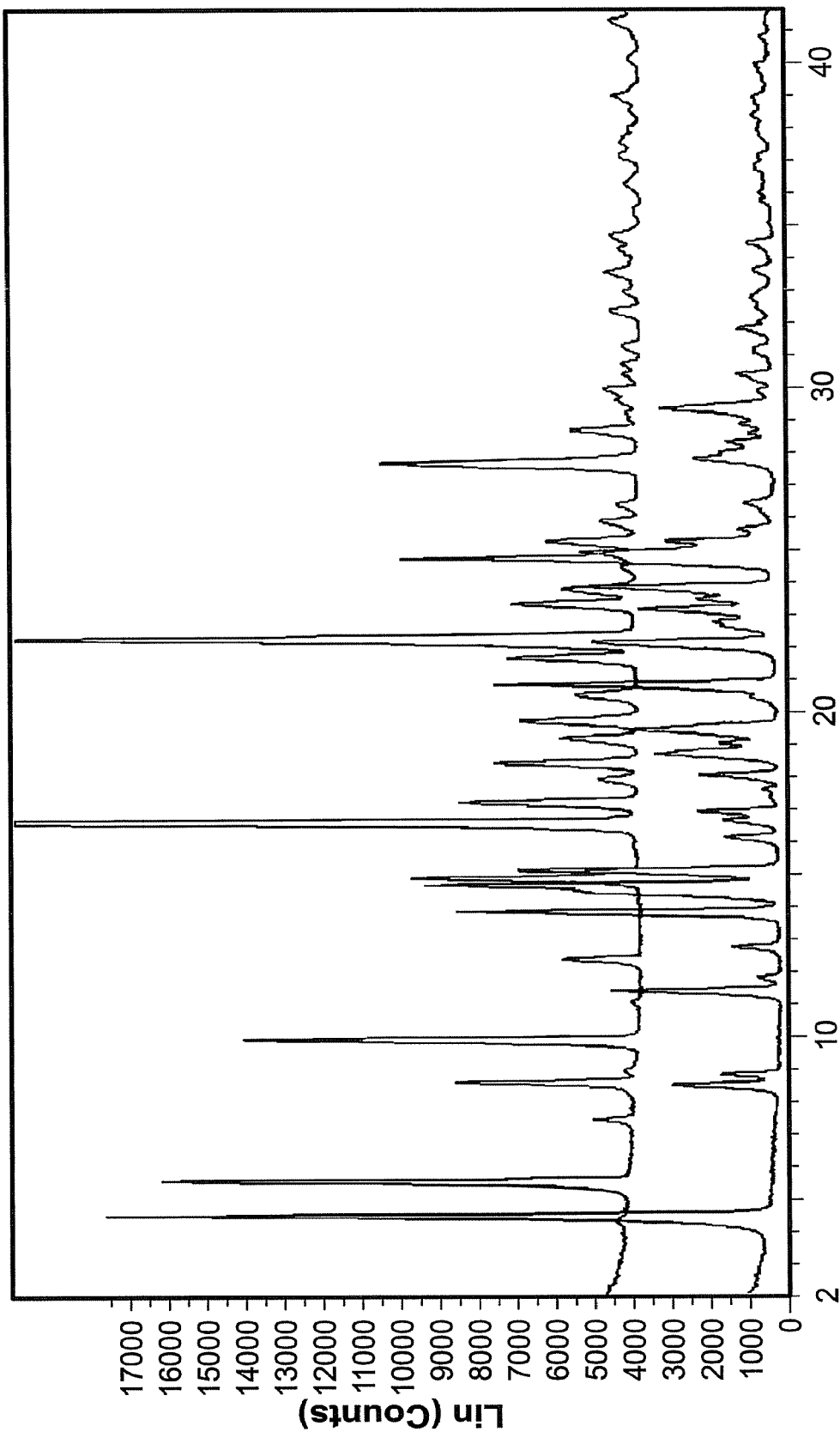
FIG. 18 demonstrates XRPD patterns of a superimposed spectra of XRPD of form A (top) and form D (bottom) of compound S-1.

The following table presents the X-ray diffraction results of form D of S-1 as depicted in FIG. 18 (bottom):

| Angle 2-Theta ° | d value Angstrom | Intensity Cps | I/Imax |
| --- | --- | --- | --- |
| 4.42 | 19.99 | 17733 | 100.0 |
| 8.48 | 10.41 | 3026 | 17.1 |
| 8.80 | 10.04 | 1755 | 9.9 |
| 11.35 | 7.79 | 4598 | 25.9 |
| 11.76 | 7.52 | 805 | 4.5 |
| 12.72 | 6.96 | 1462 | 8.2 |
| 13.84 | 6.39 | 8635 | 48.7 |
| 14.45 | 6.13 | 5597 | 31.6 |
| 14.64 | 6.05 | 9445 | 53.3 |
| 15.10 | 5.86 | 7013 | 39.5 |
| 16.14 | 5.49 | 1644 | 9.3 |
| 16.64 | 5.32 | 1678 | 9.5 |
| 16.95 | 5.23 | 2357 | 13.3 |
| 17.41 | 5.09 | 484 | 2.7 |
| 17.59 | 5.04 | 678 | 3.8 |
| 18.04 | 4.91 | 2308 | 13.0 |
| 18.71 | 4.74 | 3439 | 19.4 |
| 19.04 | 4.66 | 1824 | 10.3 |
| 19.46 | 4.56 | 4093 | 23.1 |

-continued

| Angle 2-Theta ° | d value Angstrom | Intensity Cps | I/Imax |
|---|---|---|---|
| 20.48 | 4.33 | 989 | 5.6 |
| 20.84 | 4.26 | 7616 | 42.9 |
| 22.15 | 4.01 | 5058 | 28.5 |
| 22.78 | 3.90 | 1933 | 10.9 |
| 23.15 | 3.84 | 3851 | 21.7 |
| 23.47 | 3.79 | 2352 | 13.3 |
| 23.88 | 3.72 | 5583 | 31.5 |
| 24.74 | 3.60 | 10043 | 56.6 |
| 24.94 | 3.57 | 5395 | 30.4 |
| 25.29 | 3.52 | 3149 | 17.8 |
| 25.67 | 3.47 | 1290 | 7.3 |
| 26.14 | 3.41 | 692 | 3.9 |
| 26.46 | 3.37 | 1095 | 6.2 |
| 27.80 | 3.21 | 2402 | 13.5 |
| 28.32 | 3.15 | 1565 | 8.8 |
| 28.64 | 3.11 | 998 | 5.6 |
| 28.90 | 3.09 | 1212 | 6.8 |
| 29.38 | 3.04 | 3295 | 18.6 |
| 29.92 | 2.98 | 756 | 4.3 |
| 30.40 | 2.94 | 1278 | 7.2 |
| 31.19 | 2.87 | 851 | 4.8 |
| 31.86 | 2.81 | 1270 | 7.2 |
| 32.49 | 2.75 | 775 | 4.4 |
| 32.82 | 2.73 | 920 | 5.2 |
| 33.66 | 2.66 | 842 | 4.7 |
| 34.50 | 2.60 | 977 | 5.5 |
| 35.80 | 2.51 | 638 | 3.6 |
| 36.06 | 2.49 | 700 | 3.9 |
| 36.83 | 2.44 | 777 | 4.4 |
| 37.16 | 2.42 | 698 | 3.9 |
| 38.02 | 2.36 | 733 | 4.1 |
| 38.44 | 2.34 | 859 | 4.8 |
| 38.97 | 2.31 | 844 | 4.8 |
| 39.99 | 2.52 | 791 | 4.5 |
| 40.89 | 2.21 | 641 | 3.6 |
| 41.30 | 2.18 | 515 | 2.9 |

Water Vapor Sorption (Humidity Chamber)

The compound was stored in a glass tube under 96% r.h. (relative humidity) in a humidity chamber at room temperature. After different time of storage Raman measurements were conducted using hermetically closed glass tubes. The results are summarized in Table 1:

TABLE 1

| Starting form | Solvent | Concentration mg/ml | Conditions | Form produced |
|---|---|---|---|---|
| A | | | stored in humidified chamber 96% r.h./ 23° C. | (powder) |
| | | | 4 weeks | A + small amount form B' |
| | | | 9 weeks | A + form B' |
| | | | 11 weeks | A + approx. 20% form B' (see FIG. 17A) |
| A | water | 111/5.0 | 23° C. sonication 5 min. | (suspension) (suspension) |
| | | | stirred 19 h/37° C. filtered & air dried | B' (see FIG. 17B) |
| A | water + 5% ethanol v/v | 123/2.1 | 23° C. stirred3 h/83° C. | (suspension) viscous sticky mass |

TABLE 1-continued

| Starting form | Solvent | Concentration mg/ml | Conditions | Form produced |
|---|---|---|---|---|
| | | | cooled to 47° C. within 1.5 h filtered & air dried | B' |
| A | acetic acid/ water 1:2 v/v | 138/2.0 | 23° C. stirred 20 h/23° C. filtered & air dried | (suspension) A (see FIG. 17C) |
| A | water + 5% acetic acid v/v | 105/2.0 | 23° C. stirred 12 min/ 40° C. | (suspension) (suspension) |
| | | | sonicated 2 min. | (suspension) |
| | | | stirred 17 h/40° C. cooled to R.T. and removed solution | viscous sticky mass B' |

Measurement of the Approximate Solubility

To determine the approximate solubility at room temperature, the solvent was added in steps to the solid material. After every addition, the sample was well stirred. The addition of solvent was continued until complete dissolution or until 15 ml of solvent was added. The solubility of solid form A and B' at 23° C. is presented in Table 2.

TABLE 2

| Solvent | Solid form | Solubility (mg/ml) |
|---|---|---|
| ethanol | A | >200 |
| acetone | A | >200 |
| TBME | A | >200 |
| ethyl acetate | A | >200 |
| THF | A | >200 |
| acetonitrile | A | >200 |
| dichloromethane | A | >200 |
| 1,4-dioxane | A | >200 |
| acetic acid | A | >200 |
| toluene | A | <6 turbid solution |
| ethanol/water 3:1 v/v | A | >200 |
| ethanol/water 1:1 v/v | A | 50 |
| ethanol/water 1:3 v/v | A | <5 |
| ethanol/n-heptane 1:1 v/v | A | 180 |
| ethanol/n-heptane 1:3 v/v | A | 50 |
| acetone/n-heptane 1:1 v/v | A | >200 |
| acetone/n-heptane 1:3 v/v | A | 90 |
| THF/n-heptane 1:1 v/v | A | >200 |
| THF/n-heptane 1:3 v/v | A | 65 |
| acetonitrile/toluene 1:1 v/v | A | >200 |
| acetonitrile/toluene 1:3 v/v | A | 170 |
| ethyl acetate/n-heptane 1:1 v/v | A | 65 |
| ethyl acetate/n-heptane 1:2 v/v | A | 9 |
| ethyl acetate/n-heptane 1:2 v/v | B' | >9 solid form transformation into solid form A |
| ethyl acetate/n-pentane 1:2 v/v | A | 13 |
| ethyl formate/n-pentane 1:2 v/v | A | 12 |
| methyl acetate/n-pentane 1:2 v/v | A | 8 |
| ethyl acetate/n-heptane 1:3 v/v | A | <5 turbid solution |

Suspension Equilibration Experiments

Suspension equilibration experiments were carried out with 81-128 mg of the compound. The suspensions were stirred with a magnetic stirrer. The samples obtained after filtration were air dried at ambient temperature for a short time only to prevent possible desolvation of labile hydrates or solvates. The results of the suspension equilibration experiments of solid form A and B' are presented in Table 3.

TABLE 3

| Starting form | Solvent | Concentration mg/ml | Conditions | Form produced |
|---|---|---|---|---|
| A | n-heptane | 108/2.0 | 23° C. sonicated 5 min. stirred 17 h/37° C. filtered & air dried | (suspension) (suspension) A (see FIG. 10a) |
| A | n-heptane + 5% ethanol v/v | 117/2.1 | 23° C. sonicated 5 min. stirred 18 h/37° C. filtered & air dried | (suspension) (suspension) A |
| B' | ethyl acetate + n-heptane 1:2 v/v | 81/1.7 | 23° C. stirred 2 h/23° C. filtered & air dried | (suspension) A (see FIG. 10b) |
| A | ethyl acetate + n-heptane 1:2 v/v | 124/2.0 | 23° C. stirred 3 days/23° C. filtered & air dried | (suspension) A |
| A | ethyl acetate + n-heptane 1:2 v/v | 126/2.0 | +2° C. stirred 3 days/+2° C. filtered & air dried | (suspension) A |
| B' | ethyl acetate + n-pentane 1:2 v/v | 101/1.0 | 23° C. stirred 22 h/23° C. filtered & air dried | (suspension) A (see FIG. 13c) |
| A | ethyl acetate + n-pentane 1:2 v/v | 128/2.0 | 23° C. stirred 20 h/23° C. filtered & air dried | (suspension) A (see FIG. 10d) |
| A | ethyl formate + n-pentane 1:2 v/v | 112/2.0 | 23° C. stirred 20 h/23° C. filtered & air dried | (suspension) A (see FIG. 10e) |
| A | methyl acetate + n-pentane 1:2 v/v | 126/2.0 | 23° C. stirred 20 h/23° C. filtered & air dried | (suspension) A (see FIG. 10f) |

Vapor Diffusion Experiments

Vapor diffusion experiments were carried out with solution of the compound in different solvents. The solutions were placed in small, open containers that were stored in larger vessels containing miscible, volatile antisolvents. The larger vessels were then tightly closed. The antisolvents diffused through the vapor phases into the solutions, and saturation or supersaturation was achieved. The results of the vapor diffusion experiments of solid form A and B' are presented in Table 4.

TABLE 4

| Solvent | Antisolvent | Concentration mg/ml | Conditions | Form produced |
|---|---|---|---|---|
| ethanol | n-hexane | 204 mg P1 0.4 ml solvent | vapor diffusion, 23° C., 7 days, removed solution | viscous sticky mass |
| acetone | n-hexane | 210 mg P1 0.5 ml solvent | vapor diffusion, 23° C., 7 days, removed solution | viscous sticky mass |
| TBME | n-hexane | 205 mg P1 0.6 ml solvent | vapor diffusion, 23° C., 7 day, removed solution | viscous sticky mass |
| ethyl acetate | n-hexane | 206 mg P1 0.6 ml solvent | vapor diffusion, 23° C., 2 days, filtered and air-dried | very similar to A |
| THF | n-hexane | 212 mg P1 0.6 ml solvent | vapor diffusion, 23° C., 7 days, removed solution | viscous sticky mass |
| toluene | n-hexane | 44 mg P1 2.0 ml solvent | vapor diffusion, 23° C., 2 days, removed solution | very similar to A (see FIG. 11A) |
| dichloromethane | n-hexane | 204 mg P1 1.6 ml solvent | vapor diffusion, 23° C., 2 days, removed solution | very similar to A |
| 1,4-dioxane | n-hexane | 215 mg P1 0.5 ml solvent | vapor diffusion, 23° C., 7 days, removed solution | viscous sticky mass |
| acetic acid | water | 219 mg P1 0.3 ml solvent | vapor diffusion, 23° C., 7 days, removed solution | very similar to A (see FIG. 11B) |
| acetonitrile | water | 212 mg P1 0.4 ml solvent | vapor diffusion, 23° C., 6 days, removed solution | viscous sticky mass |

Evaporation Experiments

Solutions of the compound were dried at room temperature (dry nitrogen flow) without stirring. The results of the evaporation experiments of solid form A are presented in Table 5.

TABLE 5

| Starting form | Solvent | Concentration mg/ml | Conditions | Form produced |
|---|---|---|---|---|
| A | ethanol | 100/2.0 | 23° C. evaporated (dry N2) 2 days/23° C. | (solution) B" |
| A | ethyl acetate | 109/2.0 | 23° C. evaporated (dry $N_2$) 1 day/23° C. | (solution) very similar to A (see FIG. 12A) |
| A | THF | 183/2.0 | 23° C. evaporated (dry $N_2$) 5 days/23° C. | (solution) A + C (see FIG. 12B) |

Precipitation Experiments

Precipitation experiments were carried out with 42-79 mg of the compound. The non-solvent was added to the solution. The samples obtained after filtration (glass filter porosity P4) were air dried at ambient temperature and for a short time only to prevent possible desolvation of labile hydrates or solvates. The results of the precipitation experiments of solid form A are presented in Table 6.

TABLE 6

| Starting form | Solvent | Concentration mg/ml | Conditions | Form produced |
|---|---|---|---|---|
| A | ethanol | 79/0.2 79/1.2 | 23° C. added of 1.0 ml n-heptane stored 11 weeks/−20° C.; removed solution and dried solid residue ($N_2$ 43 ml/min) 50 min R.T. | (solution) (phase separation) very similar to A |
| A | ethyl acetate | 42/0.2 42/1.2 | 23° C. added of 1.0 ml n-heptane stirred 14 h/ 40° C. filtered & air dried | (solution) (viscous sticky mass) A |
| A | THF | 62/0.2 62/1.2 | 23° C. added of 1.0 ml n-heptane stirred 14 h/ 40° C. filtered & air dried | (solution) (viscous sticky mass) A |
| A | dichloro-methane | 75/0.3 75/1.2 | 23° C. added of 1.0 ml n-heptane stirred totally 13 h/ 40° C. filtered & air dried | (solution) (viscous sticky mass) A |

Recrystallization from Solution

The compound was dissolved in different solvent systems at room temperature and cooled to +5° C. or to −20° C. The samples obtained after filtration (glass filter porosity P4) were air dried at ambient temperature for a short time only to prevent possible desolvation of labile hydrates or solvates.

The results of the recrystallization experiments of solid form A are presented in Table 7.

TABLE 7

| Starting form | Solvent | Concentration mg/ml | Conditions | Form produced |
|---|---|---|---|---|
| A | ethanol + n-heptane 1:1 v/v | 72/0.4 | 23° C. stored 4 weeks/+5° C.; filtration, washed (n-heptane) and air-dried | (solution) A |
| A | ethyl acetate + n-heptane 1:1 v/v | 80/1.2 | 23° C. stored 4 weeks/−20° C.; filtered and air-dried | (solution) very similar to A (see FIG. 13A) |
| A | acetonitrile + toluene 1:1 v/v | 91/0.2 | 23° C. stored 4 weeks/−20° C.; removed solution and dried solid residue ($N_2$ 43 ml/min) 212 min R.T. | (solution) very similar to A |
| A | ethanol + n-heptane 1:3 v/v | 52/0.4 | 23° C. stored 1 day/+5° C.; filtered, washd (n-heptane) and air-dried | (solution) A |
| A | acetonitrile + toluene 1:3 v/v | 65/0.4 | 23° C. stored 4 weeks/−20° C.; filtered and air-dried | (solution) very similar to A (see FIG. 16B) |

Freeze Drying Experiment

The compound was dissolved in 1,4-dioxane and the solution was cooled to −50° C. During sublimation of the solvent the temperature of the solid was <0° C. as presented in Table 8:

TABLE 8

| Starting form | Solvent | Concentration mg/ml | Conditions | Form produced |
|---|---|---|---|---|
| A PP148-P1 | 1,4-dioxane | 102/2.0 | 23° C. freeze dried <0° C. stored 12 days/R.T. | (solution) viscous sticky mass very similar to A (see FIG. 14) |

Drying Experiment

The sample was dried overnight in a dry $N_2$-atmosphere at room temperature before closing the DSC sample pan. The results are summarized in Table 9:

TABLE 9

| Starting form | mg | Conditions | DSC |
|---|---|---|---|
| B' | 3.6 mg | dried overnight 23° C. (mass loss 1.0%) | FIG. 15 |

Cooling and Reheating of the Melt Experiments

After heating in DSC to 120° C. the samples were cooled to −50° C. and reheated to 120° C. The results are summarized in Table 10:

TABLE 10

Figure 7A:
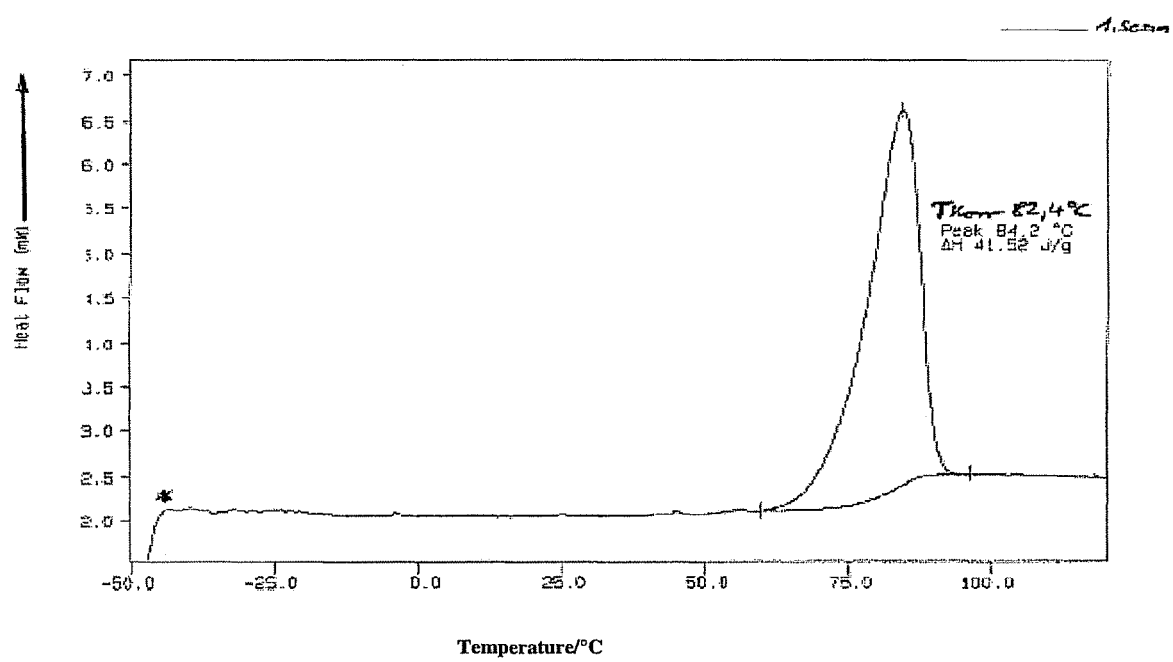
FIG. 7A-FIG. 7D are DSC spectra of sample batches P1-P4 of compound S-1, respectively. The asterisk indicates a settling effect, an artifact of the machinery used.
Figure 7B:
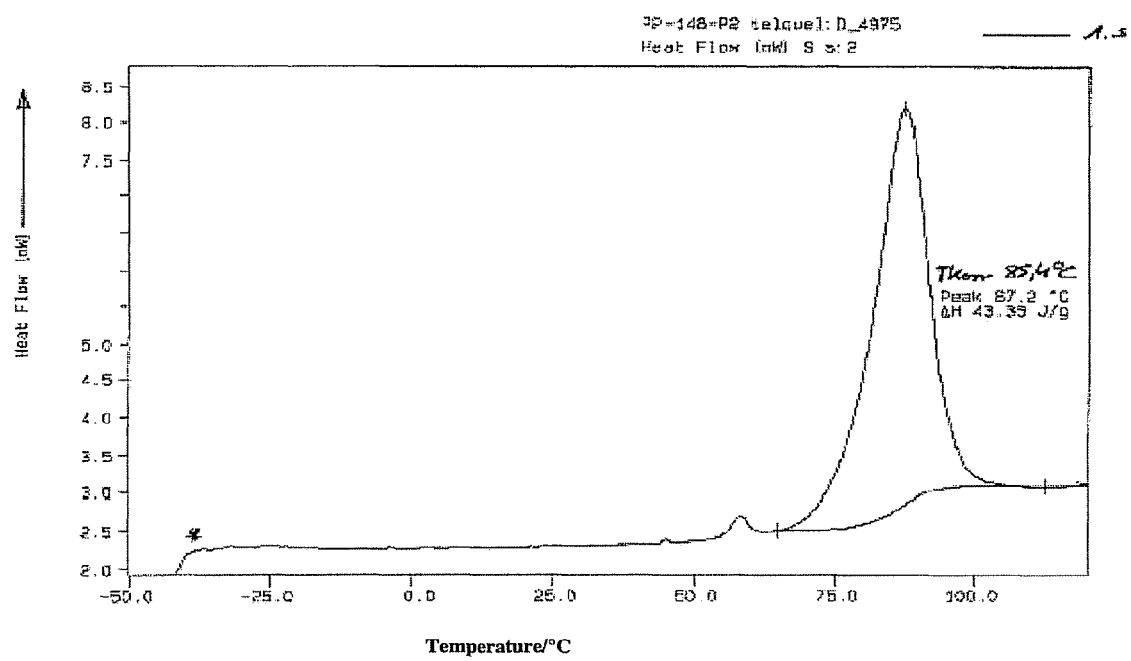
Figure 7C:
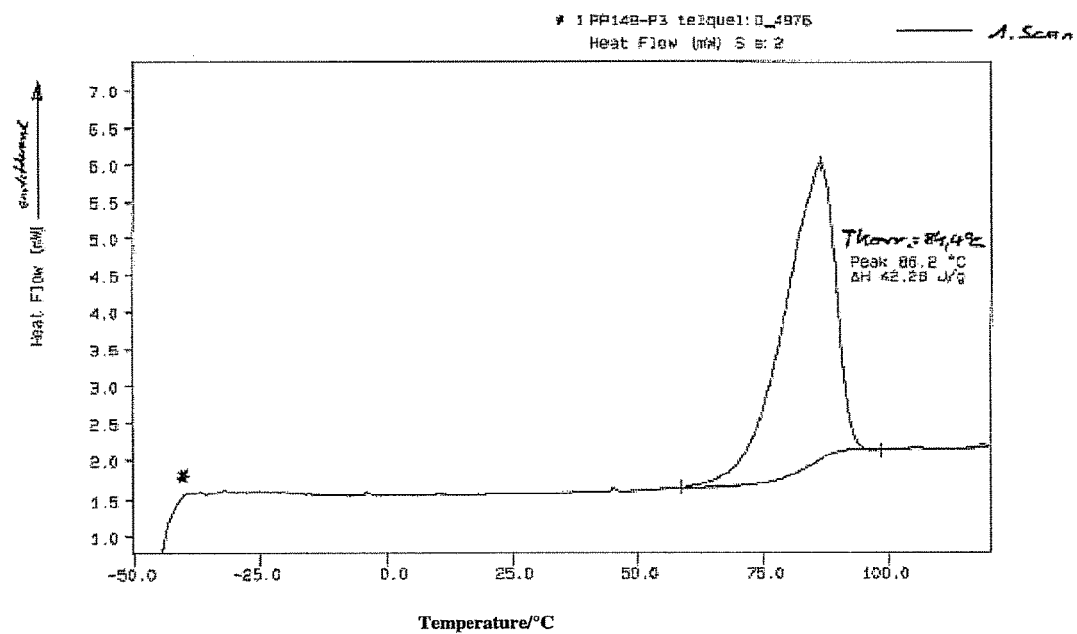
Figure 7D:
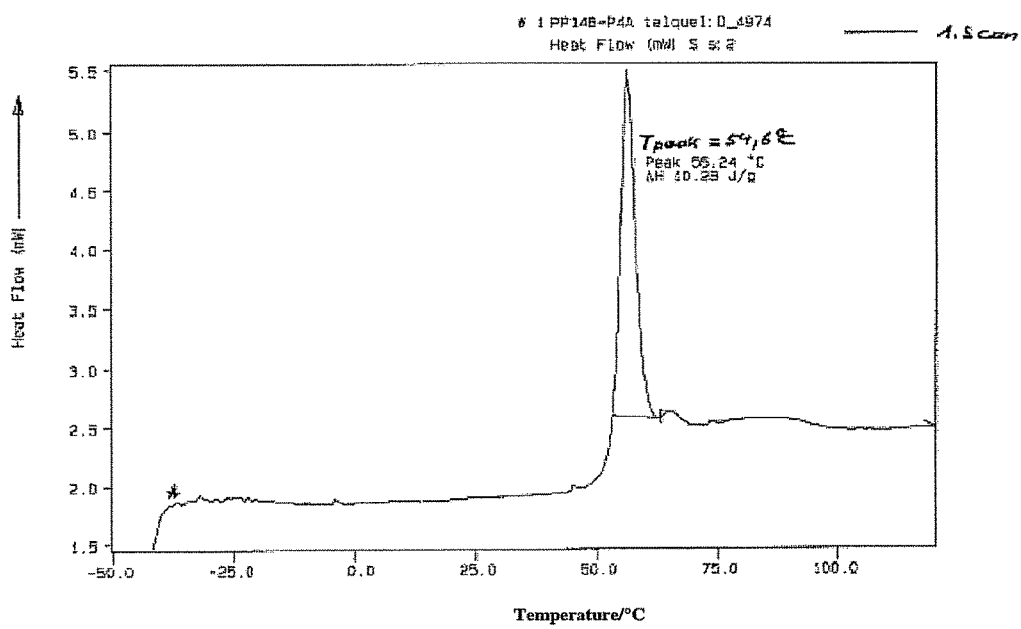
Figure 8A:
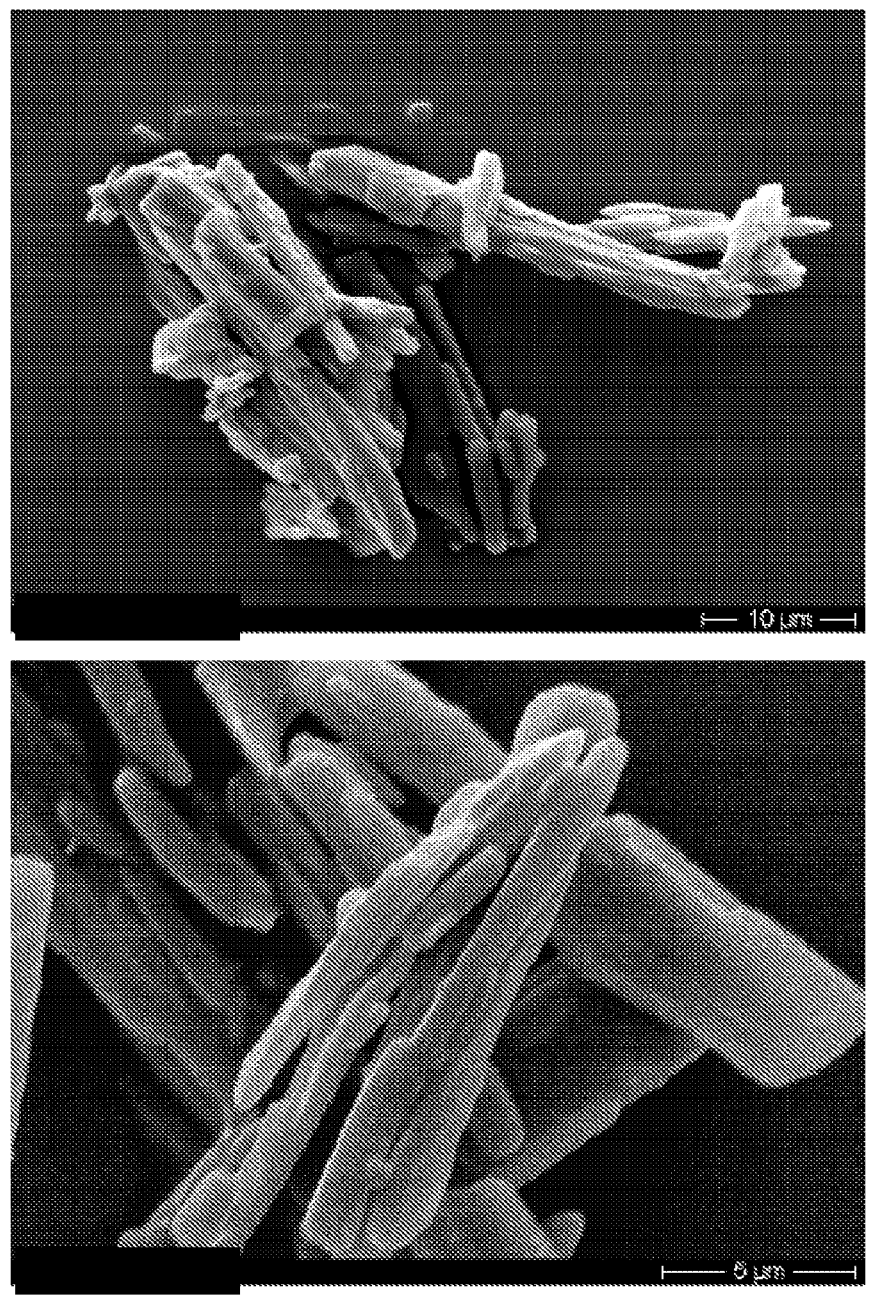
FIG. 8A-FIG. 8C are SEM micrographs of sample batches P1, P2 and P4 of compound S-1, respectively.
Figure 8B:
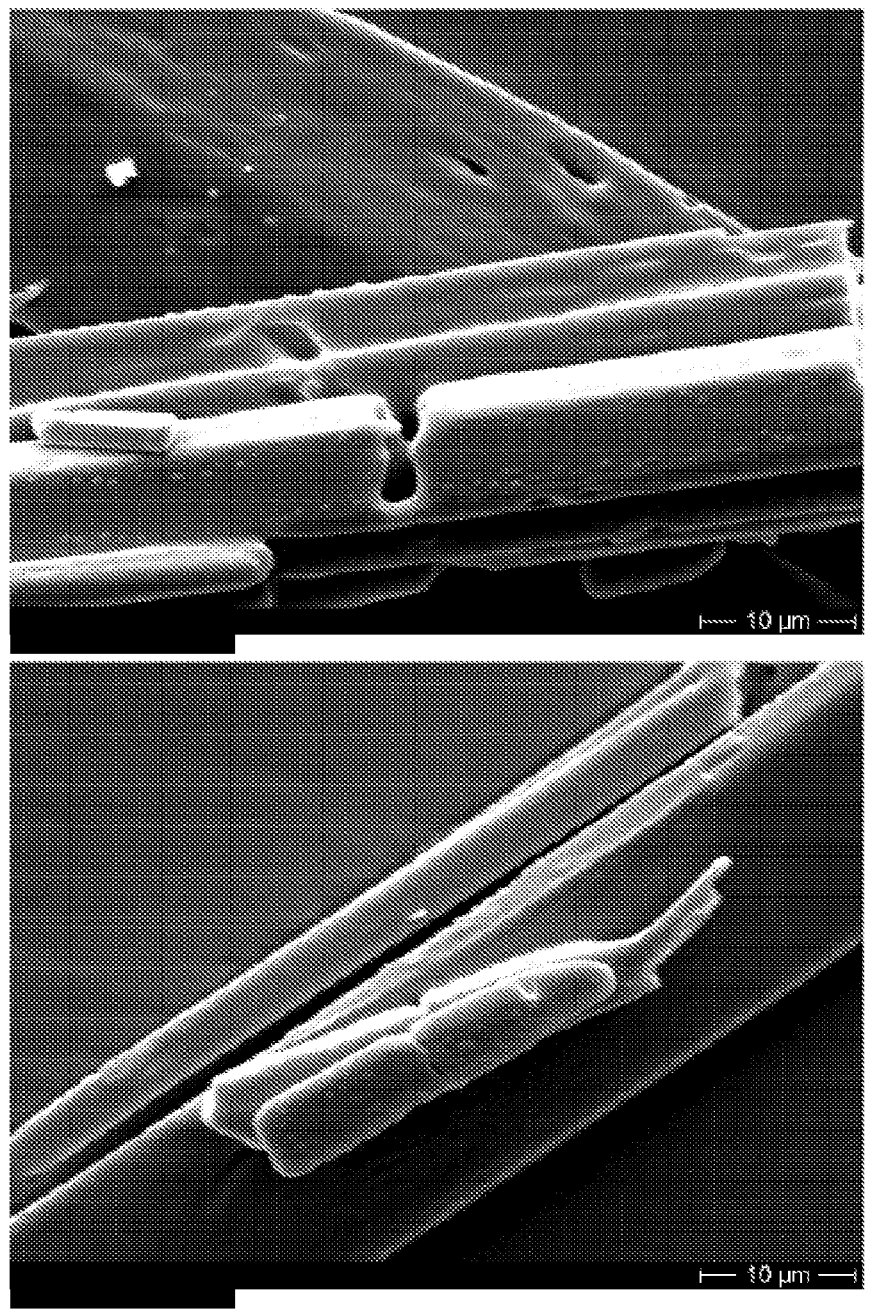
Figure 8C:
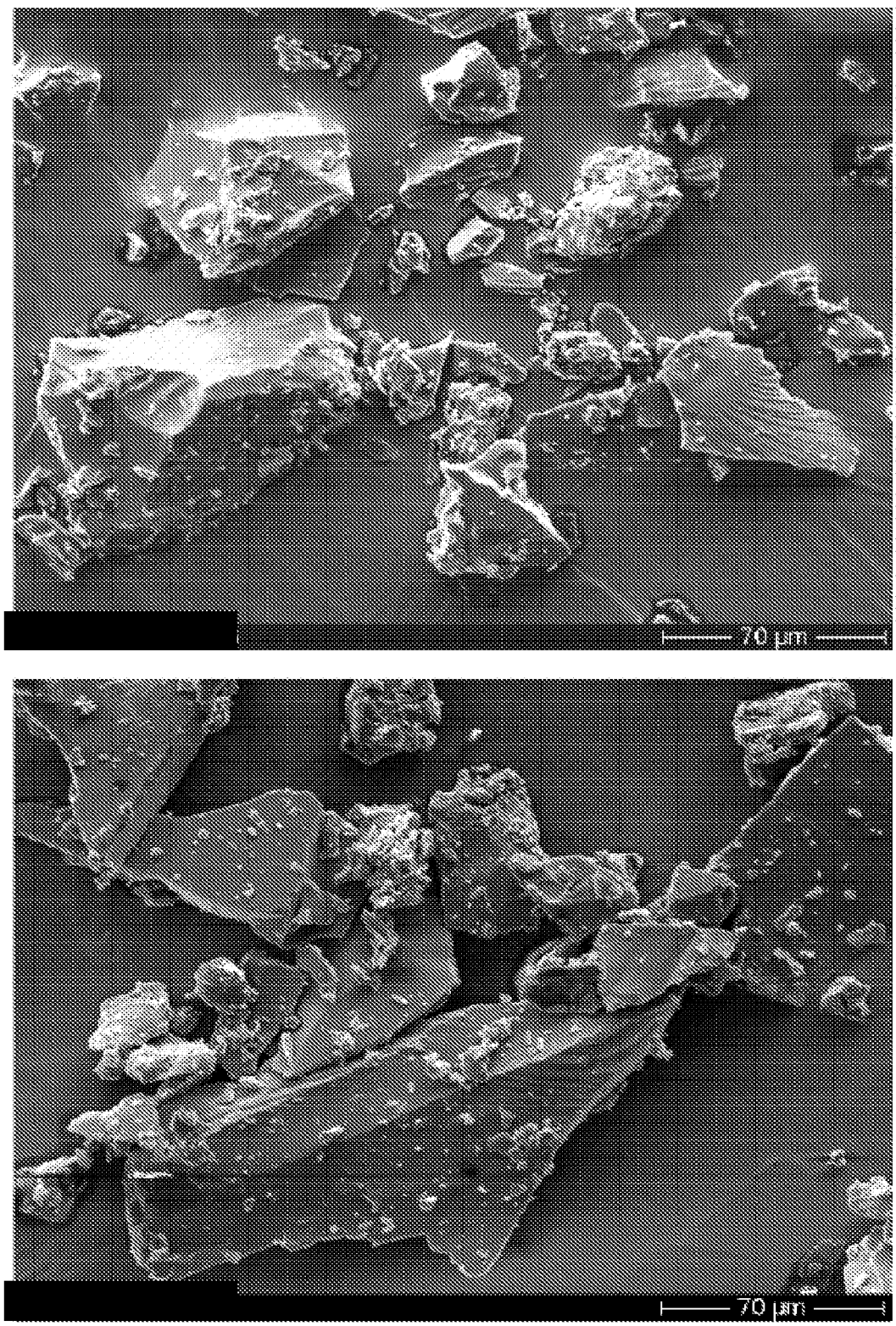
Figure 9A:
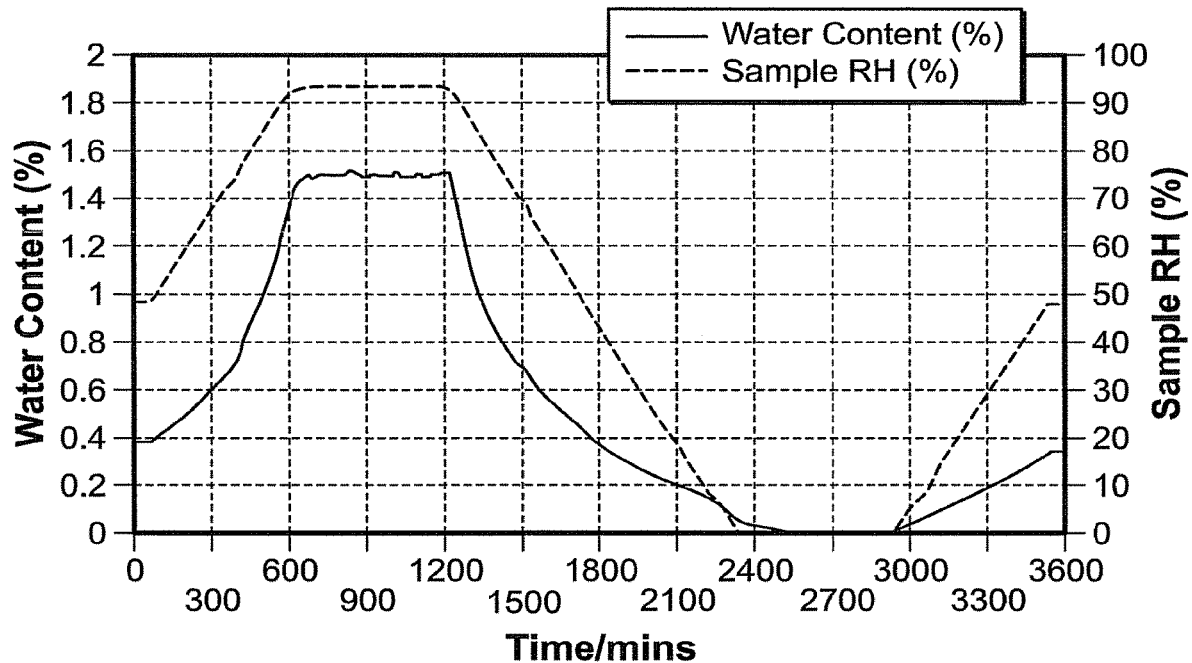
FIG. 9A-FIG. 9C are Dynamic Vapor Sorption (DVS) spectra of sample batches, P1, P2, and P4 of compound S-1, respectively.
Figure 9A:
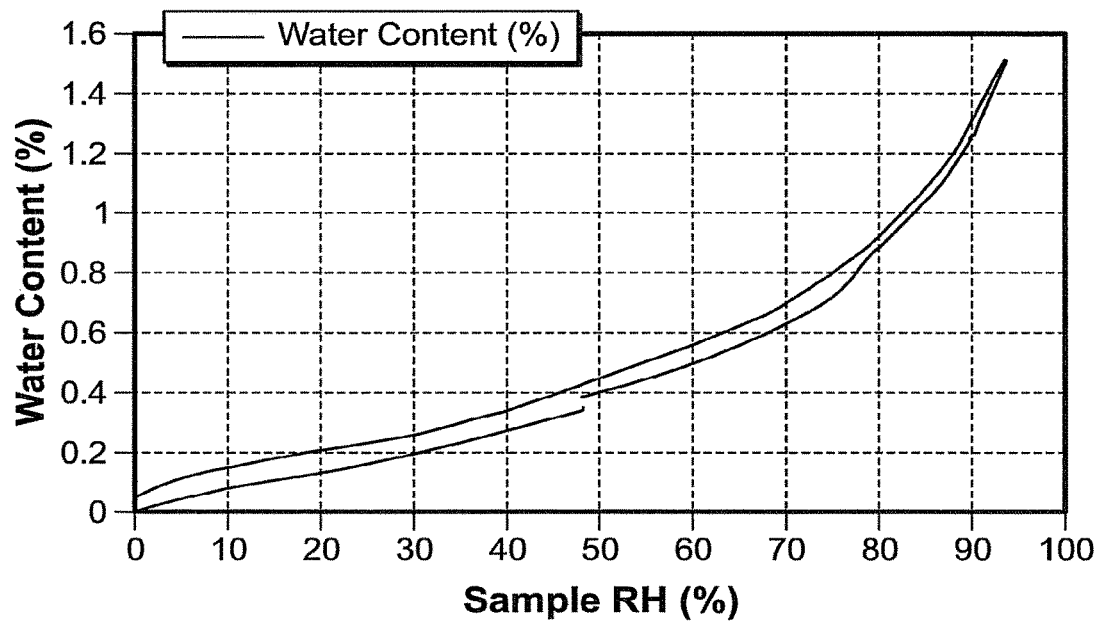
Figure 9B:
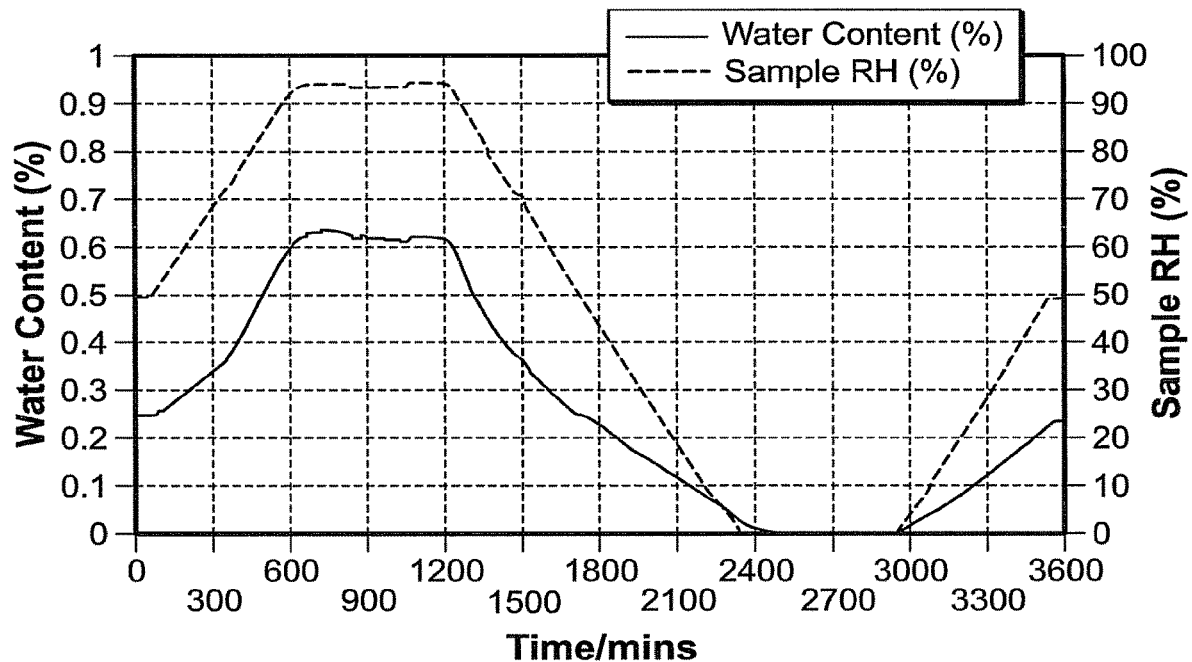
Figure 9B:
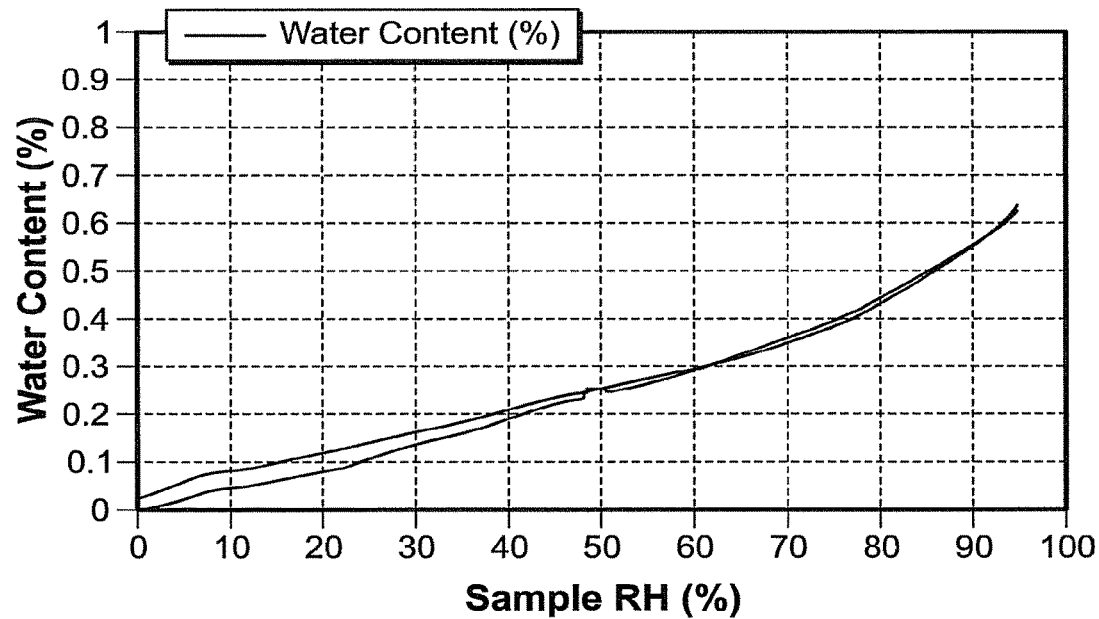
Figure 9C:
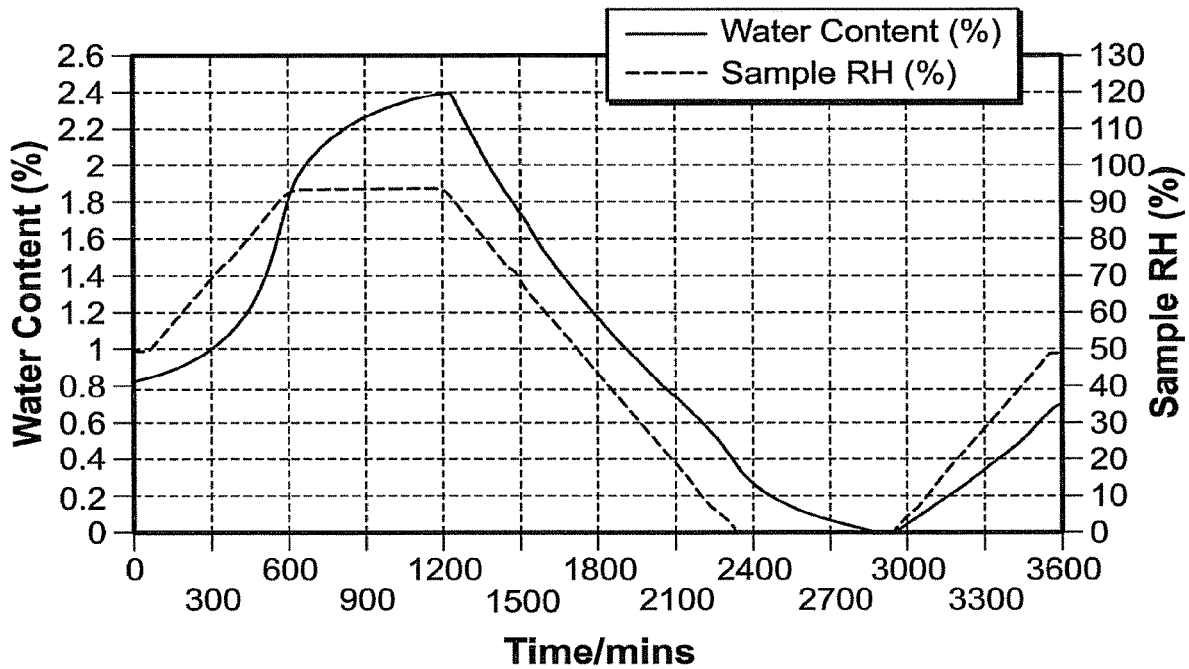
Figure 9C:
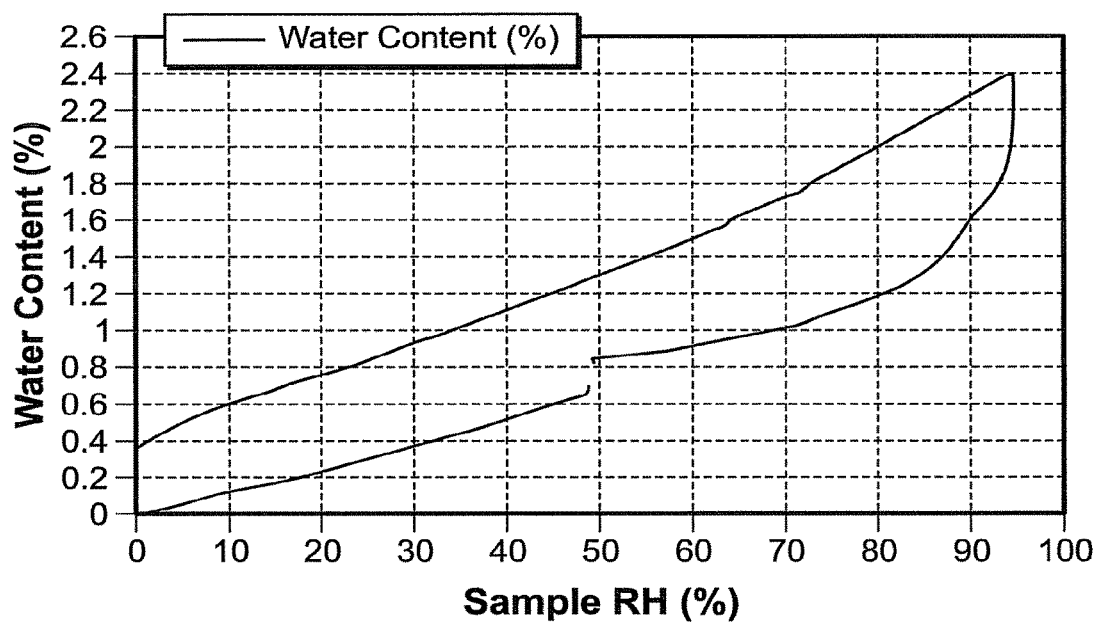
Figure 10A:
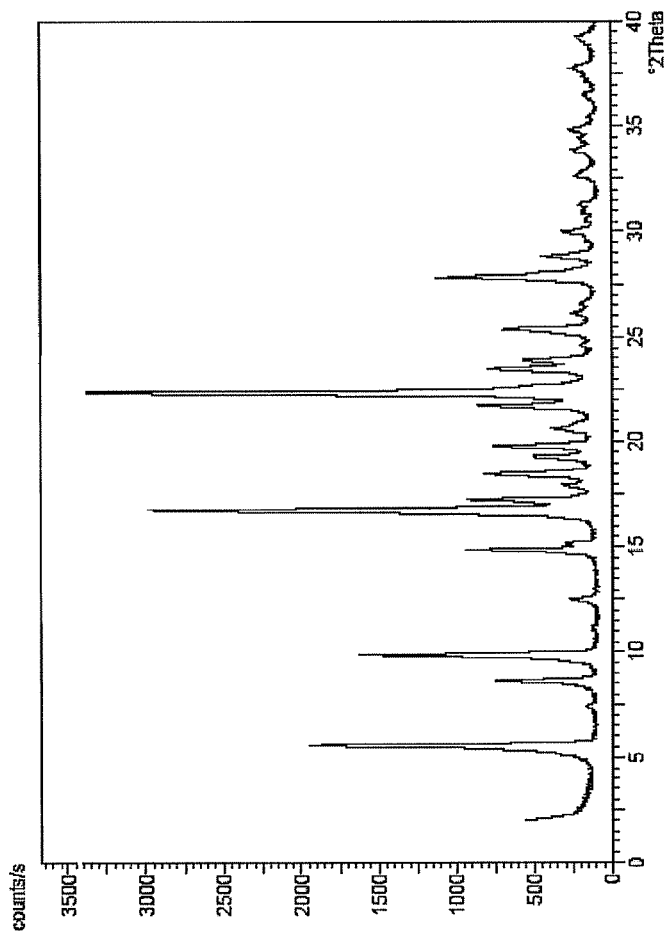
FIG. 10A-FIG. 10F demonstrates XRPD spectra of the compound obtained after varying the S-1 concentration in given solvents, varying the solvents, or a combination thereof.
Figure 10B:
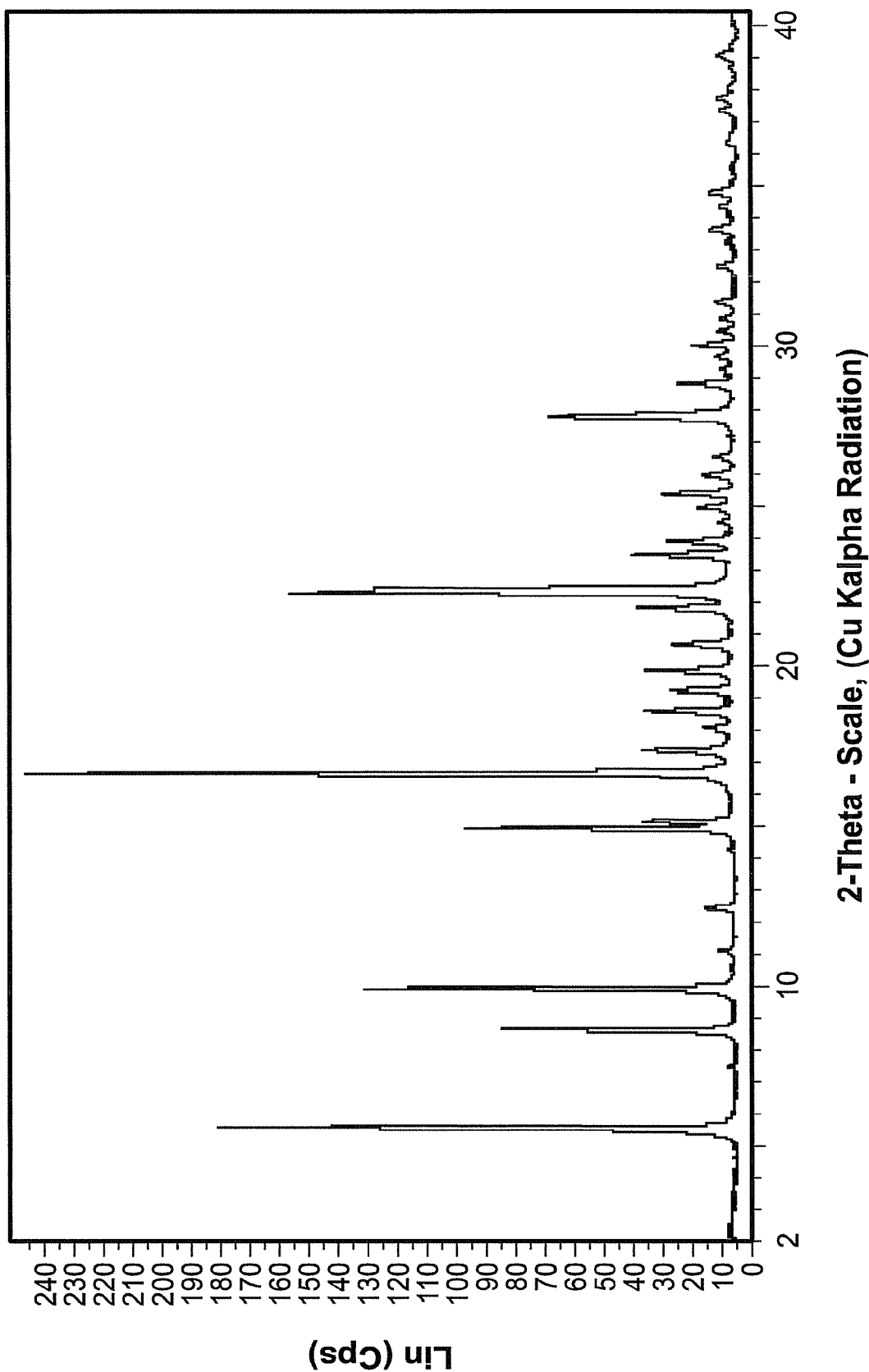
Figure 10C:
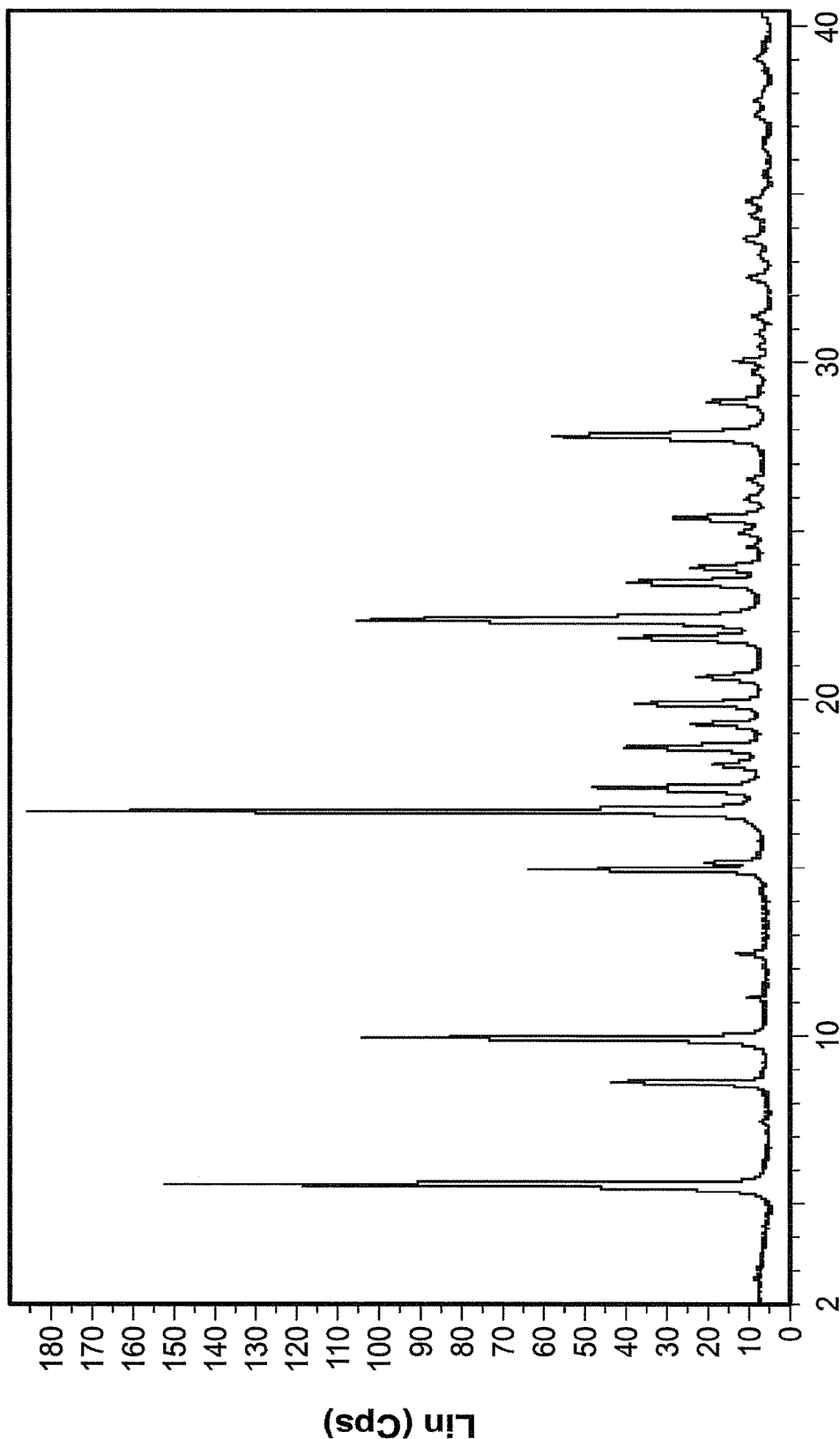
Figure 10D:
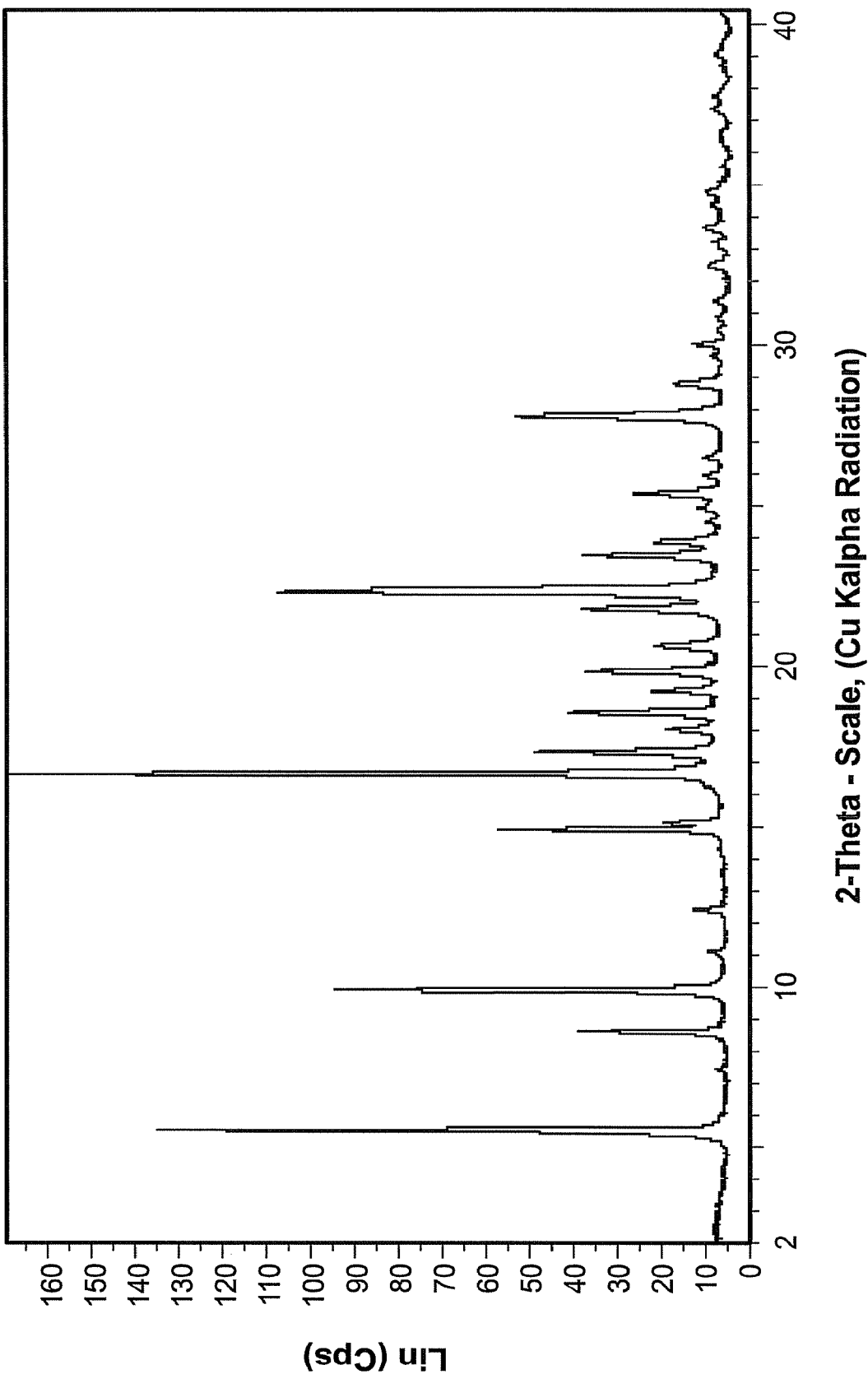
Figure 10E:
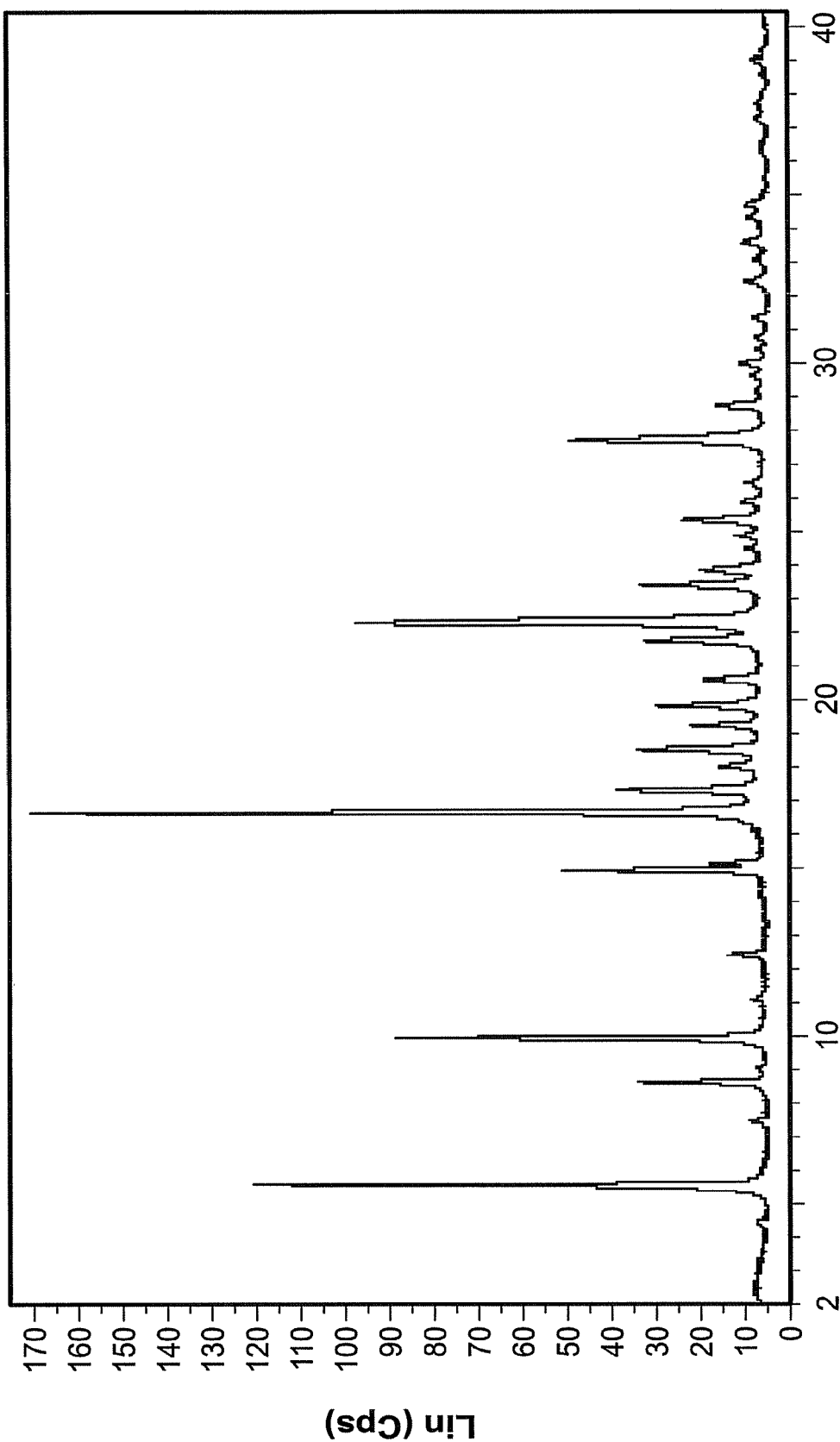
Figure 10F:
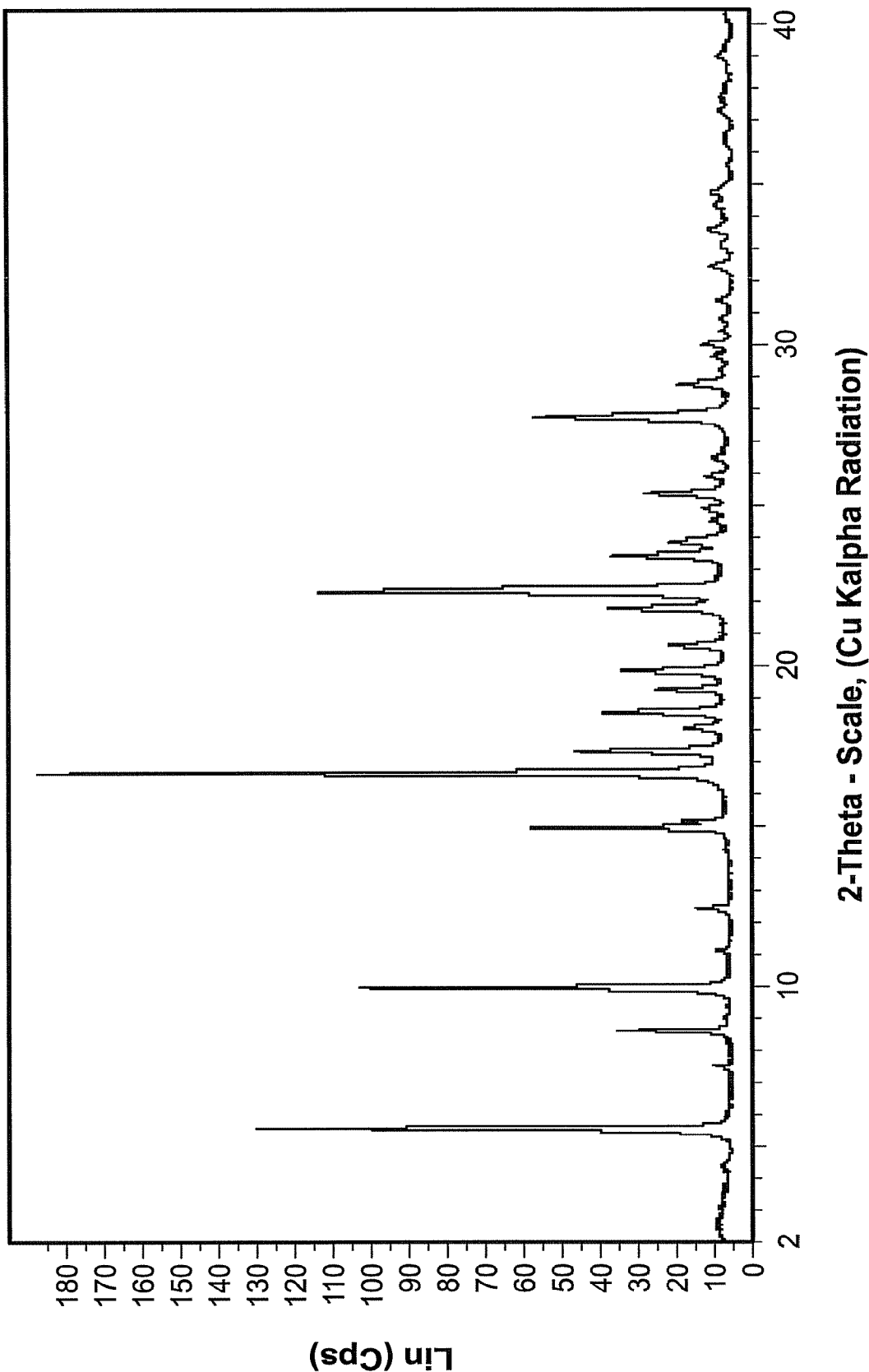
Figure 11A:
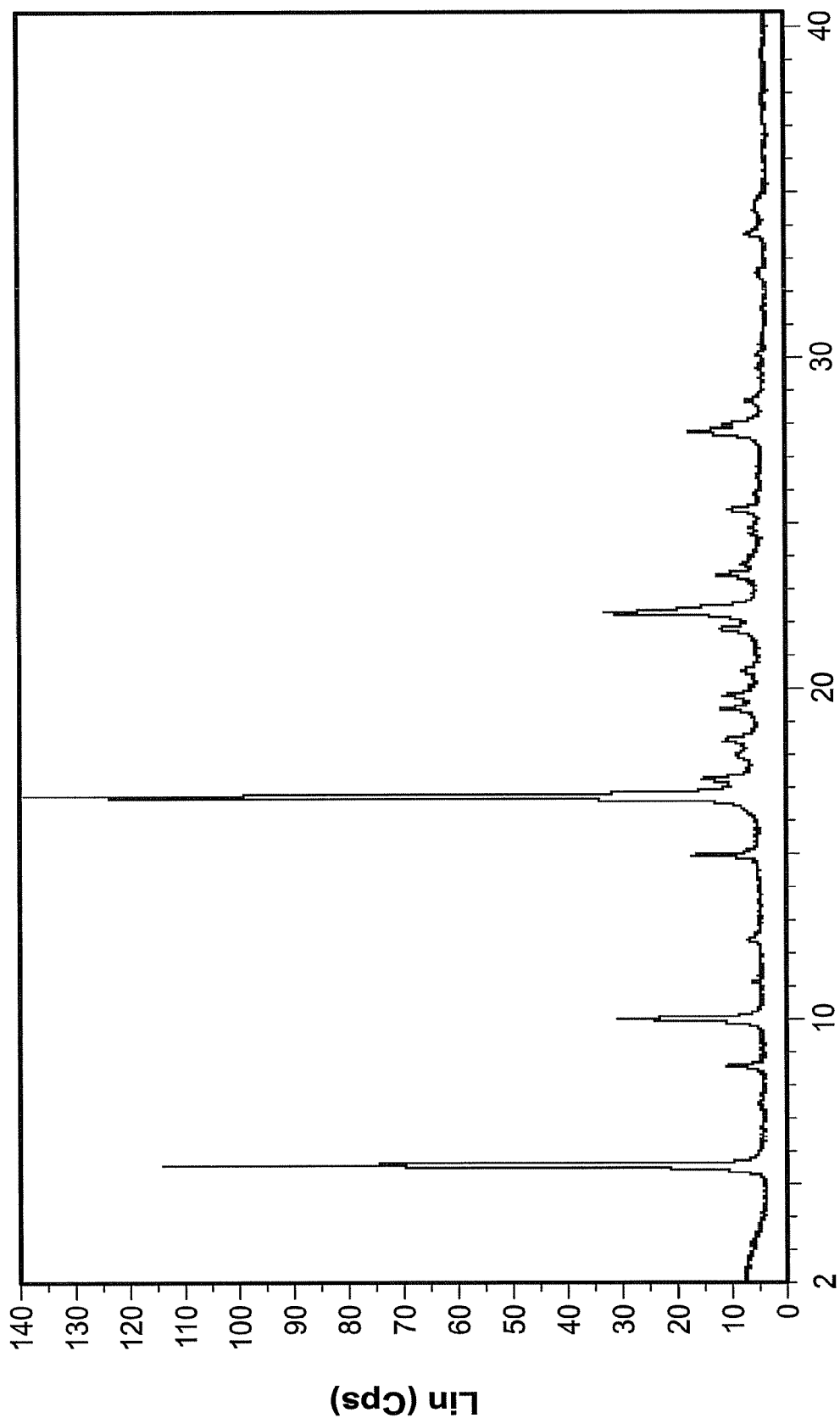
FIG. 11A-FIG. 11D shows the XRPD pattern representing the results of vapor diffusion experiments conducted with compound S-1.
Figure 11B:
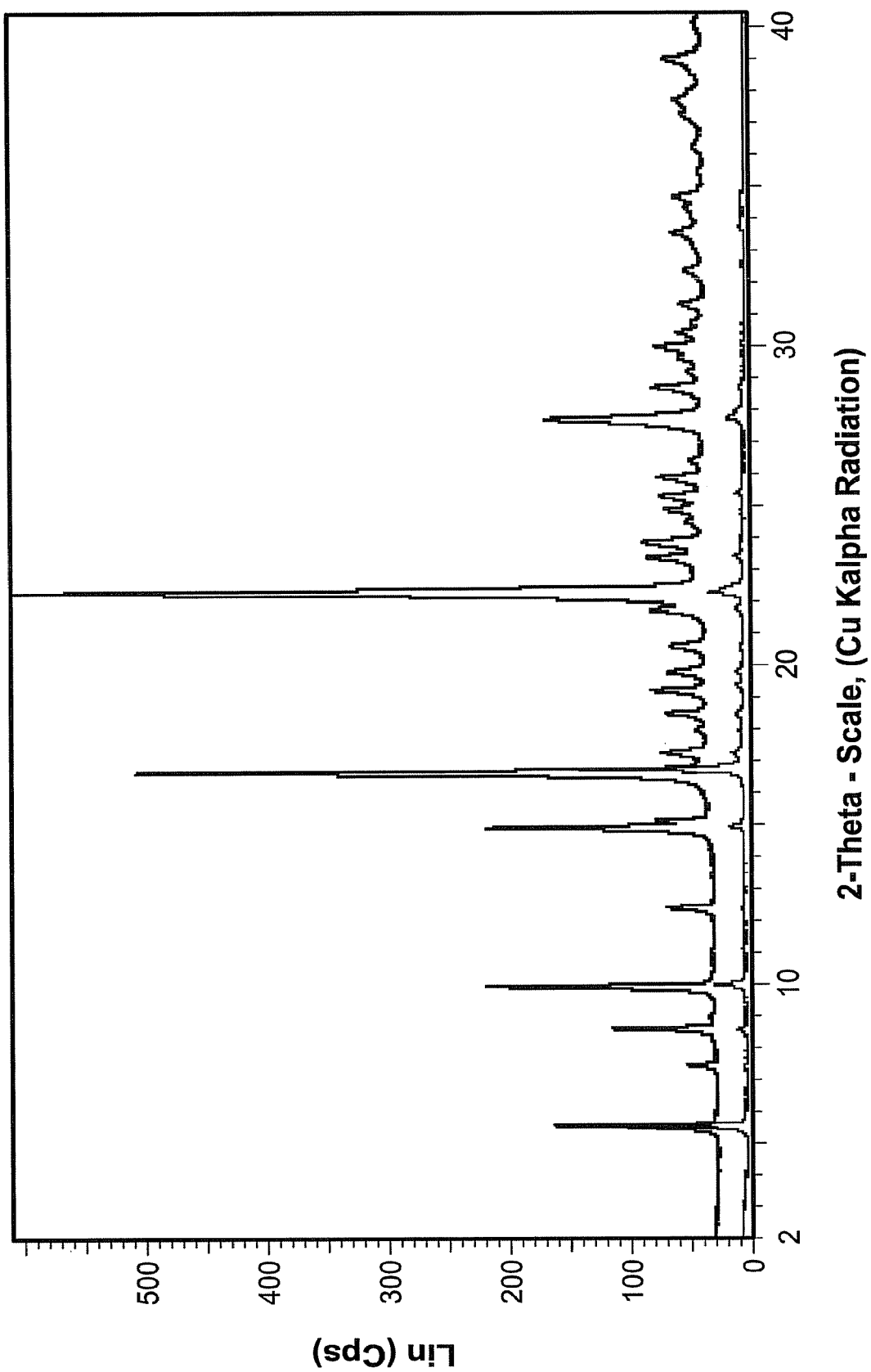
Figure 11C:
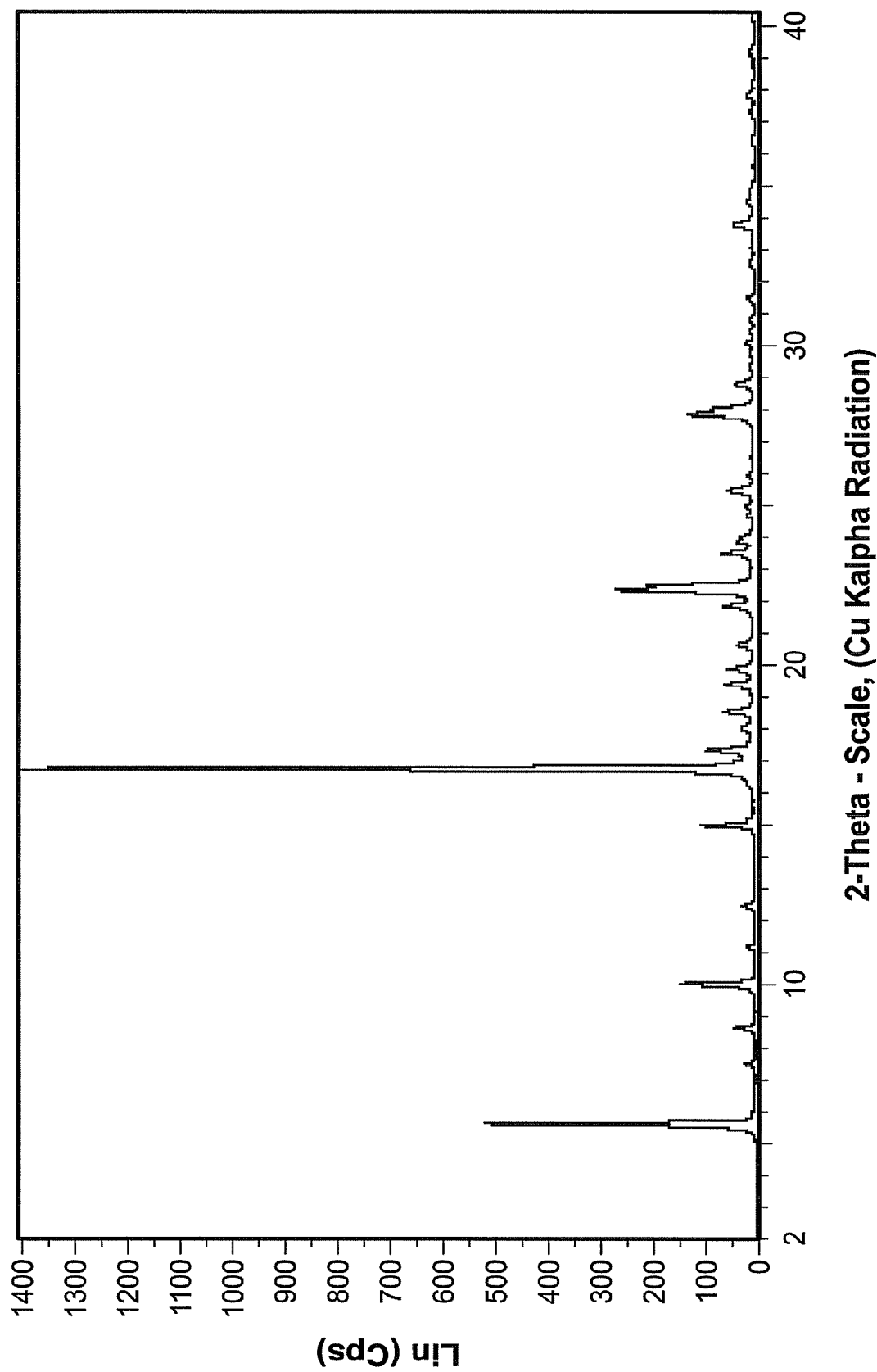
Figure 11D:
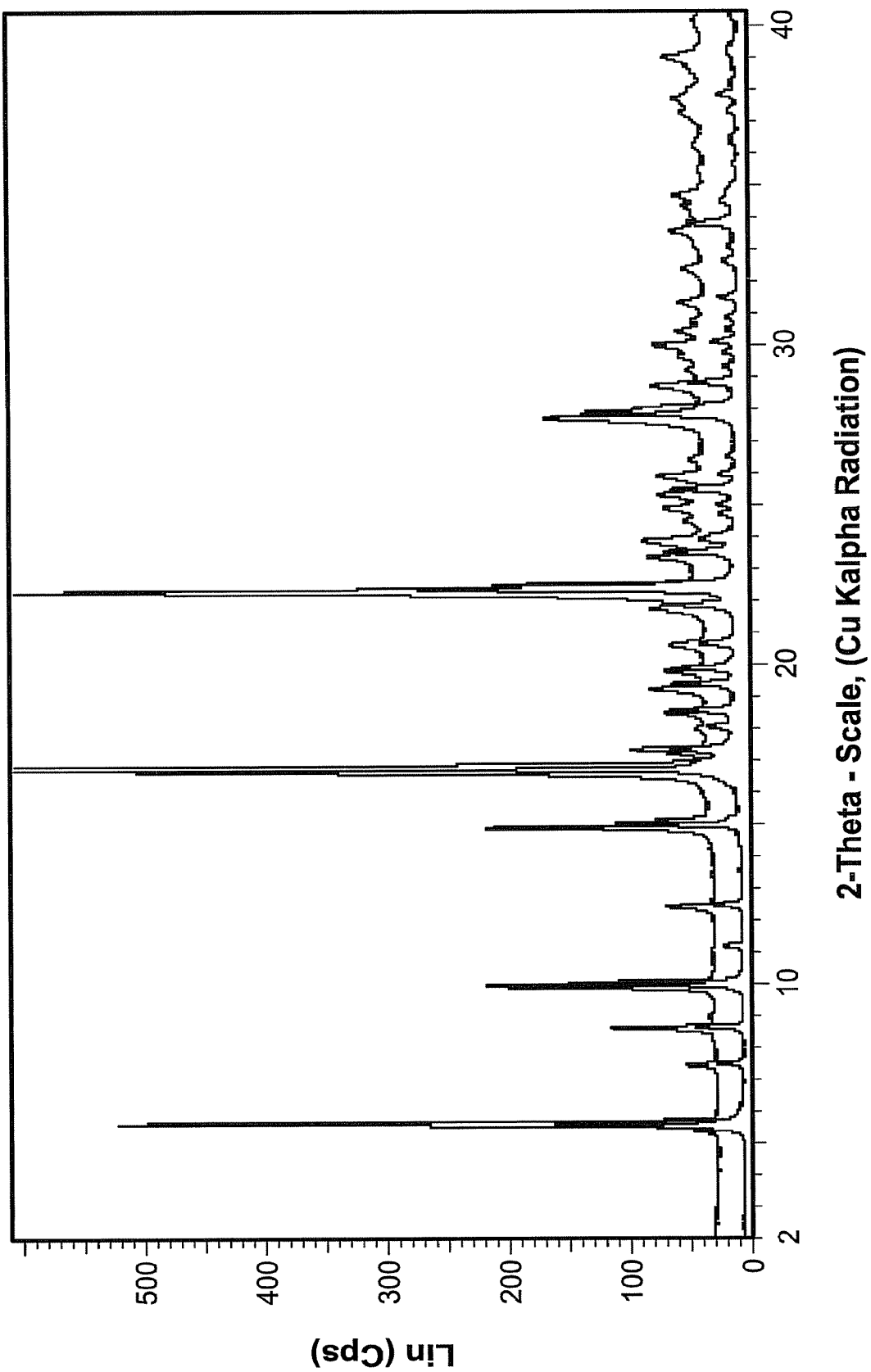

| Starting form | mg | Conditions | DSC |
|---|---|---|---|
| A | 3.4 mg | fast cooled to −50° C., heated: −50° C. to 120° C./20 K/min, fast cooled to −50° C. heated again: −50° C. to 120° C./20 K/min | FIG. 7A |
| A PP148-P2 | 4.4 mg | fast cooled to −50° C. heated: −50° C. to 120° C./20 K/min fast cooled to to −50° C. C. heated again: −50° C. to 120° C./20 K/min | FIG. 7B |
| A | 3.4 mg | fast cooled to −50° C. heated: −50° C. to 120° C./20 K/min fast cooled to −50° C. C. heated again: −50° C. to 120° C./20 K/min | FIG. 7C |
| B' | 2.9 mg | fast cooled to −50° C. heated: −50° C. to 120° C./20 K/min fast cooled to −50° C. heated again: −50° C. to 120° C./20 K/min | FIG. 7D |

Relative Stability Experiments

Suspension experiments were carried out with 130-145 mg of the compound. The suspensions were stirred with a magnetic stirrer and filtered after a predefined time. The samples obtained after filtration (glass filter porosity P4) were air dried at ambient temperature. The results are summarized in Table 11:

TABLE 11

| Starting forms | Solvent | Concentration mg/ml | Conditions | Form produced |
|---|---|---|---|---|
| A | ethyl acetate/n-heptane 1:2 (v/v) | approx. 130/2.0 | 23° C. stirred 3 days/23° C.; filtered and air-dried | (suspension) A (see FIG. 16A) |
| A | ethyl acetate/n-heptane 1:2 (v/v) | (81 + 64)/2.0 | 23° C. stirred 1 day/23° C.; filtered and air-dried | (suspension) A (see FIG. 16B) |

Water Solubility of Solid Forms A and B'

Suspensions of the solid forms (25 or 50 mg in 3.5 or 7.0 ml bidistilled water) were shaken (800 rpm) and filtered after 0.5 h, 1.5 h, 4 h and 20 h. After filtration the solid residue was checked by Raman spectroscopy and the concentration in the clear solution was determined by HPLC.

The solubility of solid form A of S-1 in water at 22° C. is summarized in Table 12:

TABLE 12

| Suspension equilibration time [h] | Solubility[a] [mg/1000 ml] | Solid residue [b] |
|---|---|---|
| 0.5 | 21.0 ± 3.9 | A + B' (approx. 95% + 5%) [c] |
| 1.5 | 24.0 ± 1.4 | A + B' (approx. 90% + 10%) [c] |
| 4.0 | 27.6 ± 1.5 | A + B' (approx. 85% + 15%) [c] |
| 20 | 24.5 ± 1.7 [d] | A + B' (approx. 75% + 25%) [c] |

[a] Mean value of two measurements (±standard deviation)
[b] Raman measurements
[c] Rough estimate
[d] pH of the solution: 8.7

The solubility of Form B' of S-1 in water at 22° C. is summarized in Table 13:

TABLE 13

| Suspension equilibration time [h] | Solubility[a] [mg/1000 ml] | Solid residue [b] |
|---|---|---|
| 0.5 | 27.4 ± 0.9 | B' |
| 1.5 | 27.3 ± 0.8 | B' |
| 4.0 | 25.6 ± 0.1 | B' |
| 20 | 26.7 ± 0.3 [c] | B' |

[a] Mean value of two measurements (±standard deviation)
[b] Raman measurements
[c] Rough estimate
d) pH of the solution: 8.7

Characterization of S-1-P1 Form A

The starting material for the polymorphism study, batch no. S-1-P1, is crystalline and the crystal form A. TG-FTIR shows that the mass loss up to 200° C. is very low (<0.2%) and therefore batch no. S-1-P1 is not a hydrate or solvate. Batch no. S-1-P1 melts at 82° C. (DSC peak temperature, heating rate 20 K/min). After melting and fast cooling to −50° C. in DSC the anhydrous liquid crystal form was produced. The sample showed a phase transition temperature of approx. 52° C. and did not recrystallize during heating in DSC. S-1-P1 might contain a small amount (roughly estimated 5%) of form B' or B".

The DVS measurement of form A at 25° C. does not show any evidence of classical hydrate formation under the experimental conditions used. The maximum water content at 93% relative humidity. is 1.5%. The very slight hysteresis is most probably caused by a viscous layer (possibly consisting of solid form B') on the surface of the particles, which influences the rate of water exchange. In fact, after storing form A at 96% relative humidity at room temperature for 11 weeks, Raman spectroscopy and DSC indicated the formation of approx. 20% of form B'.

Characterization of Solid Form B'

Investigations by DSC and XRPD indicate that the solid form produced during storage of solid form A at 40° C. and 75% relative humidity. (batch S-1-P4; 40° C./75% RH) is a paracrystalline form, having limited low-range order. This limited order most probably is responsible for the endothermal peak in DSC around 55° C. and the broad shoulder around 17° in the diffraction pattern. The solid form of batch S-1-P4 40° C./75% relative humidity is Form B'.

The DVS behavior of solid form B' at 25° C. is not the typical sorption behavior of a hydrate. The maximum water content at 94% relative humidity. is approx. 2.4%. Even though a certain hysteresis is observed, there is no clear step in the sorption curve which would clearly indicate the existence of a classical hydrate.

Formation of Solid Form B'

In addition to the observed transformation at high relative humidity, solid form B' can be produced by stirring a suspension of solid form A in water at 37° C. overnight.

Formation of Solid Form B"

Pathways to produce solid form B" are melting and cooling of the melt, and slow evaporation of solutions in solvents such as ethanol. Polymorph B" can be prepared from polymorphs A and D by heating them to above their respective melting points of 80° C. and 130° C. B' and B" are not distinguishable from any analytical methods used thus far but are distinguished based on their routes of formation. B' is assigned as a lyotropic liquid crystalline form due to its solvent mediated formation while B" is assigned as a thermotropic liquid crystalline form from its thermal method of preparation. Evaporation of the drug from solvents such as ethanol without an antisolvent also produces B".

Formation of Solid Form C

Polymorph C can only be obtained as a mixture with A by dissolving and subsequently evaporating the drug out of THF at ambient temperature.

Formation of Solid Form D

Polymorph D was originally produced by crystallization from a solvent/antisolvent mixture at 50° C. using ethyl acetate and cyclohexane as the solvent and antisolvents respectively. Form D can also be prepared from other polymorphic forms by "seeding" the sample with a small amount of D and storing it at 110° C./0% RH for 7 days or at 50° C. in water for 24 hours and drying.

Formation of Solid Form Toluene Solvate

The toluene solvate was prepared by any solvent/antisolvent crystallization method that used toluene as the antisolvent.

Water Solubility of Solid Forms A and B'

The solubility of forms A and B' of compound S-1 in water at 22° C. are 24.0±1.4 mg/1000 ml and 27.3±0.8 mg/1000 ml, values obtained after 1.5 h suspension equilibration time. These solubilities are very similar because of the fast transformation of form A into form B' on the surface of the particles during the solubility experiments.

Characterization of Different Batches of Solid Form A

Samples of batches S-1-P1, S-1-P2 and S-1-P3 show the same diffraction pattern. DSC measurements show that they most probably contain several % of solid form B' or B", indicated by heat capacity changes around 50° C. Sample S-1-P2 shows the highest level of solid form B' or B" (approx 20%). To better understand the DSC results, scanning electron micrographs (SEM) of samples S-1-P1 and S-1-P2 were produced. Whereas the pictures of sample S-1-P1 show quite well-formed particles, the pictures of sample S-1-P2 show a partial transformation, possibly caused by too high a drying temperature or partial contact with water. The partial formation of solid form B' or B" could also be caused by fast precipitation and a relatively high antisolvent/solvent ratio after precipitation. Other explanations would be drying at high temperatures or storage under high humidity conditions.

Solvent Systems for Crystallization of Solid Form A

Crystal form A is highly soluble in a number of solvents commonly used for crystallization. Due to its high solubility, solvent/antisolvent mixtures are necessary for crystallization.

Suspension equilibration experiments at room temperature revealed that solid form B' (batch S-1-P4; 40° C./75% RH) can be transformed into solid form A when stirring suspensions in ethylacetate/heptane 1:2 v/v or ethylacetate/pentane 1:2. In addition, suspension equilibration experiments using solid form A in ethyl formate/pentane 1:2 v/v and methyl acetate/pentane 1:2 v/v showed no transformation of solid form A. Therefore, these class 3 solvent/antisolvent mixtures can be used for crystallization of form A. The advantages of these solvent systems are the significantly lower boiling temperatures and therefore the possibly lower drying temperatures.

The details of the characterization of S-1-P1, solid Form A are given in Table 14:

TABLE 14

| | | |
|---|---|---|
| Compound | S-1 | |
| Batch no. | S-1-P1 | |
| XRPD | solid form A | Figures XRPD-1a and XRPD-1b (see FIG. 4A) |
| Raman | solid form A sample might contain a small amount of B' or B" | Figure Raman-1 (see FIG. 5A) |
| TG-FTIR | mass loss 25° C. to 245° C.: <0.2% | Figure TG-FTIR-1 (see FIG. 6A) |
| DSC | melting temperature: 82.4° C. (peak temperature, hermetically sealed gold sample pan, heating rate 20 K/min) ΔH: −42 J/g sample might contain a small amount (roughly estimated 5%) of form B' or B" | Figures DSC-1a and DSC-1b (See FIG. 7A) |
| SEM | quite well-formed particles | Figures SEM-1 (see FIG. 8A |
| DVS | water content at 50% r.h.: 0.4% maximum water content at 93% r.h.: 1.5% | Figures DVS-1a and DVS-1b (FIG. 9A |

The details of the characterization of S-1-P2, solid Form A, are given in Table 15:

TABLE 15

| | | |
|---|---|---|
| Compound | S-1 | |
| Batch no. | S-1-P2 | |
| XRPD | solid form A | Figures XRPD-2a and XRPD-2b (see FIG. 4B) |
| Raman | solid form A + B' or B" | Figure Raman-2 (See FIG. 5B) |
| TG-FTIR | mass loss 25° C. to 245° C.: <0.2% | Figure TG-FTIR-2 (see FIG. 6B) |
| DSC | melting temperature: 85.4° C. (peak temperature, hermetically sealed gold sample pan, heating rate 20 K/min) ΔH: −43 J/g sample contains approx. 20% of form B' or B" | Figures DSC-2a and DSC-2b (see FIG. 7B) |
| SEM | pictures show partial transformation | Figures SEM-2 (see FIG. 8B) |
| DVS | water content at 50% r.h.: 0.3% maximum water content at 95% r.h.: 0.6% | Figures DVS-2a and DVS-2b (see FIG. 9B) |

The details of the characterization of S-1-P3, solid Form A, are given in Table 16:

TABLE 16

| | | |
|---|---|---|
| Compound | S-1 | |
| Batch no. | S-1-P3 | |
| XRPD | solid form A | Figures XRPD-3a and XRPD-3b (see FIG. 4C) |

TABLE 16-continued

Figure 6A:
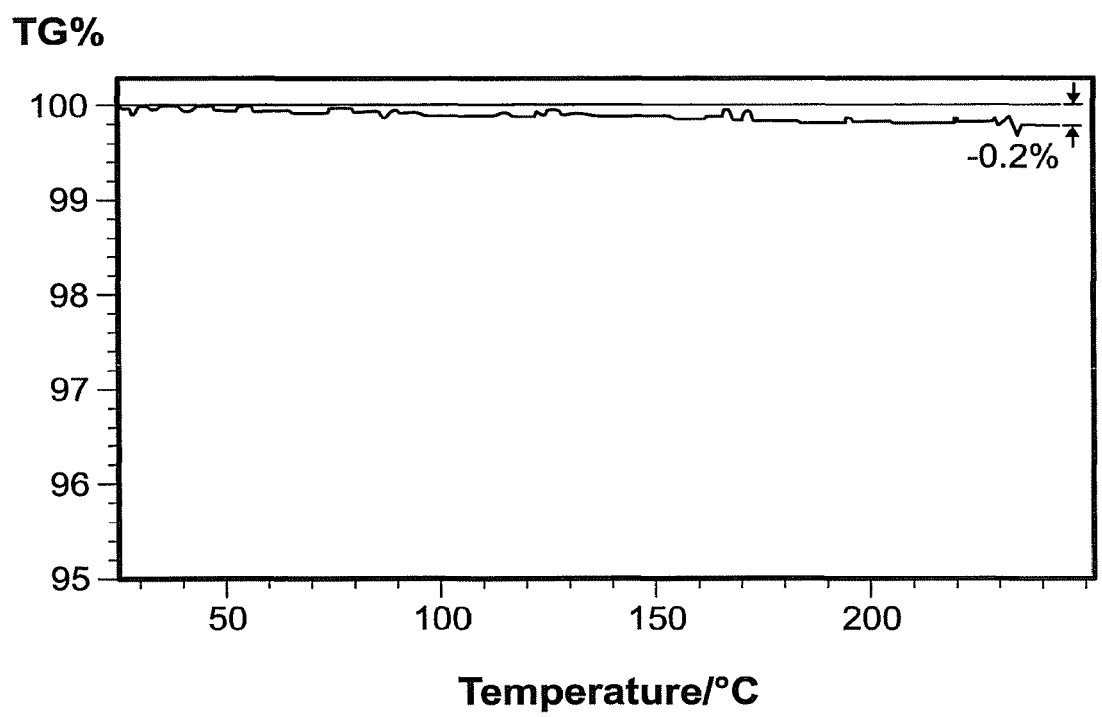
FIG. 6A-FIG. 6D are TG-FTIR spectra of sample batches P1-P4 of compound S-1, respectively. Conditions included a temperature range operation in the dynamic mode of 25° C./10.0/250° C., in an N$_2$ atmosphere.
Figure 6B:
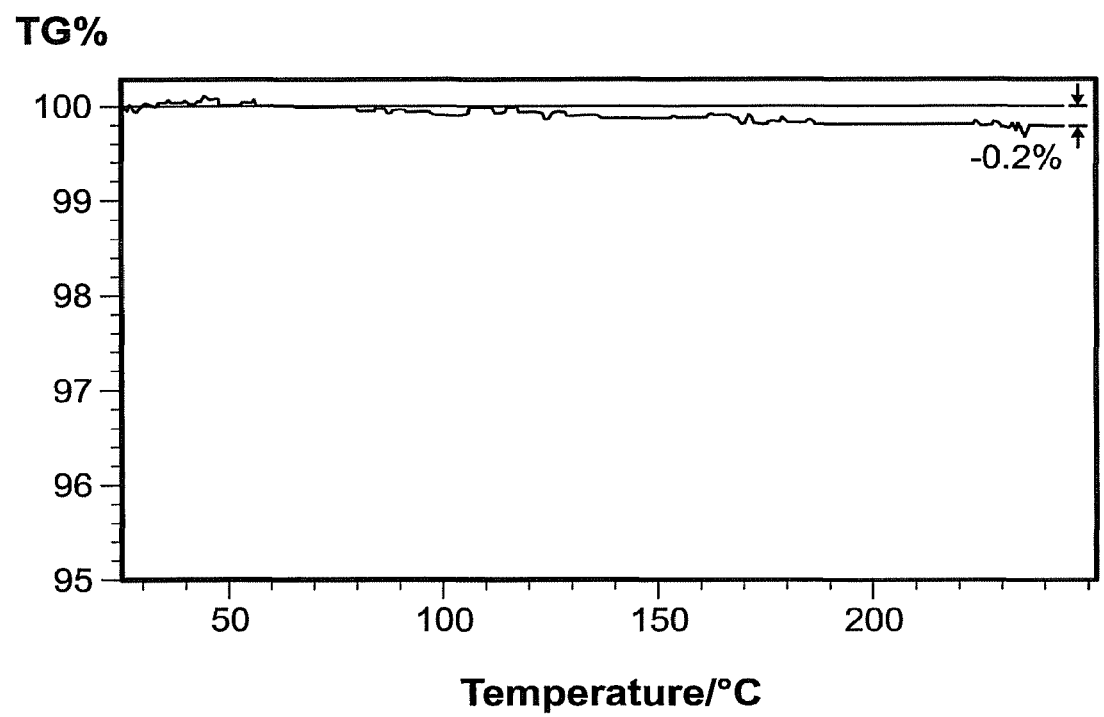
Figure 6C:
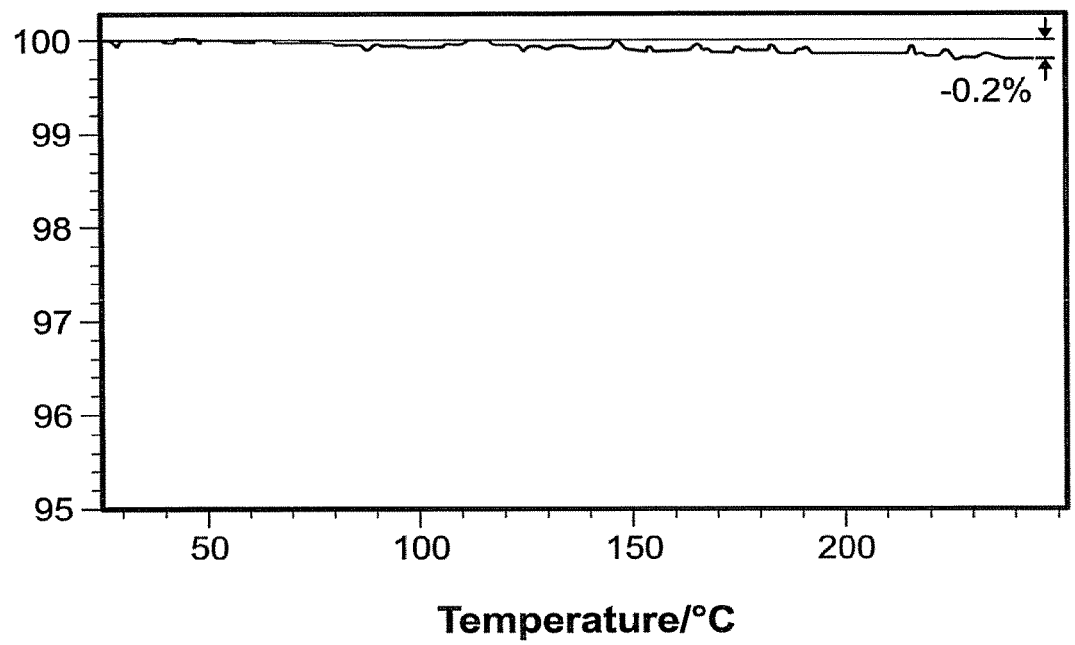
Figure 6D:
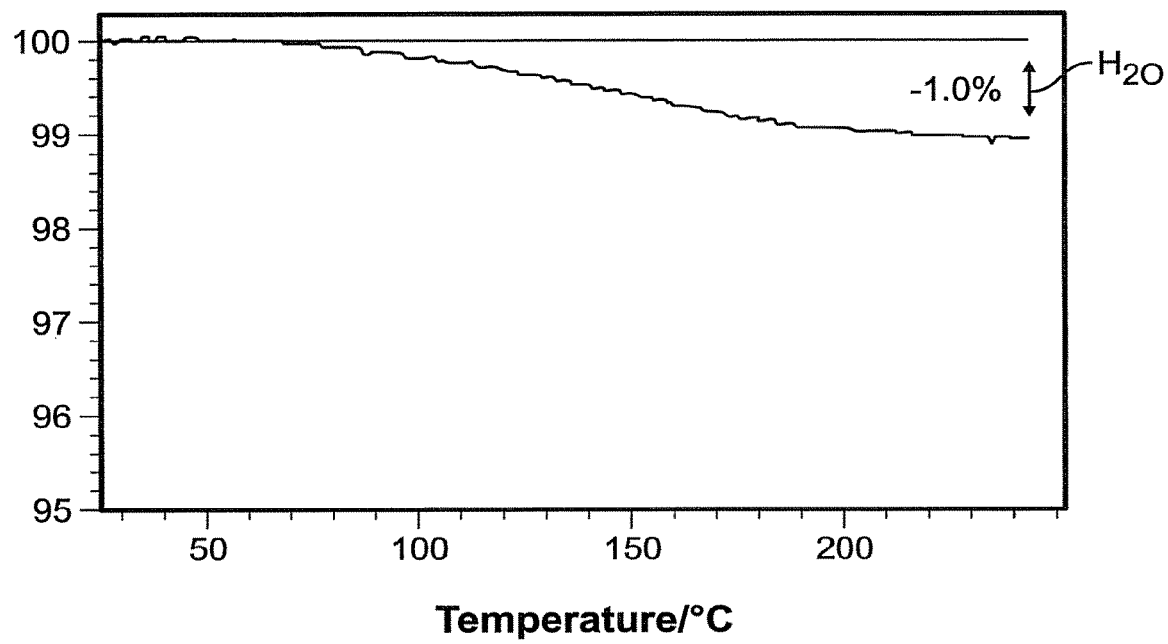

| | | |
|---|---|---|
| Raman | solid form A sample might contain a small amount of B' or B" | Figure Raman-3 (see FIG. 5C) |
| TG-FTIR | mass loss 25° C. to 245° C.: <0.2% | Figure TG-FTIR-3 (see FIG. 6C |
| DSC | melting temperature: 84.4° C. (peak temperature, hermetically sealed gold sample pan, heating rate 20 K/min) ΔH: −42 J/g sample might contain a small amount (roughly estimated 5%) of form B' or B" | Figures DSC-3a and DSC-3b (see FIG. 7C |
| SEM | not analyzed | — |
| DVS | not analyzed | — |

The details of the characterization of S-1-P4, solid Form B' are given in Table 17:

TABLE 17

| | | |
|---|---|---|
| Compound | S-1 | |
| Batch no. | S-1-P4 40° C./75% RH | |
| XRPD | solid form B' sample might contain a small amount of form A | Figures XRPD-4a and XRPD-4b (see FIG. 4D) |
| Raman | solid form B' | Figure Raman-4 (see FIG. 5D) |
| TG-FTIR | mass loss 25° C. to 245° C.: 1.0% (water) | Figure TG-FTIR-4 (see FIG. 6D) |
| DSC | endothermal peak: ~55° C. (peak temperature, hermetically sealed gold sample pan, heating rate 20 K/min) ΔH: ~10 J/g | Figures DSC-4a and DSC-4b (see FIG. 7D) |
| SEM | significant change in morphology | Figures SEM-3 (see FIG. 8C) |
| DVS | water content at 50% r.h.: ~0.8% maximum water content at 94% r.h.: ~2.4% | Figures DVS-3a and DVS-3b (see FIG. 9C) |

The different batches P1, P2 and P3 of compound S-1 revealed crystalline Form A with similar characteristic behavior of XRPD, Raman, TG FTIR, DVS and DSC results. Batch P4 revealed a paracrystalline solid form as characterized by its broad XRPD, Raman, TG FTIR, DVS and DSC results as described hereinabove.

Relative Stability of Polymorphic Forms Under Dry Conditions

The DSC thermogram of A and D in FIG. 19 show that A melts near 80° C. while D has a melting point near 130° C. The enthalpy of melting for A is 40±5 J/g while the enthalpy of melting is 75±5 J/g. The melting temperature and enthalpy suggest that D possesses greater stability in comparison to form A.

Figure 4D:
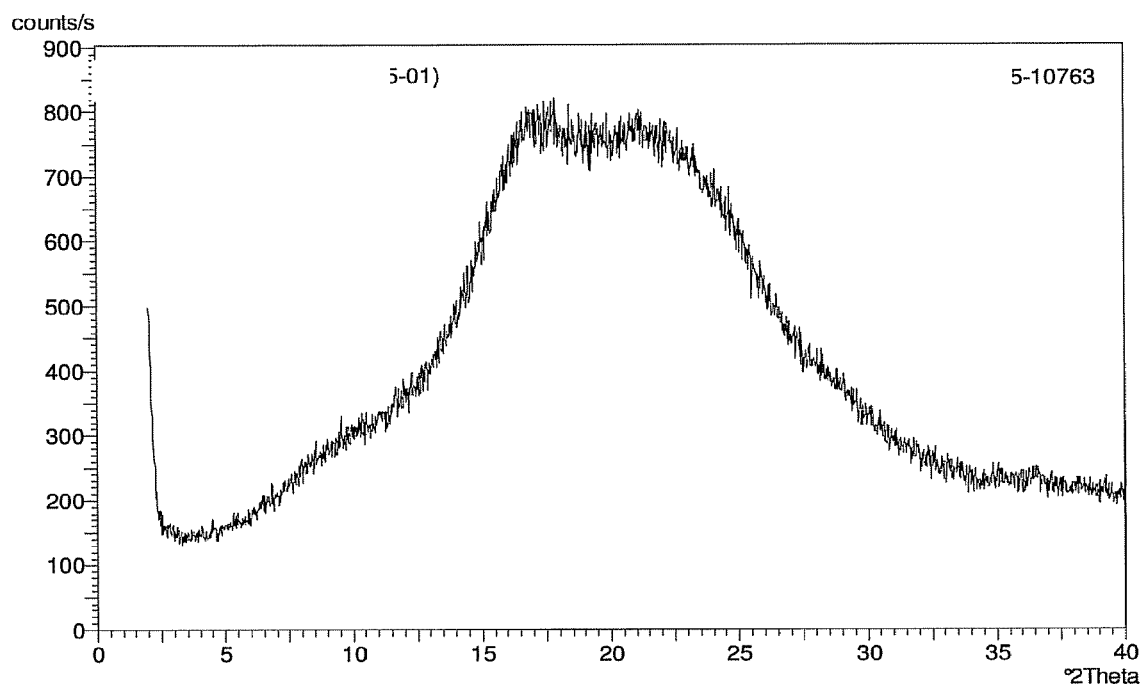
Figure 5A:
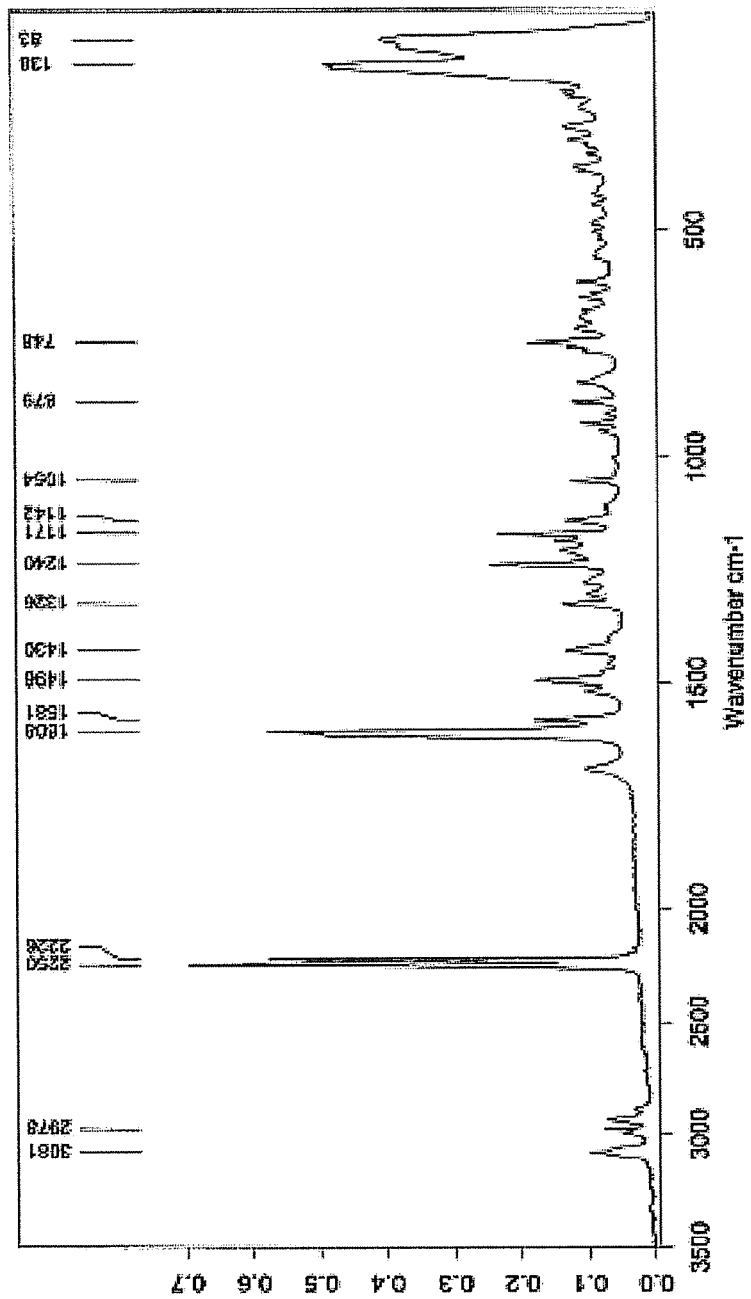
FIG. 5A-FIG. 5D are Raman spectra of sample batches P1-P4 of compound S-1, respectively. The laser power setting was 100 mW, at a resolution of 2 cm$^{-1}$.
Figure 5B:
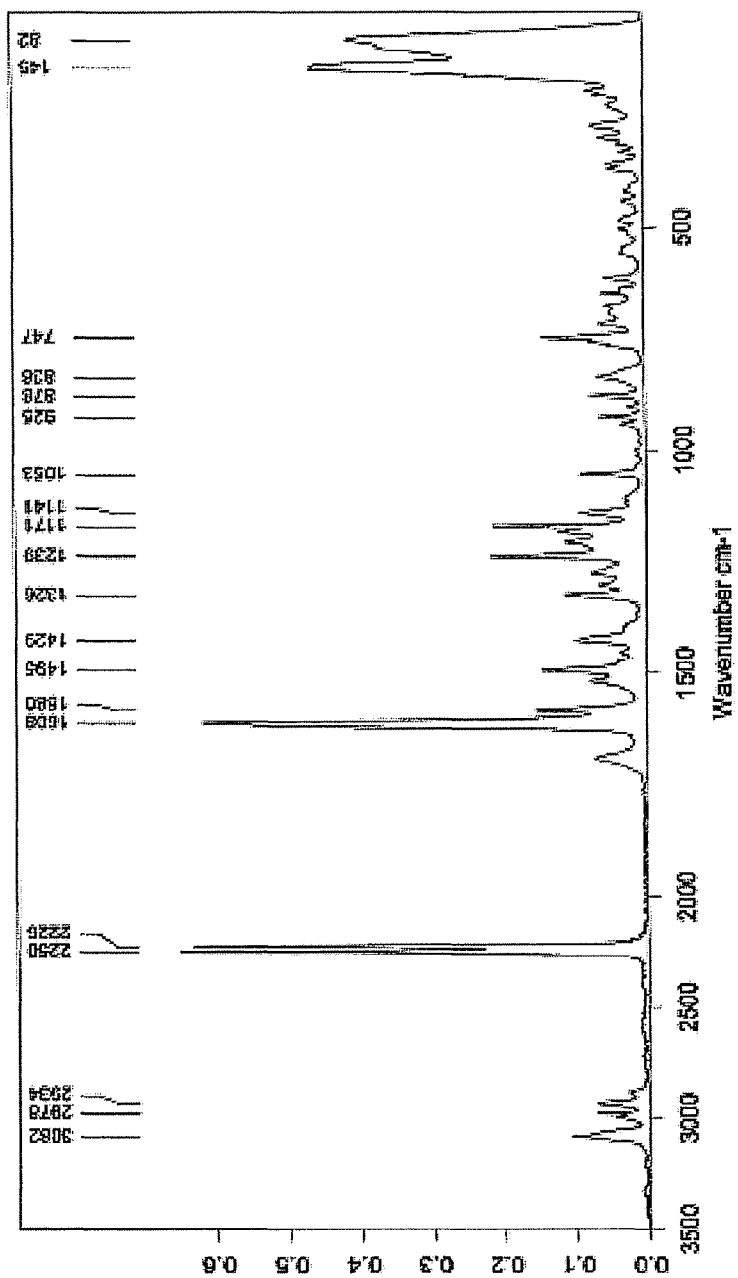
Figure 5C:
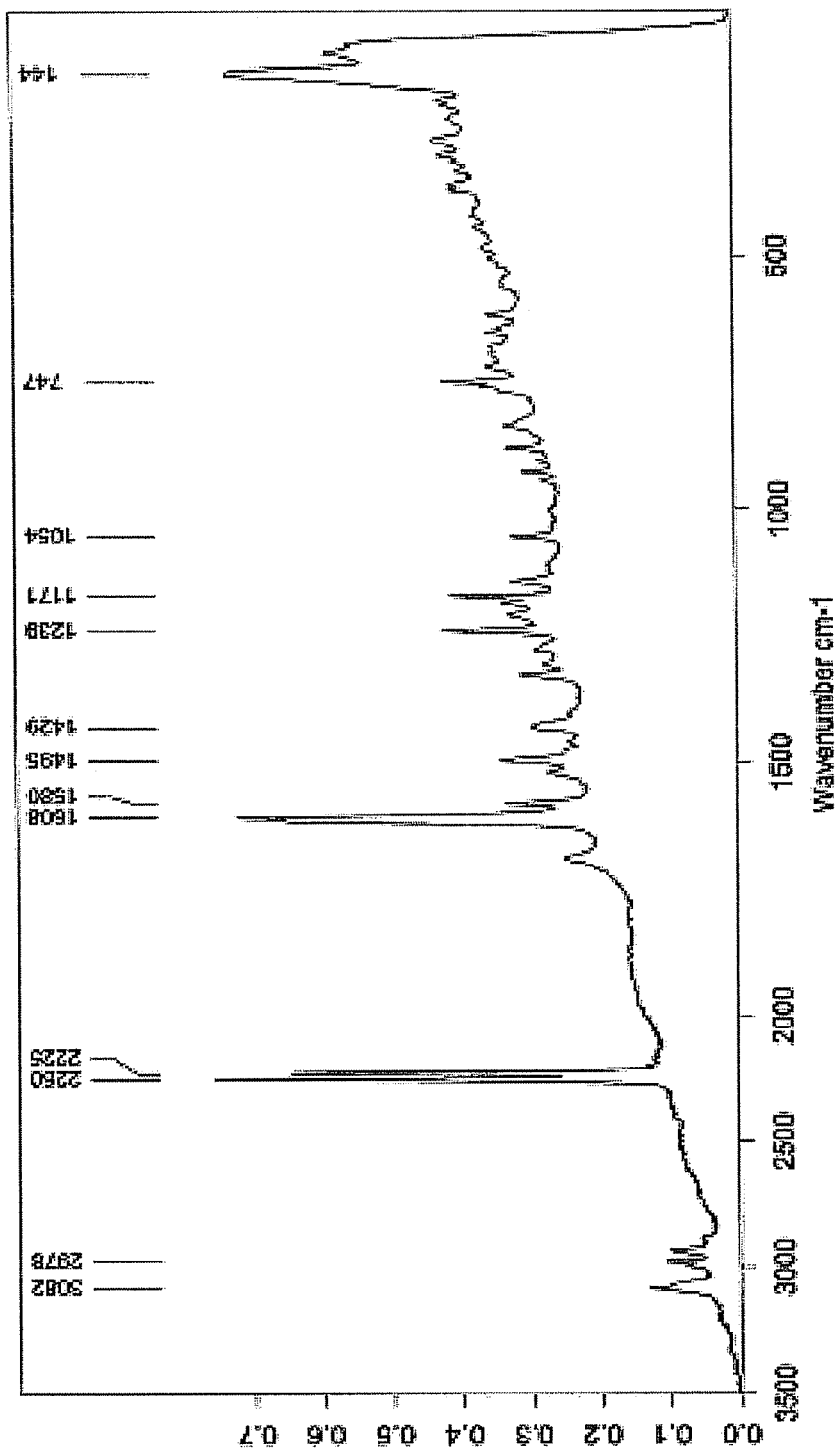
Figure 5D:
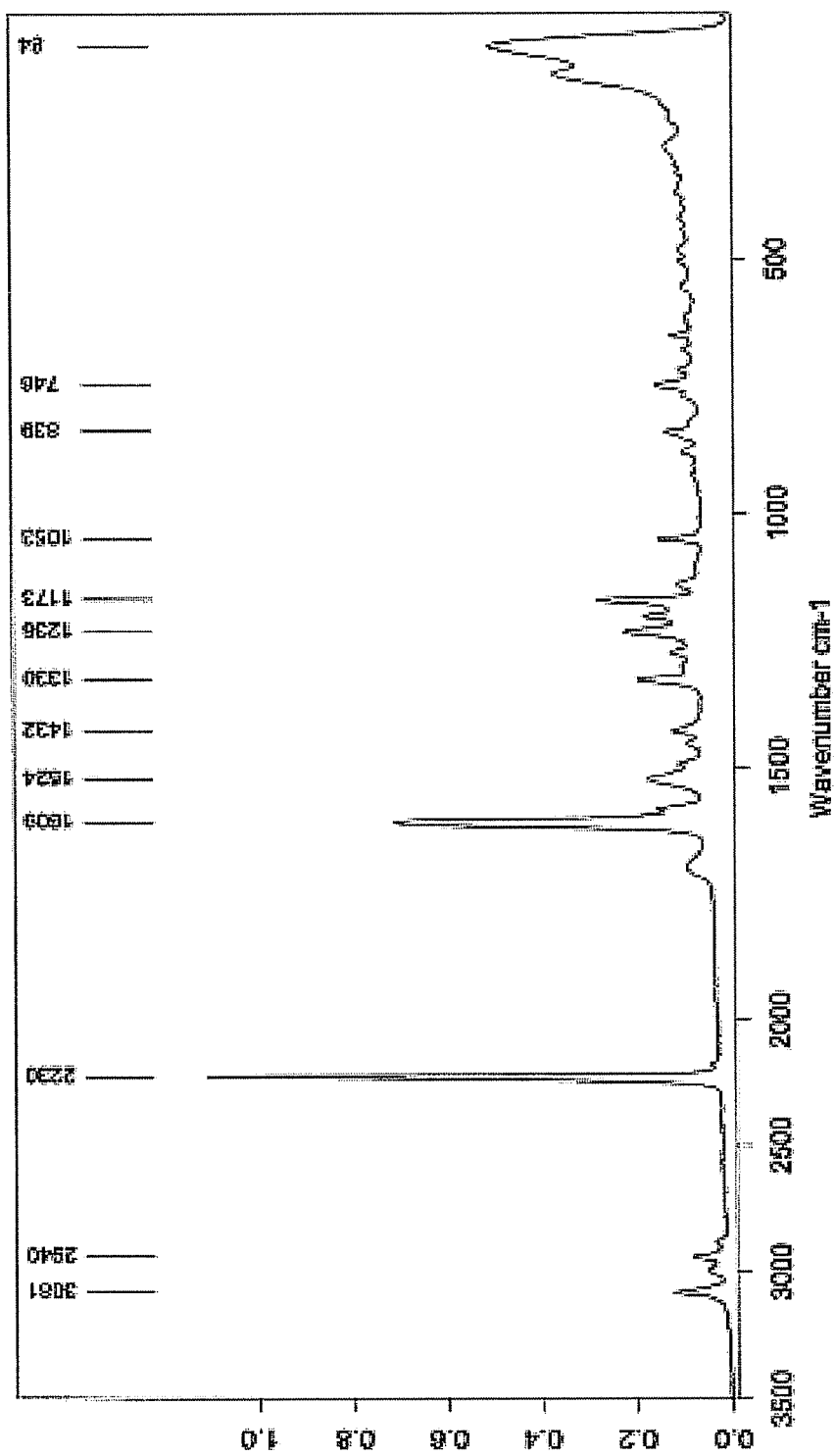

FIG. 17D shows that melting of polymorphs A or D produces the liquid crystalline B" polymorph instead of a truly isotropic liquid phase. Formation of a true liquid phase was not observed even after heating the sample to 200° C. Cooling the B" polymorph to ambient temperature does not result in recrystallization back to form A or D. This is verified by the absence of a melting endotherm in the DSC curve (FIG. 17D) of the sample reheated after it was melted then subsequently cooled to ambient temperature. The DSC curve also shows that the B" form undergoes a phase transition near 55° C. Similar glass transitions are observed for B', which along with the broad shoulder around 17° in FIG. 4D are the basis for their designation as liquid crystalline phases. The XRPD displays harmonic peaks for B', along with the broad shoulder around 17° in FIG. 4D which are the basis for their designation as liquid crystalline phases.

FIG. 17E shows that heating of polymorphs A and B" to 110° C. in the presence of D causes the A and B" forms to rearrange into D. This confirms that the A and B" are metastable phases below 130° C. that can be converted to form D. However, likely due to the high energetic barrier for the transition, the rates of conversion of A or B" to D are very slow without any D present initially to seed the crystallization. Thus forms A and B" can be considered to be practically stable at ambient temperature. Above 130° C., form D melts and changes to B" which now becomes the most stable form. Micronization of the polymorph A particles under dry conditions also produced ~25% conversion to B".

Relative Stability of Polymorphic Forms Under Humid Conditions

Polymorph A stays stable in its A form for at least 7 days under storage conditions of ambient temperature/75% RH (Relative Humidity), ambient temperature/100% RH, 30° C./75% RH and 50° C./0% RH. But it converts to B' when stored at 50° C./75% RH. Some of the results are shown in FIG. 17F. In fact, polymorph A stored at 25° C./60% RH and 30° C./65% RH were stable through 36 months and 9 months respectively while a sample stored at 40° C./75% RH converted to B' within one month. These results indicate that polymorph A converts to B' in the presence of moisture.

Polymorph D on the other hand, remains stable at 50° C./75% RH as well as the other conditions of ambient/75% RH, ambient/100% RH, 30° C./75% RH and 50° C./0% RH. In fact, polymorph D in the presence of moisture acts as the seed for the crystallization process and drives the transformation of polymorphs A and B' into D, similar to its role in seeding the A to D crystallization in dry conditions. FIG. 17G(a) shows the time evolution of polymorph A seeded with a small amount of D at 50° C./75% RH. The amount of polymorph D initially added to the sample is very small that it isn't detectable by the DSC with heating rate of 10° C./min. After 24 hours, most of the polymorph form A has been converted to B' but a small amount of sample has also been converted to D and the amount of sample in D increases over time. The transformation process is speeded up in FIG. 17G(b) by storing the sample in water at 50° C. Form A has been converted to both B' and D after 6 hours but the sample is predominantly in form D by 24 hours. This is in contrast to the conversion to B' of the pure A form which doesn't convert further to D. It is yet unclear if A can convert to D directly with seeding in water or if it only converts to B' (which subsequently converts to D in water). Further work has shown that the A and B' convert to D in the presence of moisture at lower temperatures also albeit at slower rates.

Relative Stability of Toluene Solvate in Toluene

Recrystallization of S-1 from a solvent/antisolvent system that uses toluene as the antisolvent produces the toluene solvate. Toluene solvate has a melting point near 100° C. with the enthalpy of melting 70±5 J/g. TGA graph of the toluene solvate in FIG. 20 shows that the toluene content in the solvate is ~7% which corresponds to one toluene molecule for every three molecules of S-1. The solvent/drug mass ratio stayed the same for each sample batch prepared and suggests that the toluene molecules reside inside the unit cell structure rather than in channels or layers outside the lattice. Owing to the low solubility of S-1 in toluene (<2 mg/mL), no noticeable transformation from form D to the toluene solvate was observed after suspension (50 mg/mL) in toluene for 4 days both at ambient temperature and 50° C. Sonication of the suspension for 10 minutes did produce partial transformation to the toluene solvate.

It will be appreciated by a person skilled in the art that the present invention is not limited by what has been particularly shown and described hereinabove. Rather, the scope of the invention is defined by the claims that follow:

What is claimed is:

1. A method of treating a condition caused by androgen decline in aging male (ADAM) or androgen decline in female (ADIF) comprising administering a composition comprising a solid form D of (S)—N-(4-cyano-3-(trifluoromethyl)phenyl)-3-(4-cyanophenoxy)-2-hydroxy-2-methylpropanamide compound, characterized by an X-ray powder diffraction pattern comprising unique peaks at °2θ (d value Å) angles of about 4.4 (19.9), 8.5 (10.4), 8.8 (10.0), 11.3 (7.8), 12.7 (6.9), 13.8 (6.4), 14.4 (6.1), 14.6 (6.0), 15.1 (5.8), 16.1 (5.5), 16.6 (5.3), 16.9 (5.2), 18.0 (4.9), 18.7 (4.7), 19.0 (4.6), 19.4 (4.55), 20.8 (4.25), 22.1 (4.0), 22.7 (3.9), 23.1 (3.8), 23.4 (3.8), 24.7 (3.6), 24.9 (3.56), 25.3 (3.51), 27.8 (3.2) and 29.3 (3.0).

2. The method of claim 1, wherein said condition caused by androgen decline in aging male (ADAM) is selected from fatigue, depression, decreased libido, sexual dysfunction, erectile dysfunction, hypogonadism, osteoporosis, hair loss, anemia, obesity, sarcopenia, osteopenia, benign prostate hyperplasia, and prostate cancer or any combination thereof.

3. The method of claim 1, wherein said condition caused by androgen decline in female (ADIF) is selected from sexual dysfunction, decreased sexual libido, hypogonadism, sarcopenia, osteopenia, osteoporosis, depression, anemia, hair loss, obesity, endometriosis, uterine cancer, and ovarian cancer or any combination thereof.

4. A method of treating chronic muscular wasting comprising administering a composition comprising a solid form D of (S)—N-(4-cyano-3-(trifluoromethyl)phenyl)-3-(4-cyanophenoxy)-2-hydroxy-2-methylpropanamide compound, characterized by an X-ray powder diffraction pattern comprising unique peaks at °2θ (d value Å) angles of about 4.4 (19.9), 8.5 (10.4), 8.8 (10.0), 11.3 (7.8), 12.7 (6.9), 13.8 (6.4), 14.4 (6.1), 14.6 (6.0), 15.1 (5.8), 16.1 (5.5), 16.6 (5.3), 16.9 (5.2), 18.0 (4.9), 18.7 (4.7), 19.0 (4.6), 19.4 (4.55), 20.8 (4.25), 22.1 (4.0), 22.7 (3.9), 23.1 (3.8), 23.4 (3.8), 24.7 (3.6), 24.9 (3.56), 25.3 (3.51), 27.8 (3.2) and 29.3 (3.0).

* * * * *